United States Patent
Palczewski et al.

(10) Patent No.: US 10,568,851 B2
(45) Date of Patent: *Feb. 25, 2020

(54) COMPOUNDS AND METHODS OF TREATING OCULAR DISORDERS

(71) Applicant: Case Western Reserve University, Cleveland, OH (US)

(72) Inventors: Krzysztof Palczewski, Bay Village, OH (US); Yu Chen, Mayfield Heights, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 14/262,141

(22) Filed: Apr. 25, 2014

(65) Prior Publication Data

US 2014/0235562 A1 Aug. 21, 2014

Related U.S. Application Data

(63) Continuation-in-part of application No. PCT/US2012/061931, filed on Oct. 25, 2012.

(60) Provisional application No. 61/551,148, filed on Oct. 25, 2011, provisional application No. 61/904,218, filed on Nov. 14, 2013.

(51) Int. Cl.
| | | |
|---|---|---|
| A61K 31/4178 | (2006.01) |
| A61K 31/495 | (2006.01) |
| A61K 31/18 | (2006.01) |
| A61K 31/155 | (2006.01) |
| A61K 31/505 | (2006.01) |
| A61K 31/454 | (2006.01) |
| A61K 31/517 | (2006.01) |
| A61K 31/52 | (2006.01) |
| A61K 31/4164 | (2006.01) |
| A61K 31/4453 | (2006.01) |
| A61K 31/475 | (2006.01) |

(52) U.S. Cl.
CPC ............ *A61K 31/155* (2013.01); *A61K 31/18* (2013.01); *A61K 31/4164* (2013.01); *A61K 31/4178* (2013.01); *A61K 31/4453* (2013.01); *A61K 31/454* (2013.01); *A61K 31/475* (2013.01); *A61K 31/495* (2013.01); *A61K 31/505* (2013.01); *A61K 31/517* (2013.01); *A61K 31/52* (2013.01)

(58) Field of Classification Search
CPC .. A61K 31/52; A61K 31/4164; A61K 31/155; A61K 31/517; A61K 31/18; A61K 31/4453; A61K 31/505; A61K 31/495; A61K 31/454; A61K 31/475; A61K 31/4178

See application file for complete search history.

(56) References Cited

U.S. PATENT DOCUMENTS

| | | | |
|---|---|---|---|
| 10,117,868 B2 * | 11/2018 | Palczewski | A61K 45/06 |
| 2005/0059744 A1 * | 3/2005 | Donello | A61K 31/135 514/649 |
| 2011/0104155 A1 * | 5/2011 | Rekik | A61K 9/0048 424/133.1 |

OTHER PUBLICATIONS

Wenzel et al. Molecular mechanisms of light-induced photoreceptor apoptosis and neuroprotection for retinal degeneration. Progress in Retinal and Eye Research 24 (2005) 275-306.*
Shen et al. Effect of Guanabenz on Rat AMD Models and Rabbit Choroidal Blood Flow. The Open Ophthalmology Journal, 2011, 5, 27-31.*
Bromocriptine. https://en.wikipedia.org/wiki/Bromocriptine#cite_ref-19 accessed on Jul. 31, 2018 (Year: 2018).*

* cited by examiner

*Primary Examiner* — Yih-Horng Shiao
(74) *Attorney, Agent, or Firm* — Tarolli, Sundheim, Covell & Tummino LLP

(57) ABSTRACT

A method of treating an ocular disorder in a subject includes administering to the subject a therapeutically effective amount of an agent that modulates at least one target in a signaling cascade associated with light induced retinal degeneration, aberrant all-trans-retinal accumulation, and/or generation of reactive oxygen species (ROS).

18 Claims, 30 Drawing Sheets

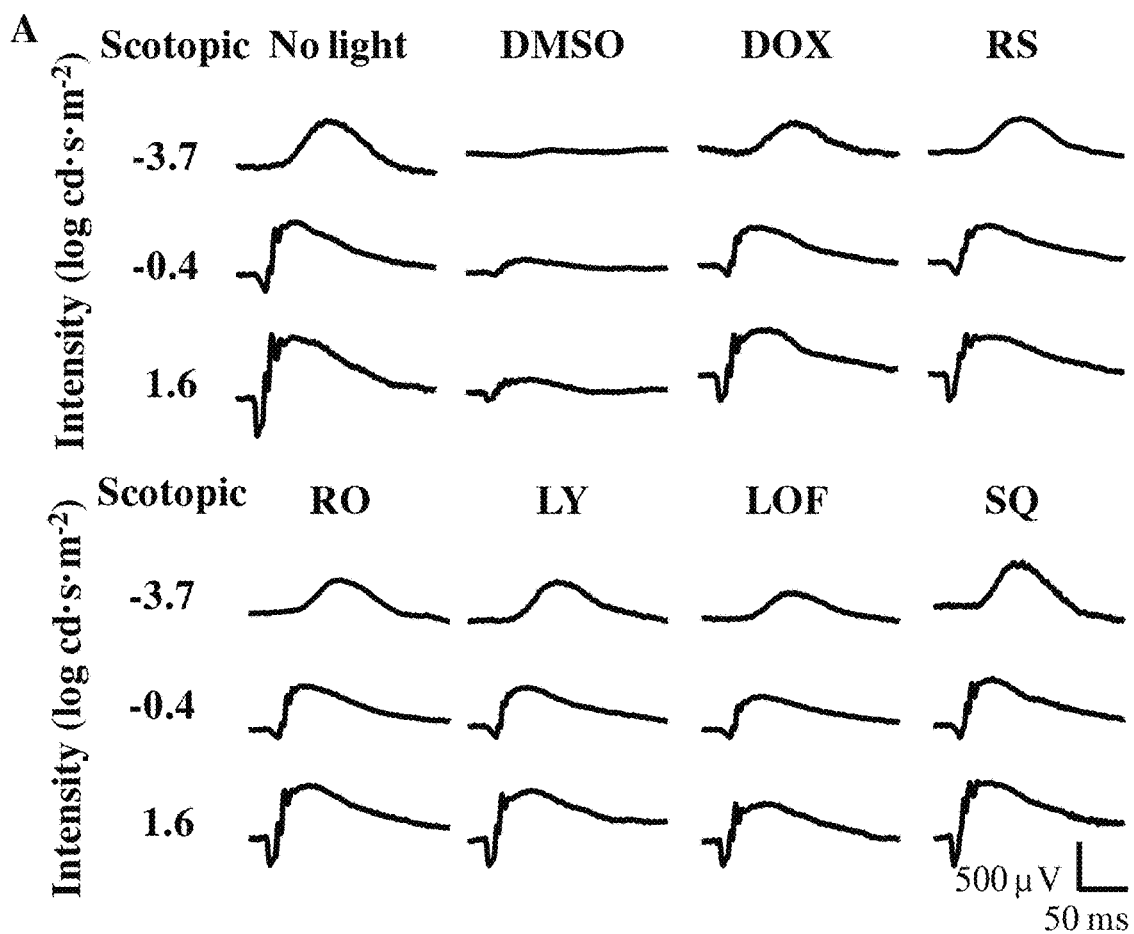
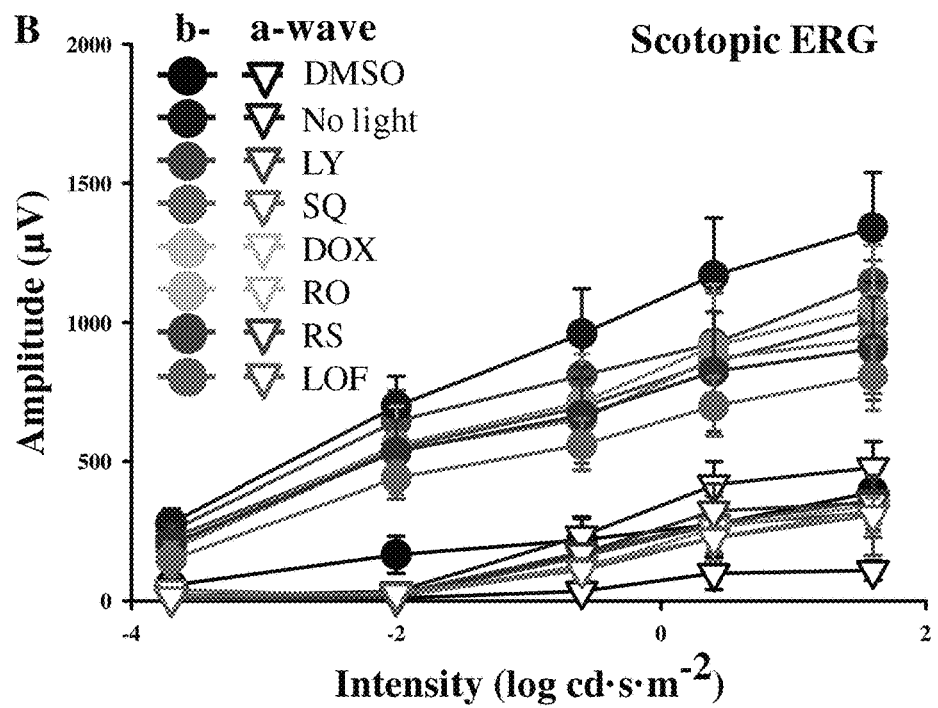
Fig. 24

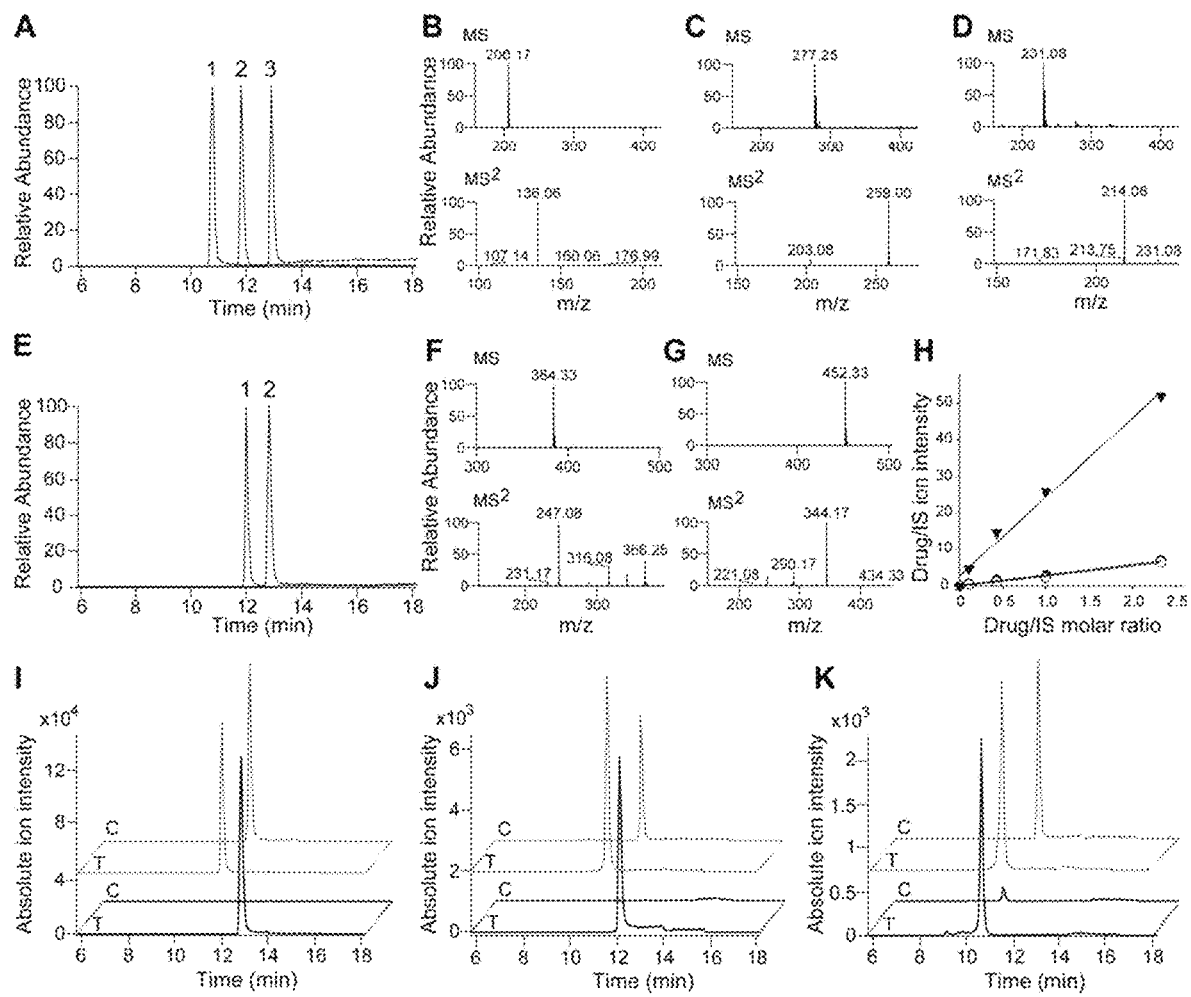
Figs. 29A-K

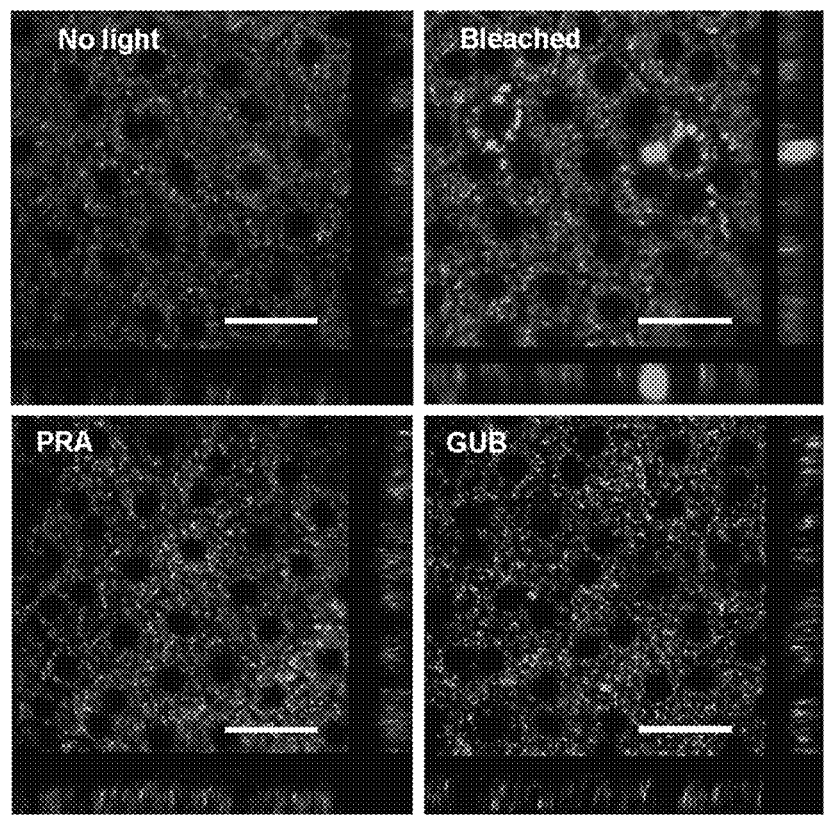
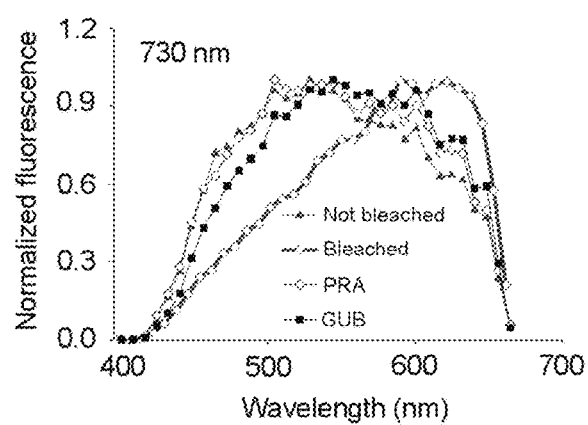 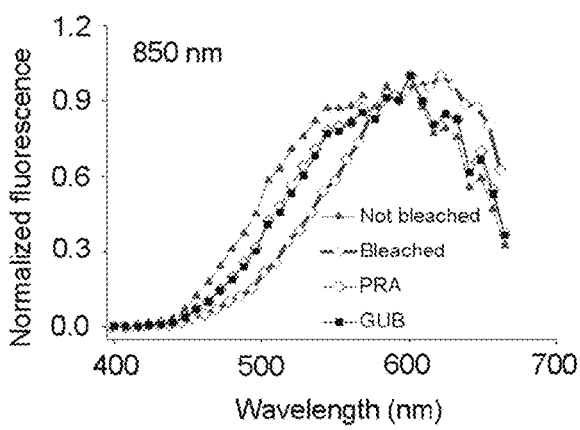
Figs. 30A-B

COMPOUNDS AND METHODS OF TREATING OCULAR DISORDERS

RELATED APPLICATION

This application is a Continuation-in-Part of PCT Application No. PCT/US2012/061931, filed Oct. 25, 2012, which claims the benefit of U.S. Provisional Application Nos. 61/551,148, filed Oct. 25, 2011 and claims priority from U.S. Provisional Application Ser. No. 61/904,218 filed Nov. 14, 2013, the subject matter of which are incorporated herein by reference in their entirety.

GOVERNMENT FUNDING

This invention was made with government support under Grant No. EY021126 awarded by The National Institutes of Health. The United States government has certain rights in the invention.

TECHNICAL FIELD

This application relates to compounds and methods of treating ocular and/or retinal disorders that are associated with light induced retinal degeneration, aberrant all-trans-retinal clearance in the retina, and/or the generation of reactive oxygen species.

BACKGROUND

To sustain vision, atRAL released from light-activated visual pigments, including rhodopsin, must be continuously isomerized back to its 11-cis isomer. This process occurs by a sequence of reactions catalyzed by membrane-bound enzymes of the retinoid cycle located in rod and cone photoreceptor outer segments and the retinal pigmented epithelium (RPE). Regeneration of rhodopsin requires 11-cis-retinal (11-cis-RAL) supplied from the RPE, but cone pigments are also regenerated in cone-dominant species by a separate "cone visual cycle". A high flux of retinoids through the retinoid cycle, as occurs during intense light exposure, can cause elevated levels of toxic intermediates, especially atRAL, that can induce photoreceptor degeneration. Toxic effects of atRAL include caspase activation and mitochondrial-associated cell death, but the precise sequence of molecular events that leads to photoreceptor degeneration remains to be clarified.

Oxidative stress is one major mechanism contributing to photoreceptor cell death in animal models of retinal degeneration, including light-induced retinopathy. Tightly regulated low levels of reactive oxygen species (ROS) are needed to mediate physiological functions including cell survival, growth, differentiation and metabolism. NADPH oxidase is the primary enzymatic source of $O_2^-$ and $H_2O_2$ involved in retinal degeneration. atRAL stimulates the production of reactive oxygen species superoxide via NADPH oxidase, however such stimulation does not result from a direct interaction between atRAL and this enzyme. Effective compositions and methods to reduce and minimize the production and release of ROSs in patients suffering from a variety of disparate ocular disorders would be a great boon to medicine and serve to reduce and eliminate a substantial amount of human suffering.

SUMMARY

Embodiments described herein relate to compounds and methods of treating an ocular disorder in a subject associated with light induced retinal degeneration, aberrant all-trans-retinal clearance and/or reactive oxygen species (ROS) generation in the retina. The ocular disorder can include, for example, retinal disorders, such as retinal degeneration, geographic atrophy (GA), macular degeneration, including age-related macular degeneration, Stargardt disease, and retinitis pigmentosa.

The methods can include administering to a subject with an ocular disorder associated with light induced retinal degeneration, aberrant all-trans-RAL clearance and/or ROS production a therapeutically effective amount of one or more agents that can inhibit and/or antagonize Gs- or Gq-protein coupled receptor activation, inhibit and/or antagonize the Gq signaling cascade (e.g., agents that inhibit or antagonize PLC activation, $IP_3$ binding to its receptor), inhibit or antagonize the Gs signaling cascade (e.g., agents that inhibit and/or antagonize andenylyl cyclase activation) and/or agents that activate Gi signaling cascade in a retina cell). These agents can be used alone and/or in combination with each other as well as with other agents to treat retinal disorders associated with light induced retinal degeneration, all-trans-retinal accumulation and/or reactive oxygen species generation.

In some embodiments, the agent can include at least one, two, three, or four or more of a Gs or Gq coupled serotonin receptor antagonist, an alpha 1 adrenergic antagonist, an alpha-2 adrenergic receptor agonist, an adenylyl cyclase inhibitor, an M3 receptor antagonist, or a PLC inhibitor.

In another embodiment, the agent can be delivered to the subject by at least one of topical administration, systemic administration, and/or intraocular delivery including intravitreal injection. In one example, the agent can be provided in an ocular preparation for sustained delivery.

were administered by intraperitoneal injection 1 h prior to light exposure. Retinylamine (Ret-NH$_2$) was gavaged 2 h before illumination (Light_Ret-NH$_2$). Dark-adapted Rdh8$^{-/-}$Abca4$^{-/-}$ mice unexposed to experimental light were included for the DHE probe treatment as well (No light). Retinas were harvested 3 h after illumination. ROS signals were obtained with same exposure setup under a fluorescence microscope. DAPI staining was performed simultaneously to visualize cell nuclei and gross retinal structure. Recorded ROS fluorescence intensity averaged from various areas was plotted as a histogram for group comparisons.

Figure 7:
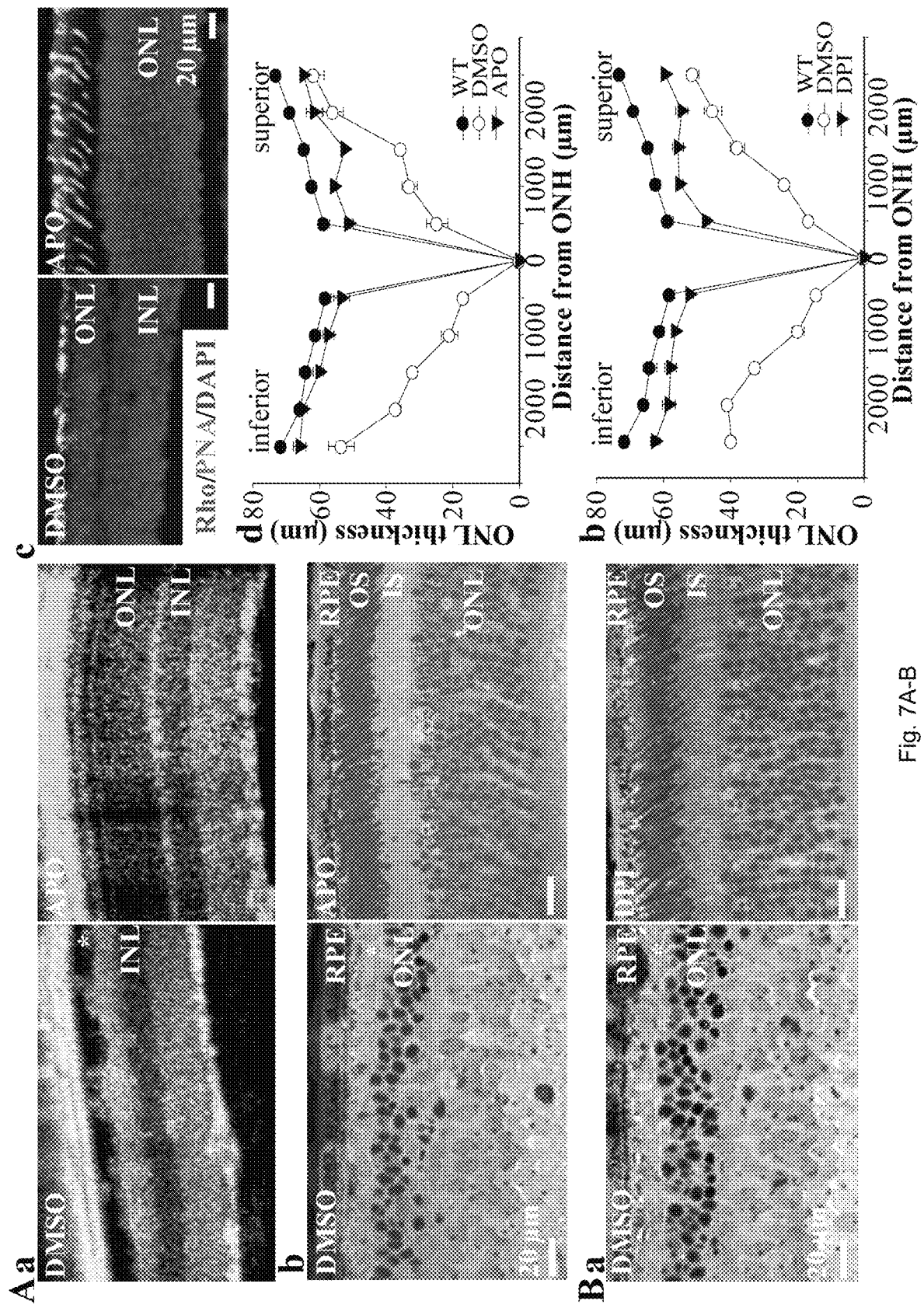

FIGS. 7(A-B) illustrate NADPH oxidase inhibitor protects Rdh8$^{-/-}$Abca4$^{-/-}$ mouse photoreceptors from light-induced degeneration. (A) 4- to 5-week old Rdh8$^{-/-}$Abca4$^{-/-}$ mice were exposed to white light at 10,000 lux for 30 min after pre-treatment with either vehicle control DMSO or APO. (B) Rdh8$^{-/-}$Abca4$^{-/-}$ mice were exposed to white light at 10,000 lux for 30 min after pre-treatment with either vehicle control (DMSO) or the structurally different NADPH oxidase inhibitor, DPI. For both APO and DPI pretreatment, evaluations performed 7 days after illumination included OCT imaging (a, * indicates disrupted photoreceptors in the retinal structure), retinal histological examination (b, * indicates disrupted and decreased length of outer and inner photoreceptor segments; 63×), photoreceptor IHC and measurements of outer nuclear layer thickness after DAPI staining (d, RPE, retinal pigmented epithelium; OS, outer segment; IS, inner segment; ONH, optic nerve head).

Figure 8:
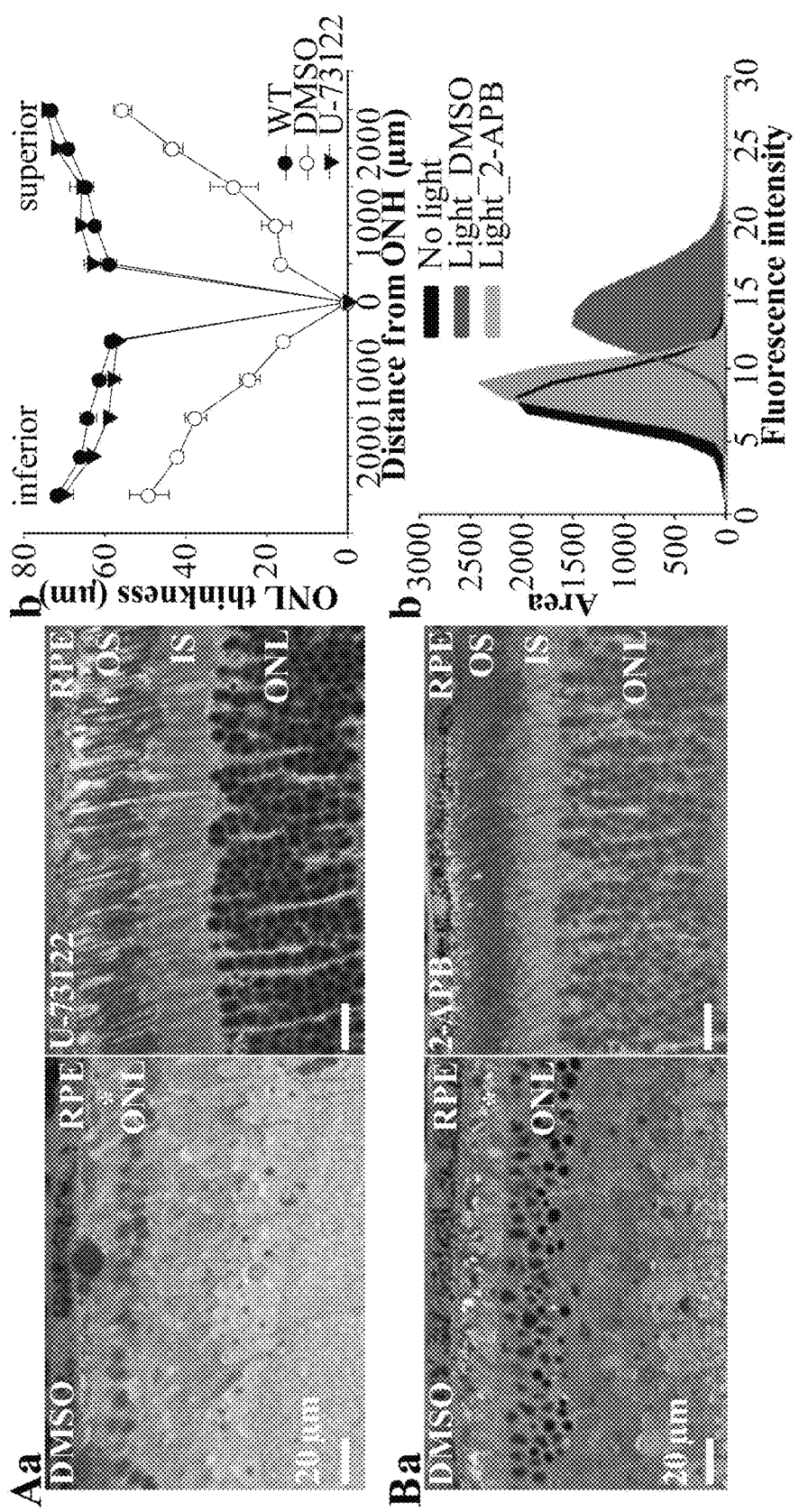

FIGS. 8(A-B) illustrate inhibition of PLC/IP$_3$/Ca$^{2+}$ signaling preserves retinal morphology in light-challenged Rdh8$^{-/-}$Abca4$^{-/-}$ mice. (A) 4- to 5-week old Rdh8$^{-/-}$Abca4$^{-/-}$ mice were exposed to white light at 10,000 lux for 30 min after pre-treatment with either vehicle control (DMSO) or the PLC inhibitor, U-73122. a, retinal histology (63×), with * indicating disorganized and reduced length of outer/inner segments, and b, analysis of ONL thickness were performed 7 days after illumination. (B) Light-challenged Rdh8$^{-/-}$Abca4$^{-/-}$ mice were pre-treated with either vehicle control (DMSO) or 2-APB, an antagonist against IP$_3$ mediated intracellular Ca$^{2+}$ release. a, retinal histology was analyzed 7 days after illumination; and b, In situ ROS production after 2-APB treatment was assessed as described in FIG. 2.

Figure 9:
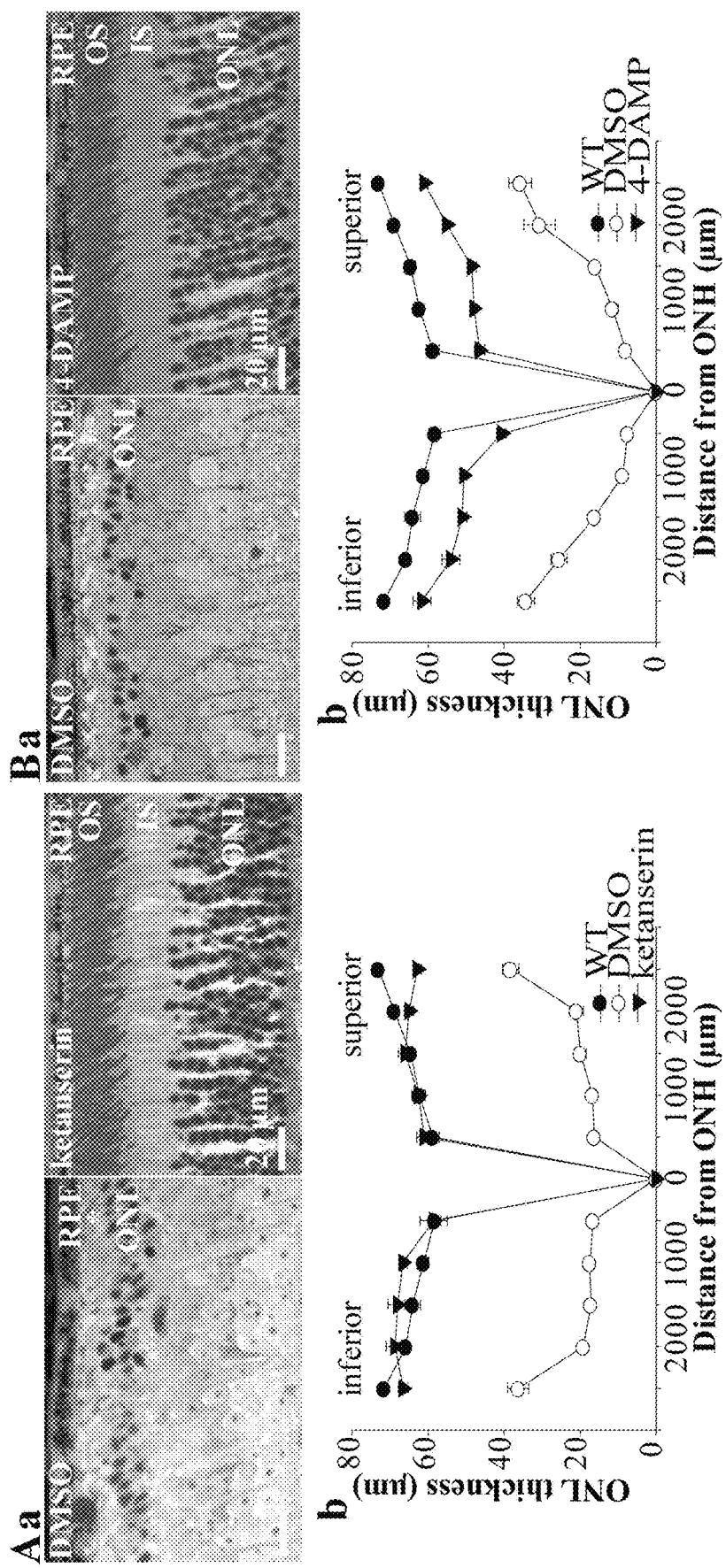

FIGS. 9(A-B) illustrate inhibition of either 5-HT$_{2A}$ or M3 protects against light-induced atRAL-mediated photoreceptor degeneration in Rdh8$^{-/-}$Abca4$^{-/-}$ mice. (A) 4- to 5-week old Rdh8$^{-/-}$Abca4$^{-/-}$ mice were exposed to white light at 10,000 lux for 30 min after pre-treatment with either vehicle control (DMSO) or the 5-HT$_{2A}$ receptor antagonist, ketanserin. (B) The M3 antagonist, 4-DAMP, was independently tested and compared with a vehicle control (DMSO) in illuminated Rdh8$^{-/-}$Abca4$^{-/-}$ mice. Seven days later, retinal histological examination (63×) (a, * indicates disrupted and reduced length of outer/inner segments) and measurements of ONL thickness (b) were performed.

Figure 10:
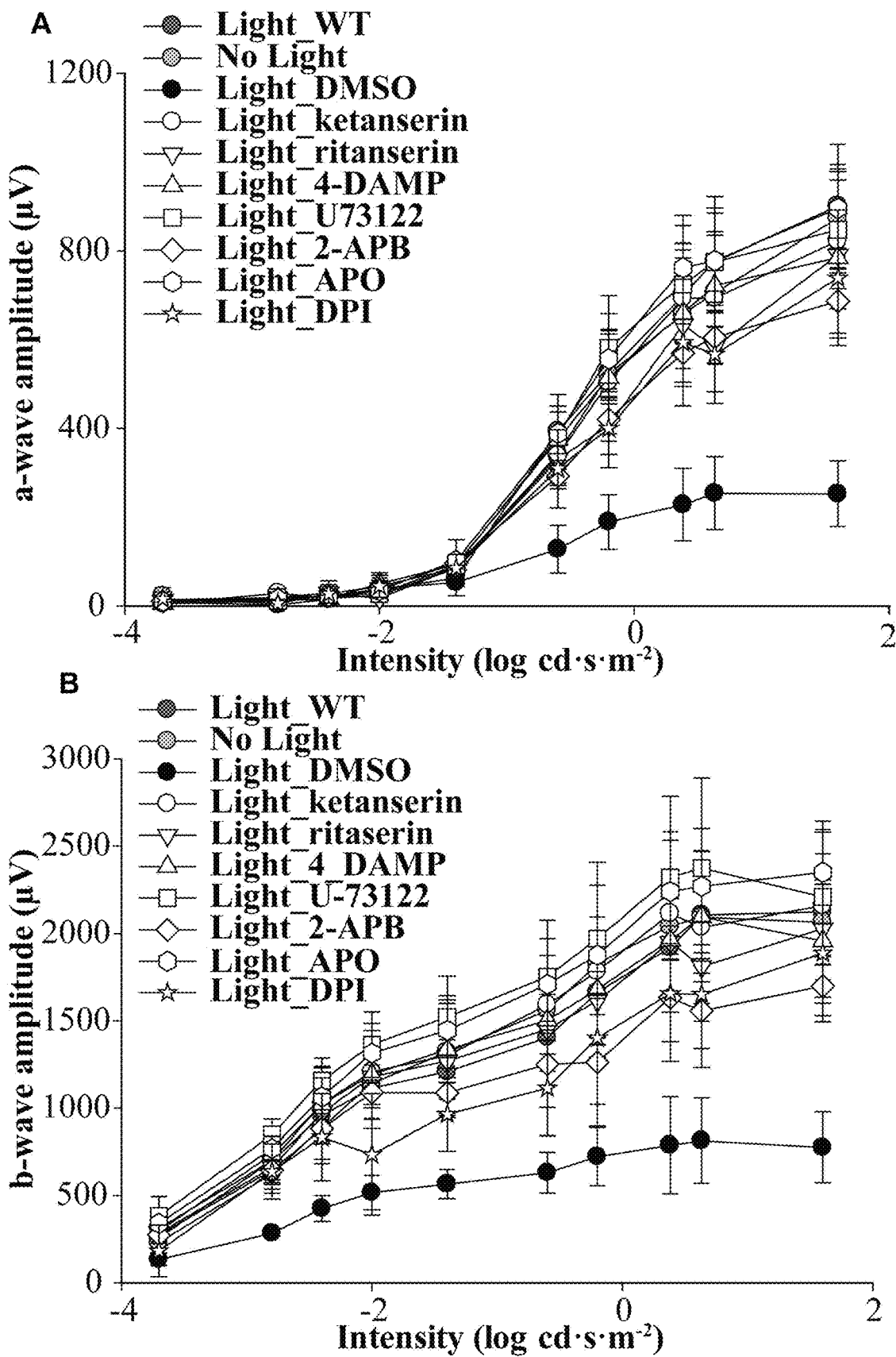

FIGS. 10(A-B) illustrate plots showing retinal function in Rdh8$^{-/-}$Abca4$^{-/-}$ mice is substantially preserved by several different treatments. Scotopic ERGs were recorded and both a-waves and b-waves were plotted to evaluate retinal function in Rdh8$^{-/-}$Abca4$^{-/-}$ mice 7 days after they were pretreated with the indicated compounds. Compared to wild type mice exposed to bright light (Light_WT) and Rdh8$^{-/-}$Abca4$^{-/-}$ mice without light exposure (No light), light exposure at 10,000 lux for 30 min significantly impaired retinal function as indicated by decreased a-wave and b-wave amplitude in mice treated with DMSO vehicle control (Light_DMSO). Compounds showing a protective effect against this light-induced retinopathy included: ketanserin, ritanserin, 4-DAMP, U-73122, 2-APB, APO and DPI.

Figure 11:
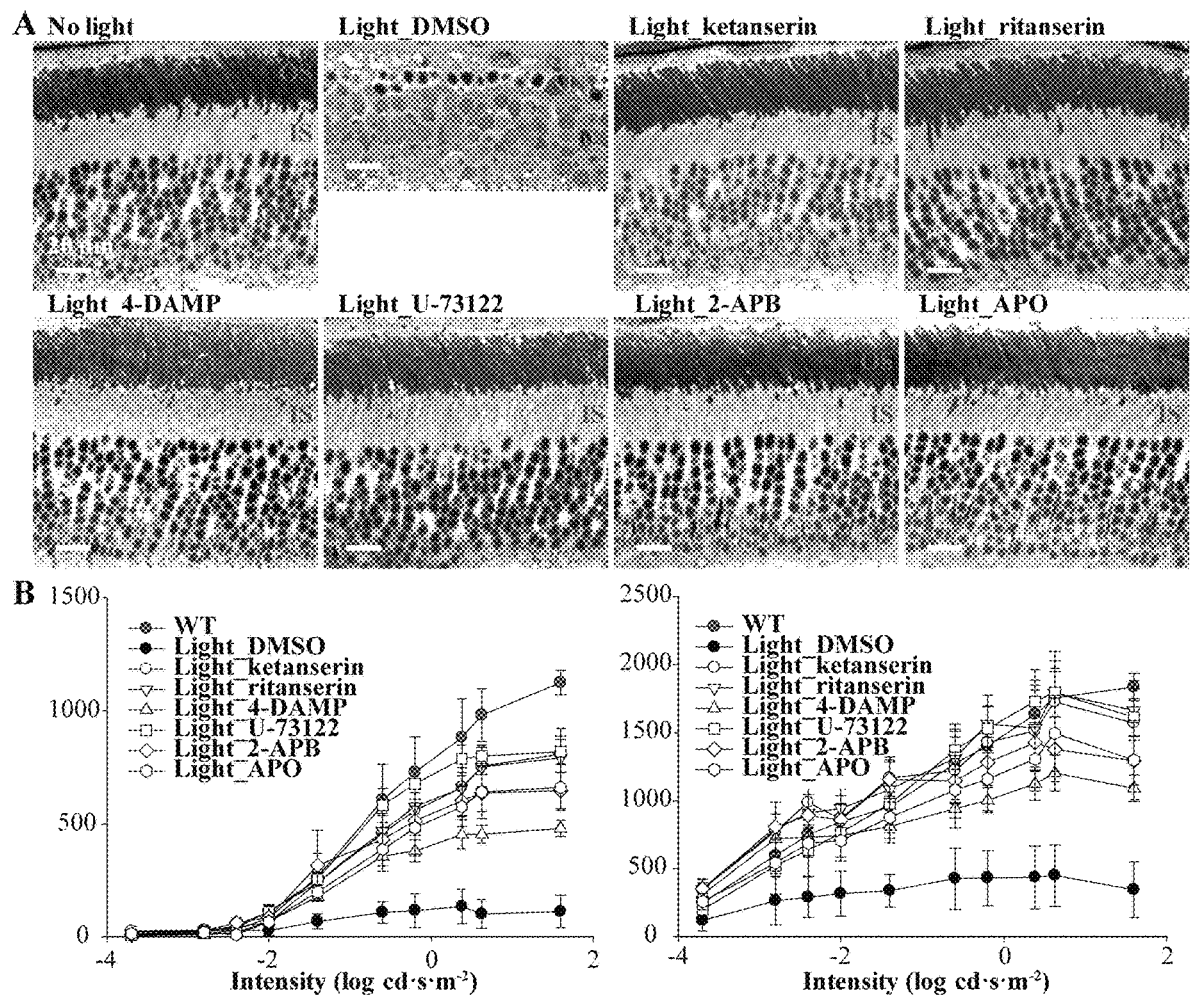

FIGS. 11(A-B) illustrate light-induced retinal degeneration in Balb/c mice. Twelve-week old Balb/c mice were dark-adapted followed by indicated pharmacological treatments via intraperitoneal injection 1 h prior to their exposure to white light at 10,000 lux for 2 h. All experimental evaluations were carried out 7 days later. Controls either without light exposure (No light) or with DMSO vehicle treatment followed by light exposure (Light_DMSO) were included for all analyses. (A) Retinal thin sections examined under light microscopy (63×) after toluidine blue staining. (B) Retinal function assessed by scotopic ERG in Balb/c mice seven days after the indicated pretreatments.

Figure 12:
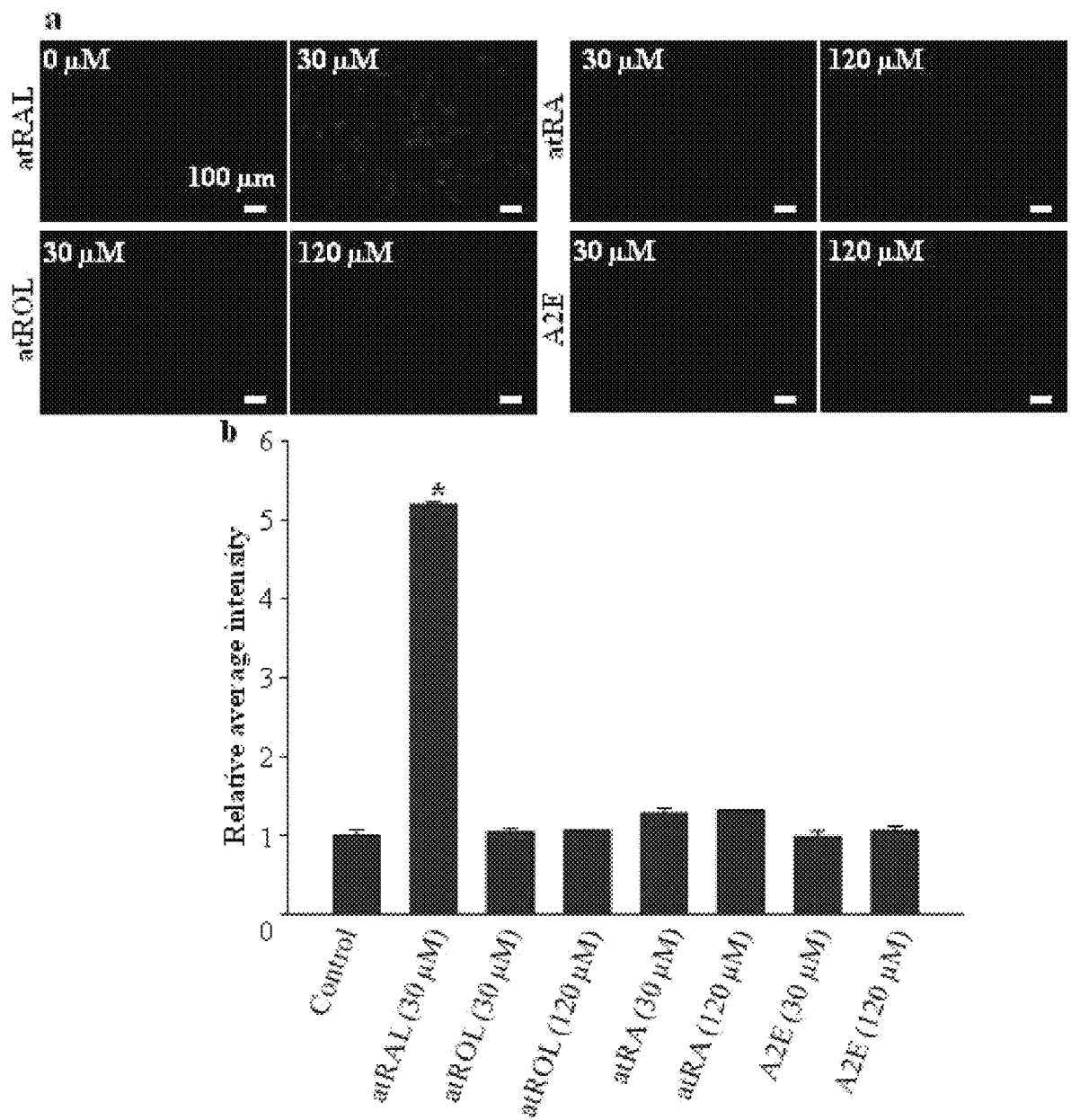

FIGS. 12(A-B) illustrate: (A) Fluorescent images obtained after the same exposure time of either atRAL, all-trans-retinol (atROL), all-trans-retinoic acid (atRA) or di-retinoid-pyridinium-ethanolamine (A2E) applied to cultured ARPE19 cells at indicated concentrations 1 h prior to addition of the ROS probe, DHE. (B) Quantification and comparison of ROS signals as described above.

Figure 13:
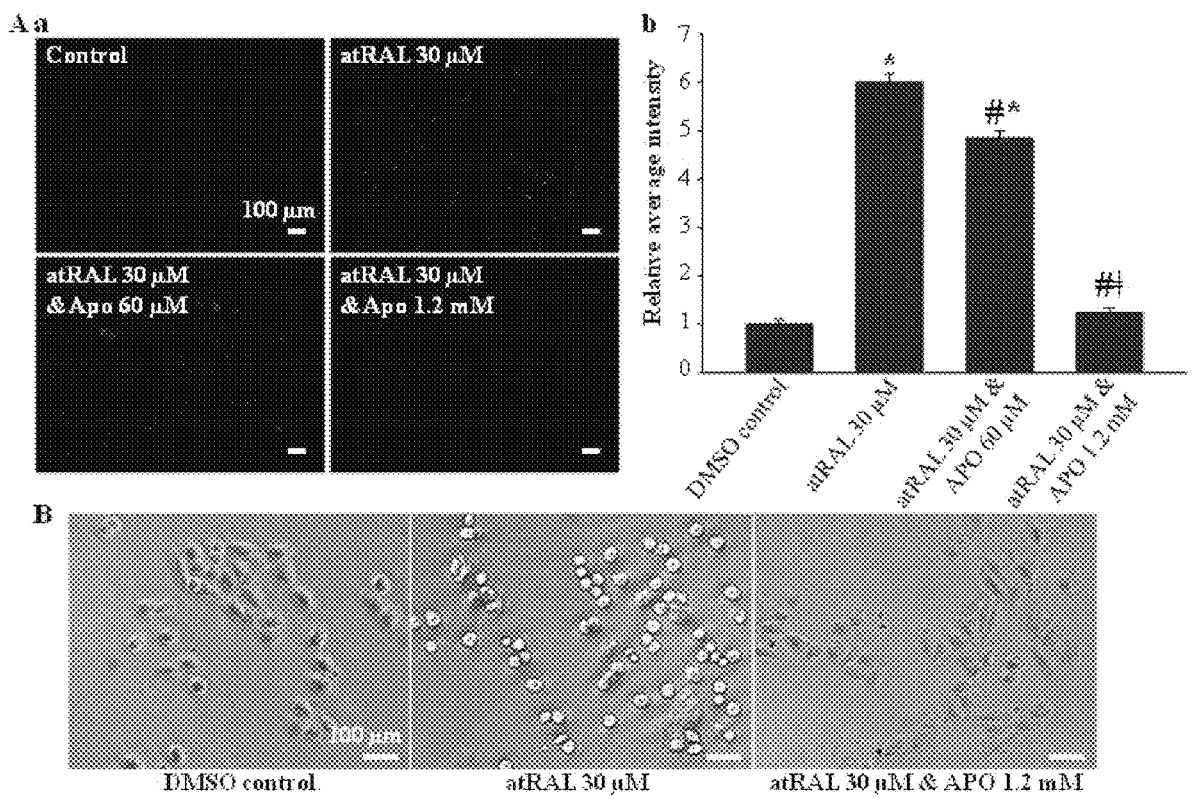

FIGS. 13(A-B) illustrate: (A) The inhibitory effect of APO on atRAL-induced ROS production was evaluated with the ROS probe, DHE, in cultured ARPE19 cells 1 h after indicated treatments. (a) Fluorescence images were recorded with the same exposure time and (b) statistical analyses were performed based on average fluorescence intensity generated by Metamorph imaging software (Means±SEM; * compared to DMSO control, p<0.01; # compared to atRAL 30 μM, p<0.01; ˜ compared to control, p>0.05). (B) APO treatment prevents atRAL-induced cell death in cultured APRE19 cells. Indicated treatments were applied to cultured ARPE19 cells for 24 h and the morphology of cells was observed by light microscopy (10×).

Figure 14:
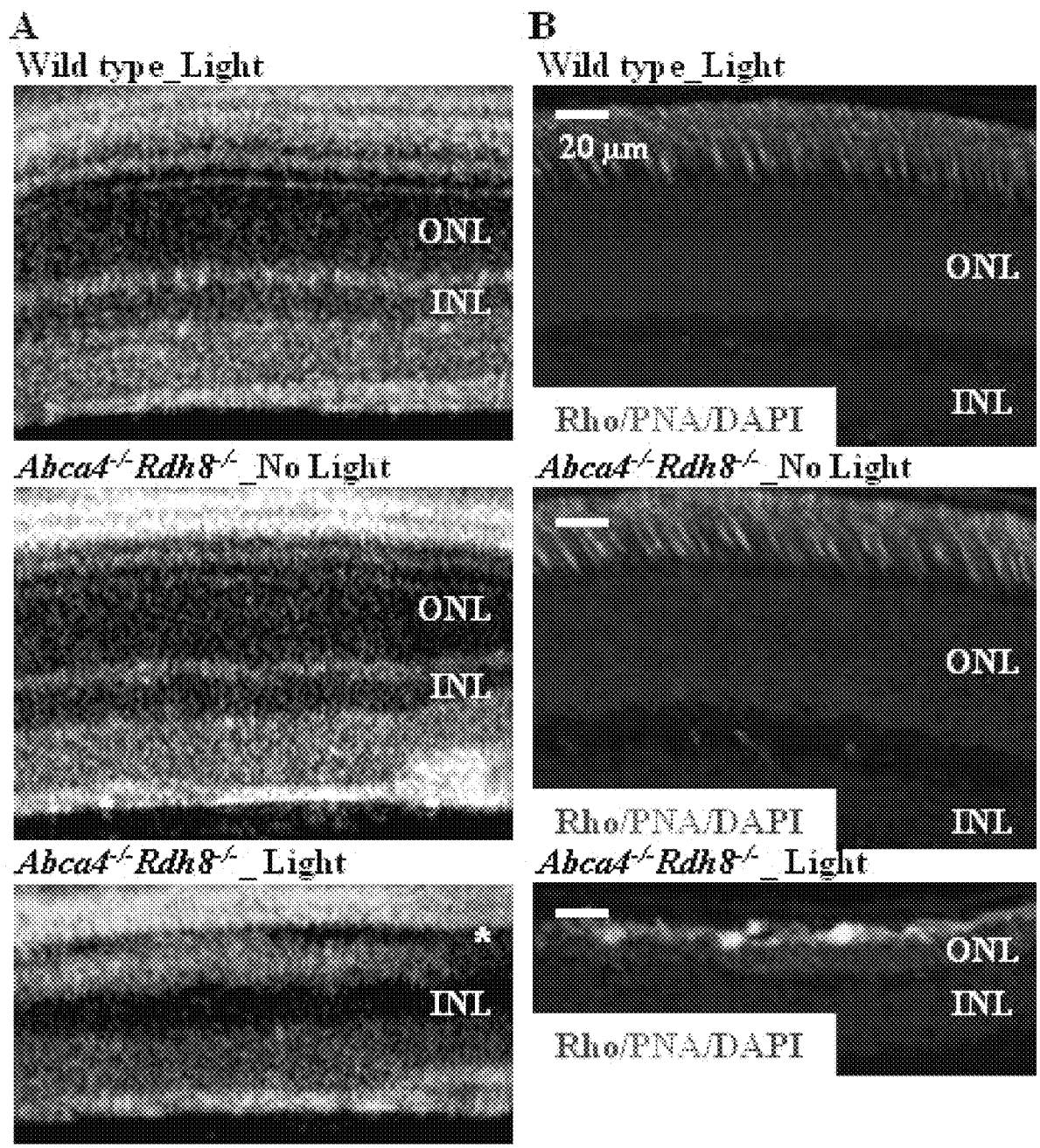

FIGS. 14(A-B) illustrate Rdh8$^{-/-}$Abca4$^{-/-}$ mouse photoreceptors exhibit light-induced degeneration in vivo. 4- to 5-week old Rdh8$^{-/-}$Abca4$^{-/-}$ mice develop severe light-induced photoreceptor degeneration compared to the wild type controls. Dark-adapted wild type and Rdh8$^{-/-}$Abca4$^{-/-}$ mice at 4 to 5 weeks of age were exposed to white light at 10,000 lux for 30 min. Seven days after this exposure, retinal structure and histology was examined by OCT (A) and immunohistochemistry (IHC) (B). Both OCT (see asterisk) and IHC indicate disrupted photoreceptor structure. Rdh8$^{-/-}$Abca4$^{-/-}$ mice unexposed to light were also included for these analyses.

Figure 15:
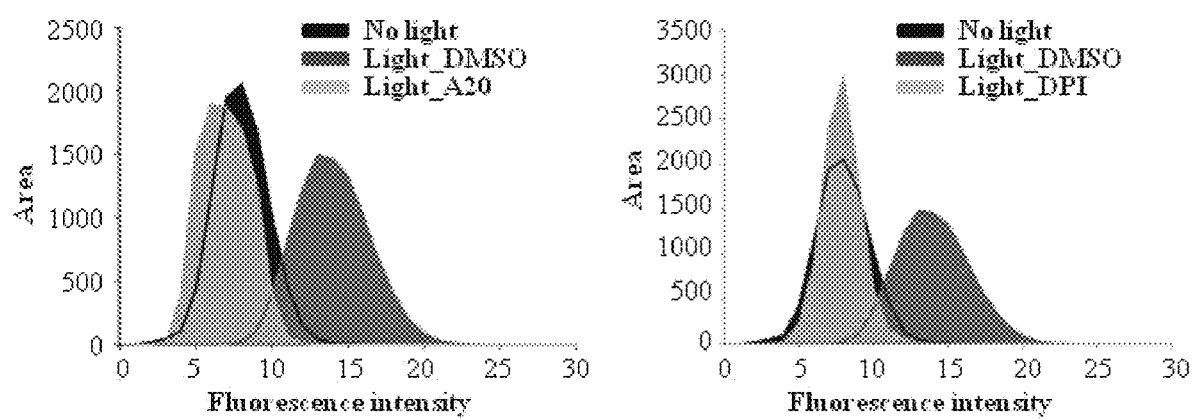

FIG. 15 illustrates 4- to 5-week old Rdh8$^{-/-}$Abca4$^{-/-}$ mice were treated with the ROS probe DHE 30 min prior to white light exposure at 10,000 lux for 30 min. DMSO vehicle control and the NADPH oxidase inhibitor DPI were administered by intraperitoneal injection 1 h prior to light exposure. R and S enantiomer of pregablin was gavaged 2 h before the light exposure. Retinas were harvested 3 h after light exposure. ROS signals (in red) from prepared cryosections were all obtained under a fluorescence microscope with same exposure setup. Recorded ROS signals are plotted as histograms for comparison with Rdh8$^{-/-}$Abca4$^{-/-}$ mice without light exposure (No Light), with light exposure and pretreated with either vehicle control (Light_DMSO), Amine 20 (Light_Amine 20) or the NADPH oxidase inhibitor, DPI (Light_DPI).

Figure 16:
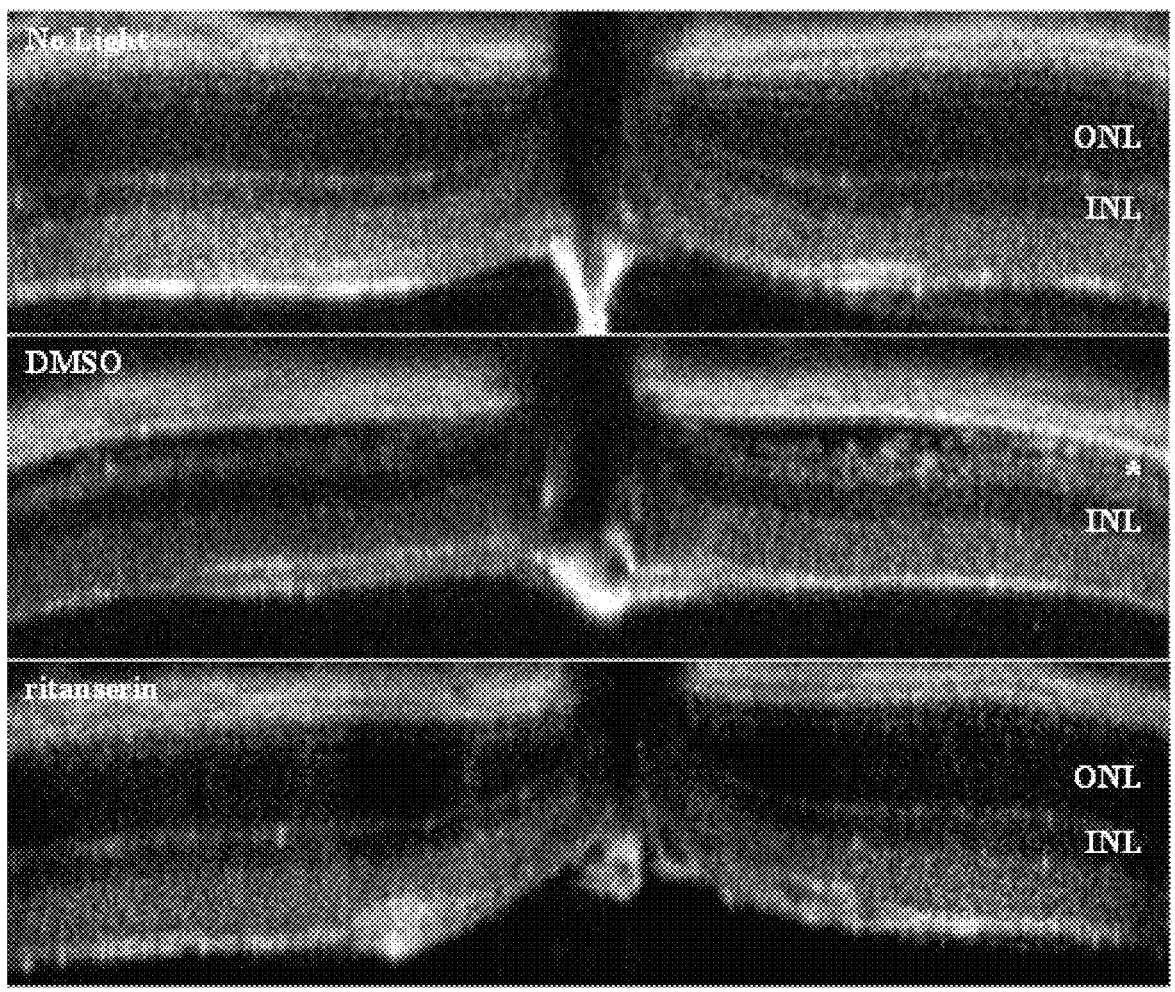

FIG. 16 illustrates pretreatment with a 5-HT$_{2A}$ antagonist protects Rdh8$^{-/-}$Abca4$^{-/-}$ mouse retinas from light-induced degeneration. 4- to 5-week old Rdh8$^{-/-}$Abca4$^{-/-}$ mice were exposed to white light at 10,000 lux for 30 min after pre-treatment with either vehicle control (DMSO) or the 5-HT$_{2A}$ receptor antagonist, ritanserin. Rdh8$^{-/-}$Abca4$^{-/-}$ mice without light exposure (No light) were included as negative controls. OCT images were taken to evaluate retinal structure 7 days after light exposure and revealed that ritanserin treatment substantially protected photoreceptors from light-induced degeneration (* indicates disrupted photoreceptors in the retinal structure in DMSO vehicle treated mice)

Figure 17:
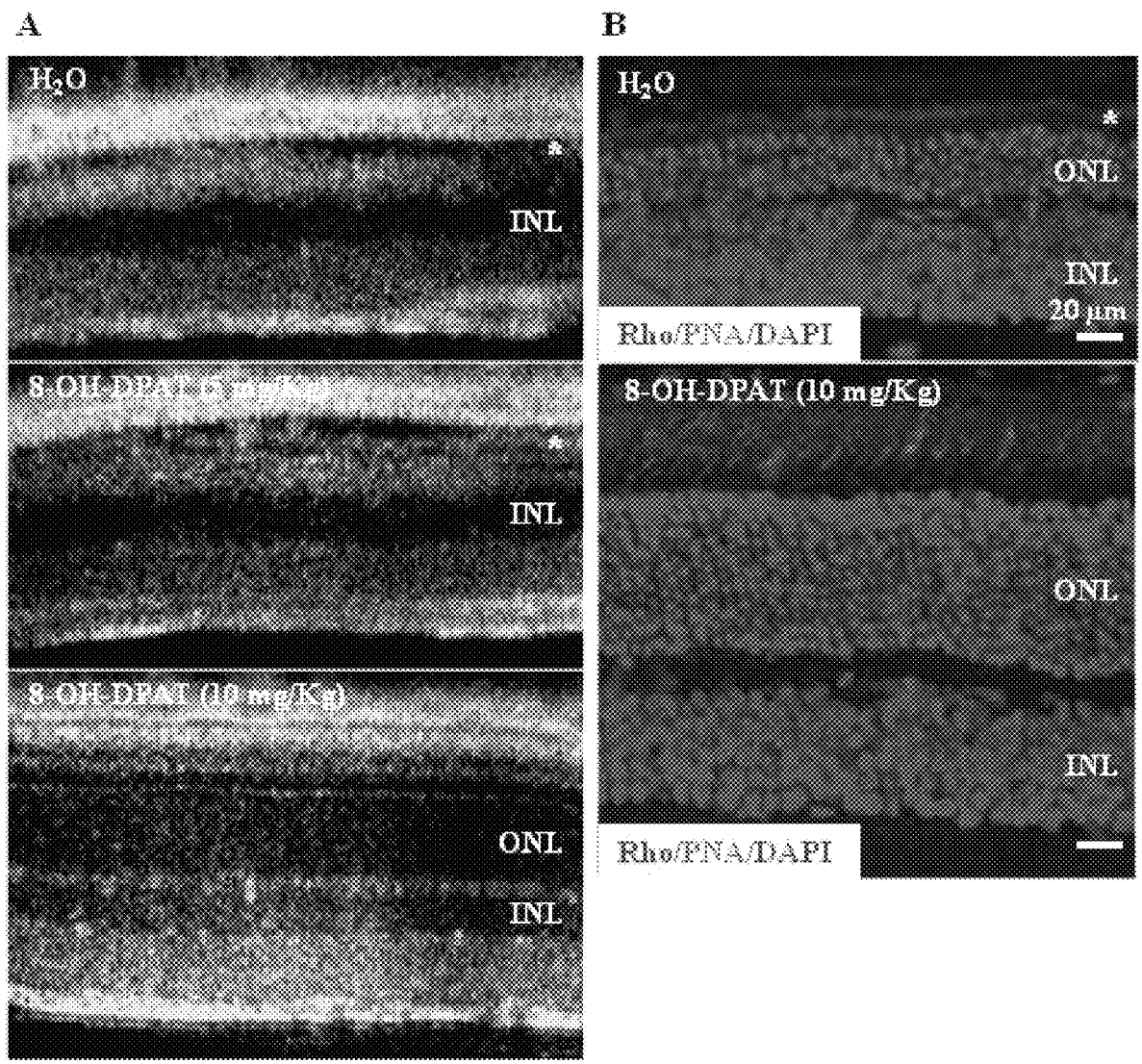

FIG. 17 illustrates 5-HT$_{1A}$ agonist pretreatment protects Rdh8$^{-/-}$Abca4$^{-/-}$ mouse retinas from light-induced degeneration. OCT imaging (A) and retinal IHC (B) was performed 7 days after exposing 4- to 5-week old Rdh8$^{-/-}$Abca4$^{-/-}$ mice to light at 10,000 lux for 30 min following pretreatment with the 5-HT$_{1A}$ agonist, 8-OH-DPAT. The protective effect of 8-OH-DPAT was dose-dependent.

Figure 18:
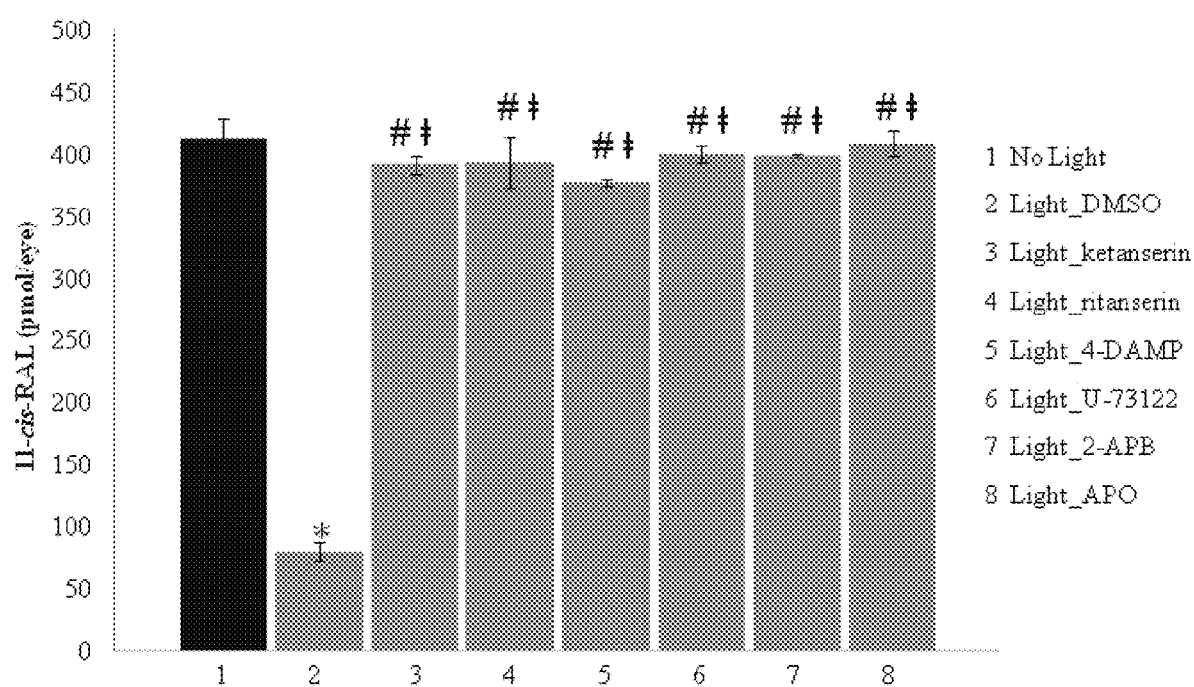

FIG. 18 illustrates 11-compared to No light, p>0.05). All listed pretreatments preserved 11-cis-retinal content. cis-Retinal (11-cis-RAL) content in Balb/c mouse eyes (pmol/eye) after indicated pretreatments was quantified by HPLC (* compared to No light, p<0.01; # compared to Light_DMSO, p<0.01).

Figure 19:
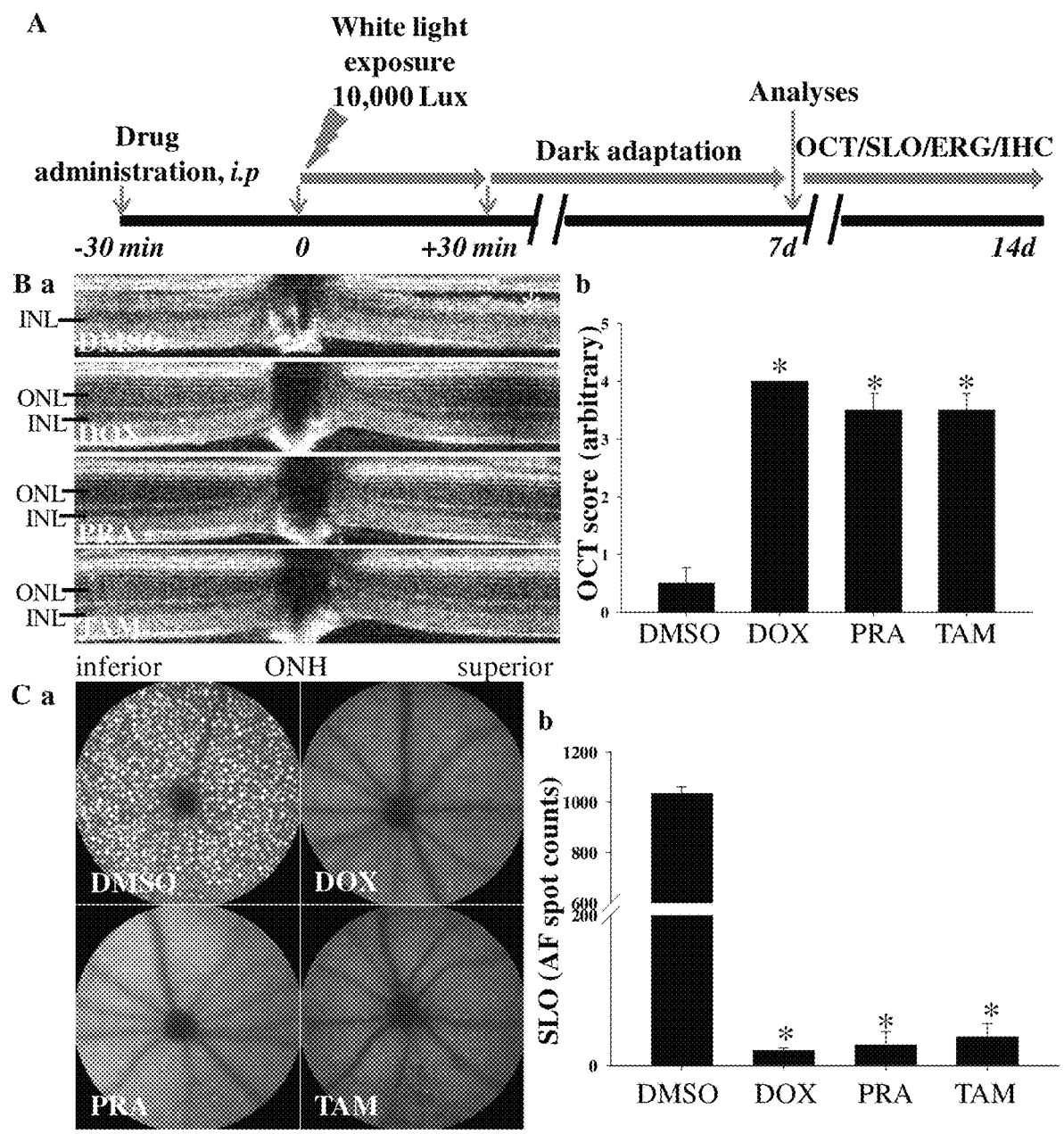

FIGS. 19(A-C) illustrate antagonists at α1-adrenergic receptor, a Gq-couple GPCR, protect retina from light-induced degeneration in Abca4$^{-/-}$Rdh8$^{-/-}$ mouse. (A) Scheme of pharmacological treatment: all the pharmacological compounds tested in the present study was administered via intraperitoneal injection to 4- to 5-week old Abca4$^{-/-}$Rdh8$^{-/-}$ mice 30 min prior to white light exposure at 10,000 Lux at the duration of 30 min. After light exposure, the mice were kept in the darkness for 7 to 14 days before morphological and functional examination by OCT, SLO, 1HC and ERG, respectively. (B) α1-adrenergic receptor antagonist, including doxazosin (DOX), prazosin (PRA) and tamsulosin (TAM) or vehicle control (DMSO) was administered to Abca4$^{-/-}$Rdh8$^{-/-}$ mice prior to white light exposure. OCT imaging was performed 7 days later to evaluate retinal morphology. a. Representative OCT images were presented. * indicates severely disrupted photoreceptor structure; ONH, optic nerve head; ONL, outer nuclear layer; INL inner nuclear layer. b. OCT scores were summarized from different treatment groups and subject to statistical analysis (Means±SEM; compared to DMSO control, * p<0.01). (C) SLO imaging was performed 8 days after light exposure. a. Retinal autofluorescence images. b. The number of retinal autofluorescence spots were counted and summarized for statistical analysis (Means±SEM; * compared to DMSO control, p<0.01).

Figure 20:
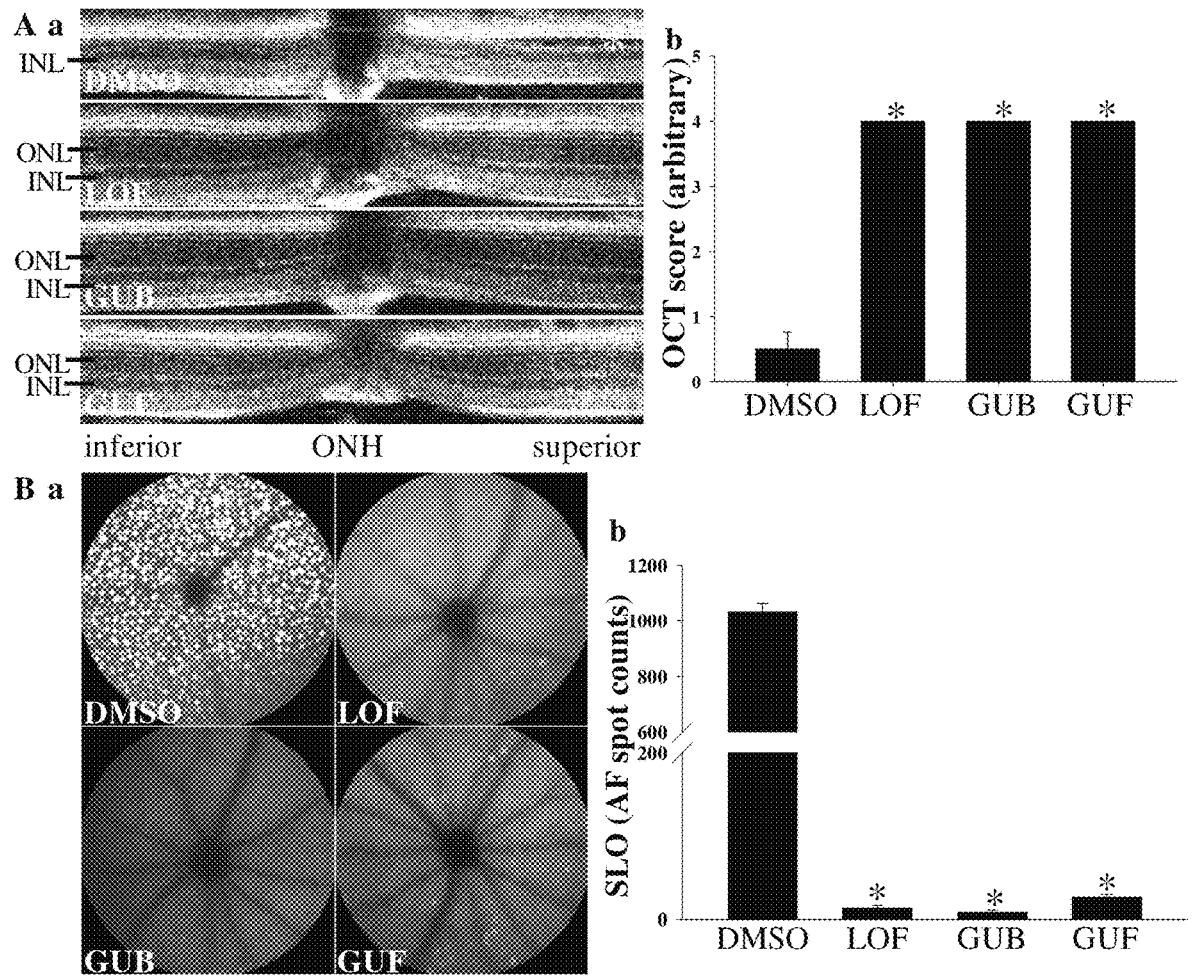

FIGS. 20(A-B) illustrate the agonists at α2-adrenergic receptor, a Gi-couple GPCR, protect retina from light-induced degeneration in Abca4$^{-/-}$Rdh8$^{-/-}$ mouse. α2-adrenergic receptor agonist, lofexidine (LOF), guanabenz (GUB) and guanafacine (GUF), was delivered to 4- to 5-week old Abca4$^{-/-}$Rdh8$^{-/-}$ mice through intraperitoneal injection prior to white light exposure at the intensity of 10,000 Lux for 30 min. DMSO was included as a vehicle control. (A) OCT imaging was carried out to evaluate the effect of each treatment 7 days after light exposure. a. OCT images: * indicates markedly damaged photoreceptor structure; ONH, optic nerve head; ONL, outer nuclear layer; INL inner nuclear layer. b. Statistical analysis of OCT scores (Means±SEM; compared to DMSO control, * p<0.01). (B) SLO imaging was performed at autofluorescene mode 8 days after light exposure. a. Representative retinal autofluorescence images with bright spots correlated with retinal damage. b. SLO autofluorescence images were further analyzed for statistical analysis (Means±SEM; compared to DMSO control, * p<0.01).

Figure 21:
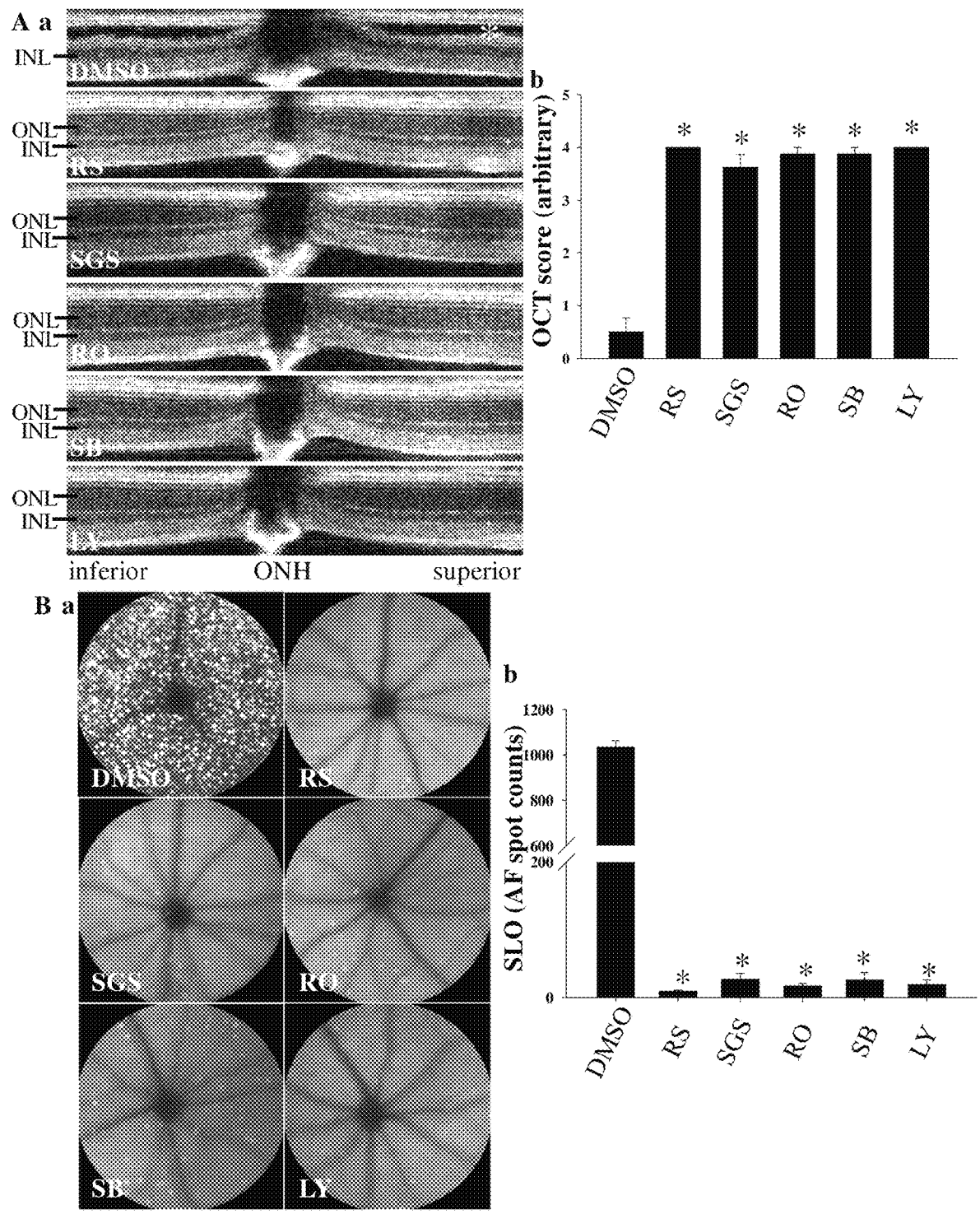

FIGS. 21(A-B) illustrate multiple pharmacological compounds antagonizing Gs-couple GPCRs render retinas resistant to light-induced damage. RS 23579-190 (RS), a 5-HT4R antagonist, SGS 518 oxalate (SGS) and RO 04-6790 (RO), selective 5-HT6R antagonists, SB 269970 (SB) and LY-215840 (LY), 5-HT7R antagonists, together with DMSO vehicle control, was each administered to 4- to 5-week old Abca4$^{-/-}$Rdh8$^{-/-}$ mice through intraperitoneal injection prior to white light exposure at the intensity of 10,000 Lux for 30 min. (A) The effect of each treatment aforementioned was examined by OCT imaging 7 days after light exposure. a. Representative OCT images: * indicates disrupted photoreceptor structure; ONH, optic nerve head; ONL, outer nuclear layer; INL inner nuclear layer. b. OCT scores after statistical analysis (Means±SEM; compared to DMSO control, * p<0.01). (B) SLO imaging was performed 8 days after light exposure. a. Representative retinal autofluorescence images. b. The number of retinal autofluorescence spots were counted and followed by statistical analysis (Means±SEM; compared to DMSO control, p<0.01).

Figure 22:
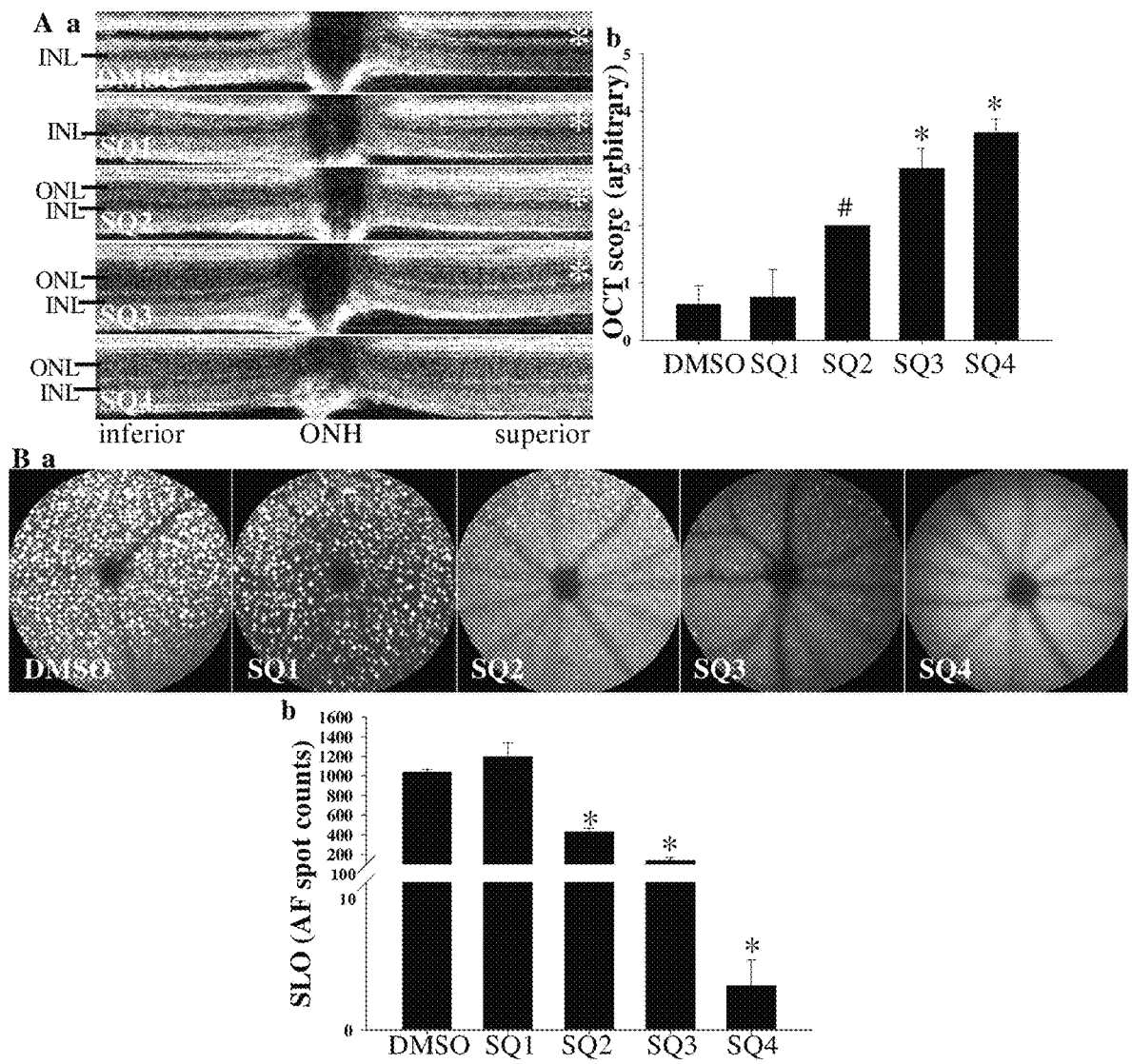

FIGS. 22(A-B) illustrate adenylyl cyclase inhibitor dose-dependently protects retina against light-induced damage in Abca4$^{-/-}$Rdh8$^{-/-}$ mouse. Adenylyl cyclase inhibitor SQ 22536 (SQ) was given to 4- to 5-week old Abca4$^{-/-}$Rdh8$^{-/-}$ mice at various doses through intraperitoneal injection prior to white light exposure at the intensity of 10,000 Lux for 30 min. SQ1: 0.083 mg/Kg; SQ2: 0.125 mg/Kg; SQ3: 0.25 mg/Kg; SQ4: 0.5 mg/Kg. (A) The effect of SQ treatment was assessed by OCT imaging 7 days after light exposure. a. OCT images: * indicates damaged photoreceptor structure; ONH, optic nerve head; ONL, outer nuclear layer; INL inner nuclear layer. b. Statistical analysis of OCT scores (Means±SEM; compared to DMSO control, # p<0.05; * p<0.01). (B) Retinal autofluorescence was examined by SLO imaging 8 days after light exposure. a. Representative retinal autofluorescence images with bright spots correlated with retinal damage. b. Statistical analysis of the number of SLO autofluorescence spots (Means±SEM; compared to DMSO control, * p<0.01).

Figure 23:
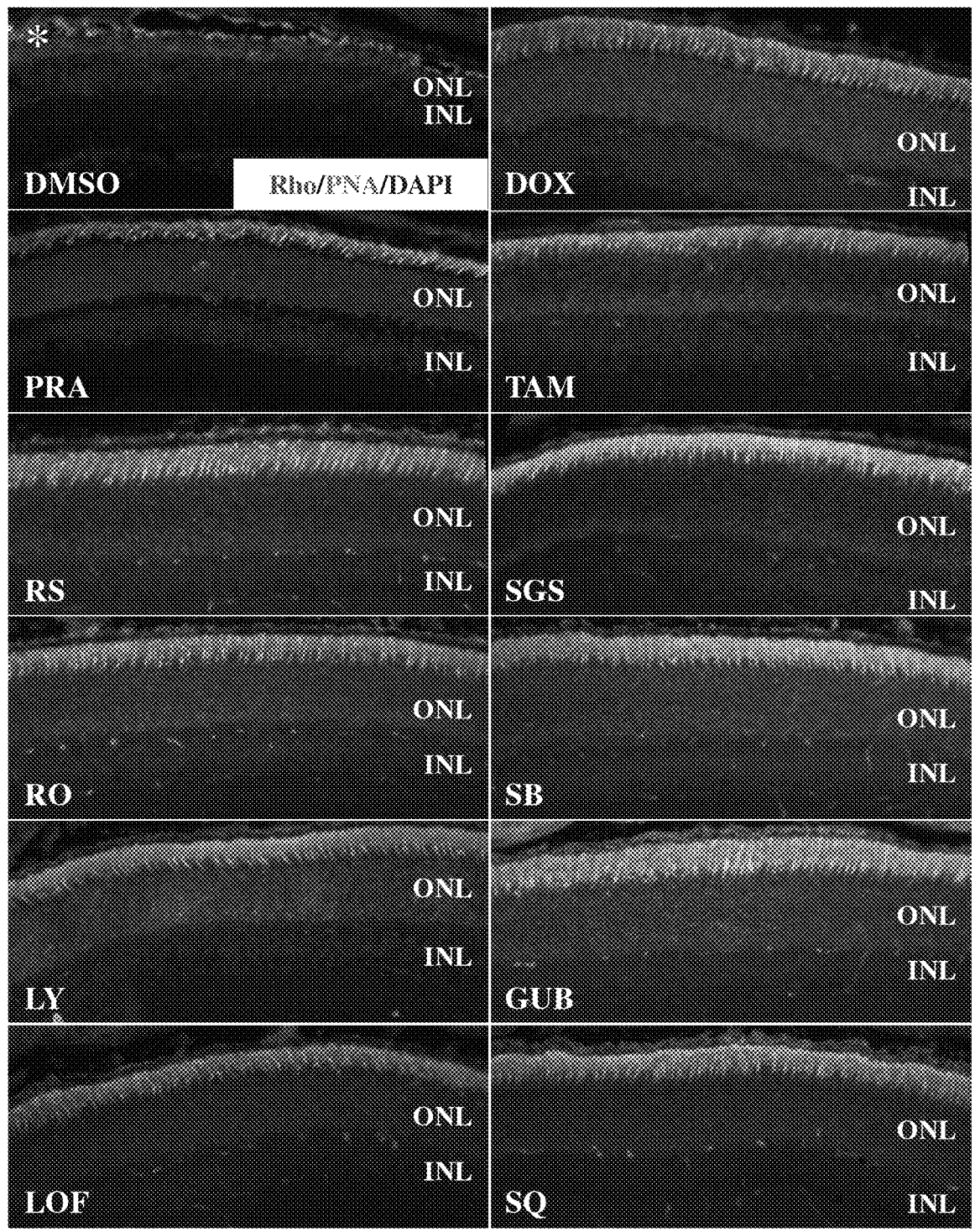

FIG. 23 illustrates retinal immunohistochemical examination validates the therapeutic effects of treatment targeting Gq, Gs, Gi-coupled GPCRs and adenylyl cyclase. Retinal morphological changes after various indicated treatment was further evaluated by photoreceptor immunohistochemical examination (* indicates severely impaired photoreceptor outer segment and inner segment indicated by residual expression of Rhodopsin and peanut agglutinin; ONL, outer nuclear layer; INL inner nuclear layer; Rho: rhodopsin in red, PNA, peanut agglutinin in green and DAPI in blue; 20× objective lens).

FIG. 24 illustrates retinal function is preserved by treatment targeting Gq, Gs, Gi-coupled GPCRs and adenylyl cyclase. ERG was performed to evaluate retinal function in Abca4$^{-/-}$Rdh8$^{-/-}$ mice 2 weeks after they were pretreated with indicated pharmacological agents. Compared to Abca4$^{-/-}$Rdh8$^{-/-}$ mice without being exposed to bright light (No light), Abca4$^{-/-}$Rdh8$^{-/-}$ mice with light exposure at 10,000 lux for 30 min and treated by DMSO vehicle control (DMSO) displayed significantly impaired retinal function as indicated by decreased scotopic a-wave and b-wave amplitude. Compounds exhibiting protective effect against light-induced retinal dysfunction included: DOX, RS, RO, LY, LOF and SQ. A. Representative scotopic a-, b-waves. B. Plotted data of scotopic ERG.

Figure 25:
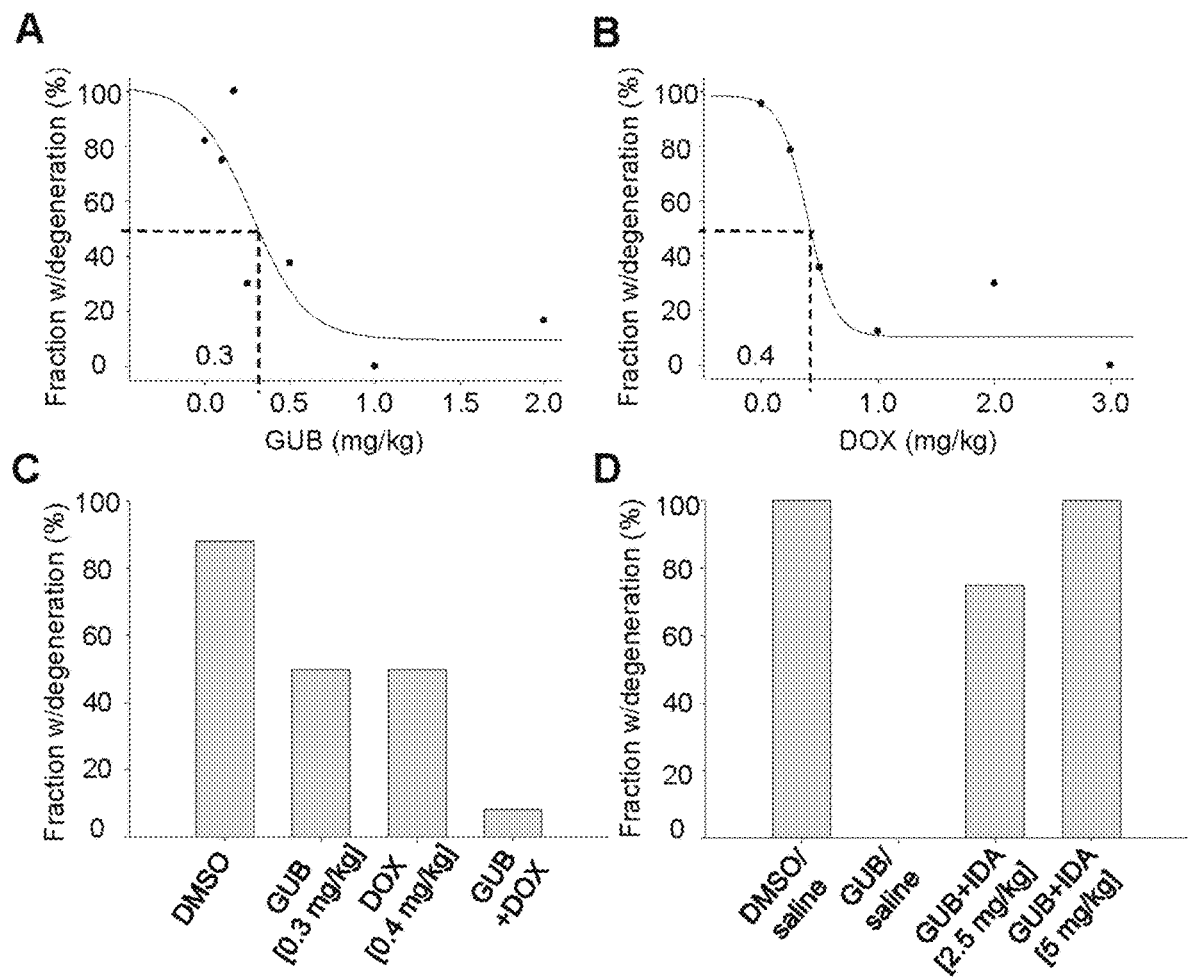

FIGS. 25(A-D) illustrate contributions of Gi and Gq pathways to light-induced retinal pathogenesis. (A) Guanabenz (GUB), a Gi pathway activator, protected Abca4$^{-/-}$ Rdh8$^{-/-}$ mouse retinas from bright light-induced degeneration in a dose-dependent fashion with a half maximal effective dose determined as 0.3 mg/kg. n≥for each data point. (B) The Gq pathway inhibitor, doxazosin (DOX), also protected mouse retinas from bright light-induced degeneration in a dose-dependent fashion with a half maximal effective dose of 0.4 mg/kg. n>5 for each data point. (C) The combination of GUB at 0.3 mg/kg BW and DOX at 0.4 mg/kg BW, protected the retina in at least an additive manner, n≥5. (D) Idazoxan (IDA) at 2.5 mg/kg BW and 5 mg/kg BW, counteracted the protective action of GUB at 2 mg/kg BW, on bright light-induced retinal degeneration, n≥5.

Figure 26:
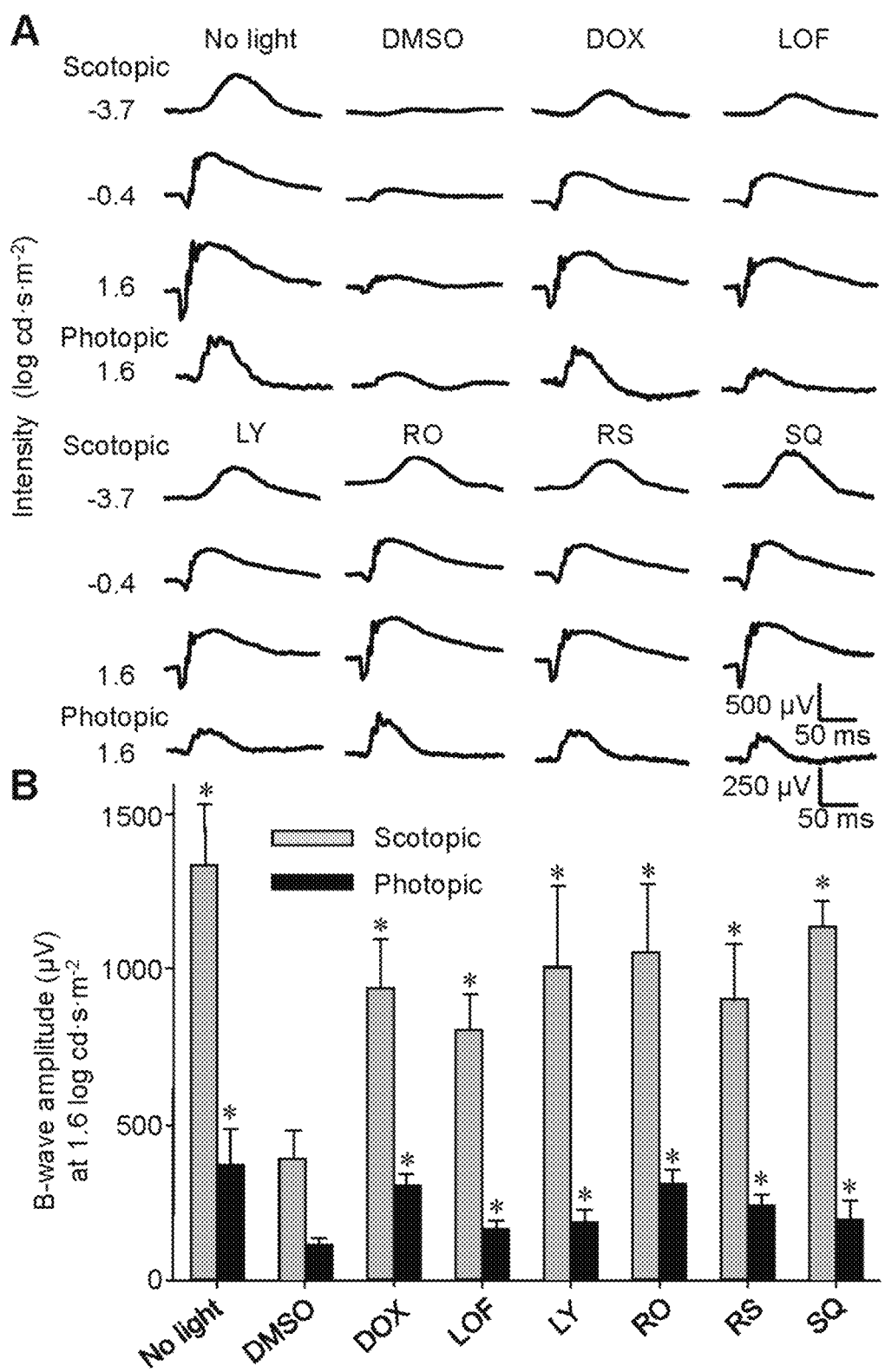

FIGS. 26(A-B) illustrate therapeutics targeting Gq-, Gs-, Gi-coupled GPCRs and AC preserve retinal function in Abca4$^{-/-}$Rdh8$^{-/-}$ mice. Abca4$^{-/-}$Rdh8$^{-/-}$ mice at 4- to 5-weeks of age were exposed to 10,000 lux light for 30 min after pre-treatment with the pharmacological agents at indicated doses, DOX (10 mg/kg BW), LOF (2 mg/kg BW), LY (10 mg/kg BW), RO (30 mg/kg BW), RS (20 mg/kg BW) and SQ (0.5 mg/kg BW). ERGs were recorded to evaluate the effects of these agents on retinal function 2 weeks after light exposure. (A) ERG responses were compared between mice unexposed to intense light (no light), vehicle only (DMSO) and tested agents under both scotopic and photopicconditions. Amplitudes of b-waves at 1.6 log cd·s·m$^{-2}$ under scotopic and photopic conditions are shown (B). Tested compounds showed significant protective effects compared to DMSO-treated mice which displayed significantly impaired retinal function indicated by decreased ERG amplitudes, *(p<0.05). Bars indicate SDs. n=4-6 eyes per group.

Figure 27:
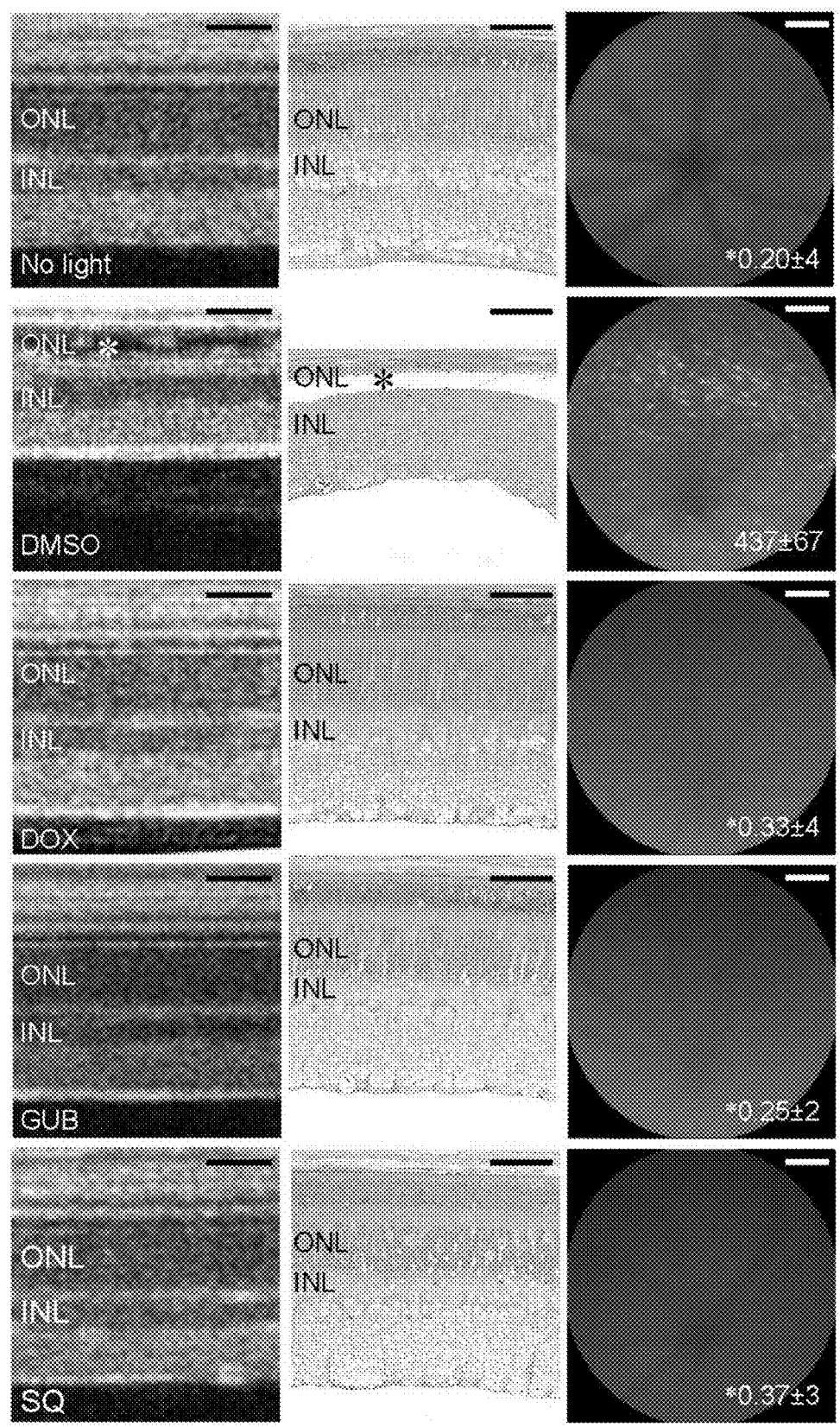

FIG. 27 illustrates Doxazosin (DOX), guanabenz (GUB) and SQ 22536 (SQ) each prevent light-induced retinal degeneration in WT mice. The α1-AR antagonist, DOX; the α2-AR agonist, GUB; or the AC inhibitor, SQ were given to 4-week-old WT (BALB/c) mice by intraperitoneal injection 30 min prior to white light exposure at 10,000 lux for 1 h. BALB/c mice were used to reduce absorption of light by the RPE pigment. Doses of each compound were as follows: DOX; 10 mg/kg; GUB, 2.0 mg/kg; and SQ, 0.5 mg/kg. Effects of these compounds were evaluated by SD-OCT imaging 7 days after light exposure. Representative images of SD-OCT 500 μm away from optic nerve head in the superior retina are shown in the left column. Asterisks indicate damaged photoreceptor structures evident only in DMSO-treated control mice. Retinal cross section images of plastic sections (middle panels) were obtained from areas similar to those used for the OCT images Retinal autofluorescence also was examined by SLO 7 days after light exposure (right panels). Numbers (means±SEM) of bright spots are indicated at the right bottom of SLO images. ONL, outer nuclear layer; INL, inner nuclear layer. Scale bars indicate 50 μm.

Figure 28:
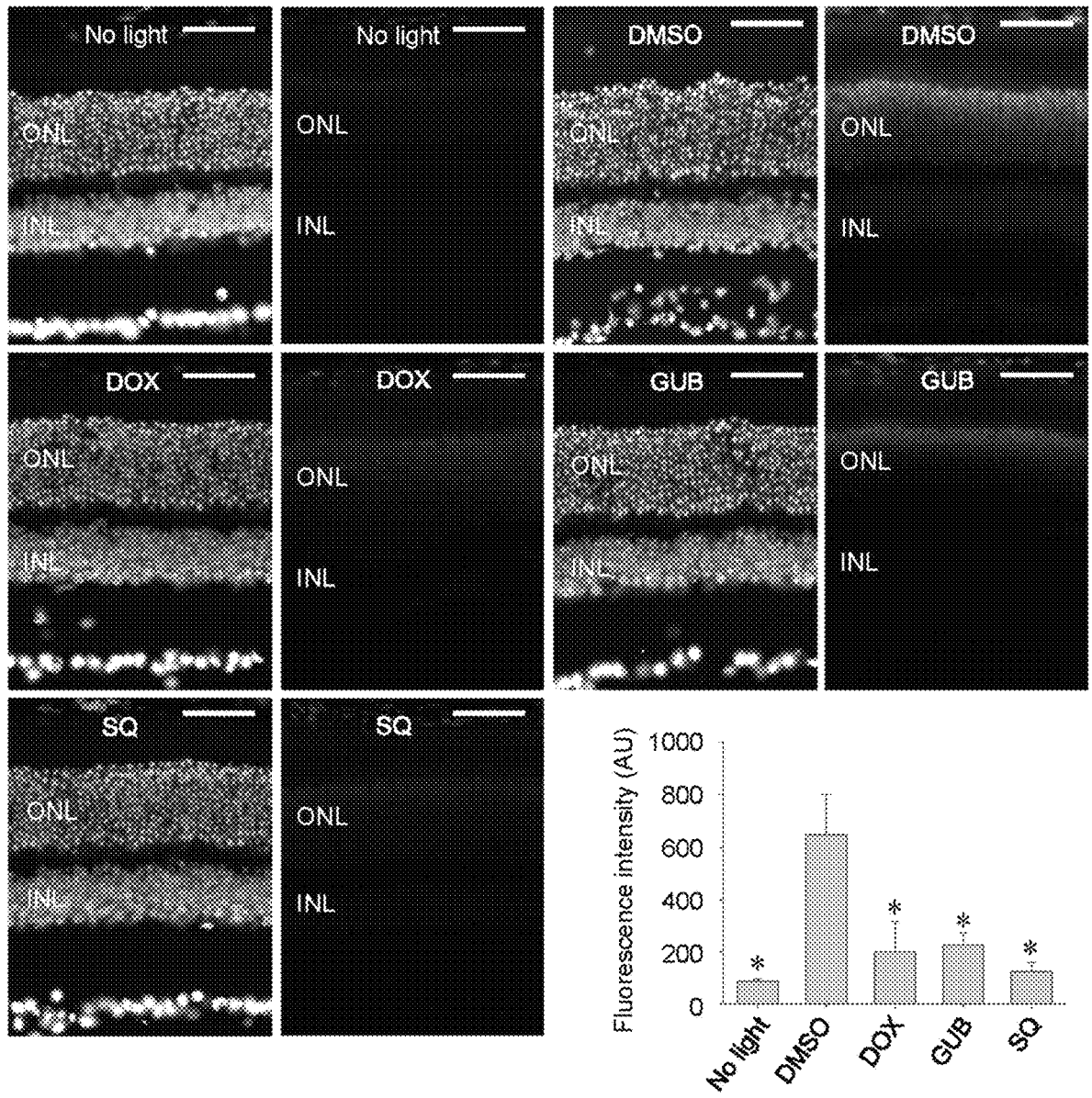

FIG. 28 illustrates ROS generation in photoreceptors of Abca4$^{-/-}$Rdh8$^{-/-}$ mice after bright light exposure is decreased by either doxazosin (DOX), guanabenz (GUB) or SQ 22536 (SQ) pre-treatment. Dark-adapted pigmented Abca4$^{-/-}$Rdh8$^{-/-}$ mice at the age of 4-5 weeks were treated with the ROS probe, DHE, 1 h prior to light exposure at 10,000 lux for 30 min. Either vehicle control (DMSO), and DOX, GUB or SQ were also administered by intraperitoneal injection 30 min prior to light exposure. Dose of each compound was as follows: DOX, 10 mg/kg; GUB, 2.0 mg/kg; SQ, 0.5 mg/kg. Dark-adapted Abca4$^{-/-}$Rdh8$^{-/-}$ mice unexposed to light were included for DHE probe treatment as well (no light). Retinas were harvested 3 h after illumination. ROS signals were obtained with the identical exposure setup under a fluorescence microscope (right panel of each image set). DAPI staining was performed as well to visualize cell nuclei and gross retinal structure (left panel of each image set). Recorded ROS fluorescence intensity in arbitrary units averaged from various areas was further analyzed and summarized for group comparisons (means±SEM). ONL, outer nuclear layer; INL, inner nuclear layer. *p<0.05. Scale bars indicate 50 μm.

FIGS. 29(A-K) illustrate detection and quantification of doxazosin (DOX), guanabenz (GUB), and SQ 22536 (SQ) in mouse eye. (A) HPLC separation of SQ (peak 1), clenbuterol (internal standard, IS) (peak 2), and GUB (peak 3). (B) (C) (D) MS and MS patterns for SQ, clenbuterol, and GUB, respectively. Characteristic fragmentation profiles were used to design the selected reaction monitoring-based detection and quantification method. (E) Elution profile of parazosin (IS) (peak 1) and DOX (peak 2). (F) (G) MS and MS$^2$ fragmentation pattern for parazosin and DOX. (H) Relationships between ion intensities and molar ratio for drug/internal standard pairs (DOX/parazosin (filled triangles), GUB/clenbuterol (filled circles), and SQ/clenbuterol (open circles)) which were used for IS-based drug quantification. (I) (J) (K) Representative chromatograms of the eye extract indicating the presence of DOX, GUB, and SQ, respectively. Black chromatograms correspond to ion intensities of SRM transitions characteristic for the tested drugs. Gray lines represent ion intensities for the internal standards. Letters "T" and "C" discriminate between samples obtained from drug-treated mice (T) and control, non-treated animals (C).

FIGS. 30(A-B) illustrate GPCR-targeted therapeutics prevent formation of large fluorescent granules in the RPE of Abca4$^{-/-}$Rdh8$^{-/-}$ mice (6-7 weeks of age) after exposure to bright light. (A) Representative TPM images of the RPE 10 days after exposure to bright light. Upper left panel, unexposed to light (No light) control; upper right panel, exposed to bright light (Bleached) and DMSO treated control; lower left panel, pre-treated with prazosin (PRA); lower right panel, pre-treated with guanabenz (GUB). Cross-sections shown at the right edge and at the bottom of each en-face RPE image reveal that fluorescent granules, most pronounced in the bleached DMSO treated control, extend across the whole thickness of the RPE and into the outer retina-photoreceptor space. Scale bars indicate 25 μm. (B) Emission spectra after excitation with 730 nm light (left panel) and after excitation with 850 nm light (right panel). The spectra from exposed to light, DMSO-treated control are notably red-shifted for both excitation wavelengths.

DETAILED DESCRIPTION

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

It will be noted that the structure of some of the compounds of the application include asymmetric (chiral) carbon atoms. It is to be understood accordingly that the isomers arising from such asymmetry are included within the scope of the invention, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" refers to compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not minor images of one another are termed "diastereoisomers", and stereoisomers that are non-superimposable mirror images are termed "enantiomers", or sometimes optical isomers. A carbon atom bonded to four nonidentical substituents is termed a "chiral center".

The term "chiral isomer" refers to a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n–1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Cahn, J., Chem. Educ. 1964, 41, 116).

The term "geometric isomers" refer to the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative", refers to compounds that have a common core structure, and are substituted with various groups as described herein. For example, all of the compounds represented by formula I are primary amines and have formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" refer to modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" refers to inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" refers to stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term a "pharmaceutical composition" refers to a formulation containing the disclosed compounds in a form suitable for administration to a subject. The pharmaceutical composition can be in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intraocular, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" refers to a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" refers to pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated within the scope of the claims.

The phrase "pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of salts are found in Remington's Pharmaceutical Sciences, 18th ed. (Mack Publishing Company, 1990). For example, salts can include, but are not limited to, the hydrochloride and acetate salts of the aliphatic amine-containing, hydroxyl amine-containing, and imine-containing compounds of the present invention.

It should be understood that all references to pharmaceutically acceptable salts include solvent addition forms (solvates) or crystal forms (polymorphs) as defined herein, of the same salt.

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present application is intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs the present invention are prepared by modifying functional groups present in the compound in such a way that the modifications are cleaved, either in routine manipulation or in vivo, to the parent compound. Prodrugs include compounds described herein wherein a hydroxy, amino, sulfhydryl, carboxy, or carbonyl group is bonded to any group that may be cleaved in vivo to form a free hydroxyl, free amino, free sulfadryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of Formula I, and the like (e.g., Bundegaard, H. "Design of Prodrugs" p 1-92, Elesevier, New York-Oxford (1985)).

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, $2^{nd}$ ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" refers to a functional group that converts an amine, amide, or other nitrogen-containing moiety into a different chemical group that is substantially inert to the conditions of a particular chemical reaction. Amine protecting groups can be removed easily and selectively in good yield under conditions that do not affect other functional groups of the molecule. Examples of amine protecting groups include, but are not limited to, formyl, acetyl, benzyl, t-butyldimethylsilyl, t-butdyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl)ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Other amine protecting groups can be identified by those of skill in the art.

Representative hydroxy protecting groups include those where the hydroxy group is either acylated or alkylated, such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" refers to solvent addition forms that contain either stoichiometric or non stoichiometric amounts of solvent. Some compounds have a tendency to trap a fixed molar ratio of solvent molecules in the crystalline solid state, thus forming a solvate. If the solvent is water, the solvate formed is a hydrate; when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

A "patient," "subject," or "host" to be treated by the subject method may mean either a human or non-human animal, such as primates, mammals, and vertebrates.

The term "prophylactic or therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" refer to molecules and other agents that are biologically, physiologically, or pharmacologically active substances that act locally or systemically in a patient or subject to treat a disease or condition, such as retinal degeneration or other forms of retinal disease whose etiology involves light induced retinal degeneration or aberrant clearance of all trans-retinal. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" is an art-recognized term. In certain embodiments, the term refers to an amount of a therapeutic agent that, when incorporated into a polymer, produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" refer to the dose of a drug, which produces 50% of its maximum response or effect, or alternatively, the dose, which produces a pre-determined response in 50% of test subjects or preparations. The term "LD50" refers to the dose of a drug, which is lethal in 50% of test subjects. The term "therapeutic index" refers to the therapeutic index of a drug, defined as LD50/ED50.

The term "substituted," as used herein, means that any one or more hydrogens on the designated atom is replaced with a selection from the indicated group, provided that the designated atom's normal valency is not exceeded, and that the substitution results in a stable compound. When the substituent is keto (i.e., =O), then 2 hydrogens on the atom are replaced. Ring double bonds, as used herein, are double bonds that are formed between two adjacent ring atoms (e.g., C=C, C=N, or N=N).

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons. As used herein, "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

As used herein, "alkenyl" is intended to include hydrocarbon chains of either straight or branched configuration having one or more carbon-carbon double bonds occurring at any stable point along the chain. For example, $C_{2-6}$ alkenyl is intended to include $C_2$, $C_3$, $C_4$, $C_5$, and $C_6$ alkenyl groups. Examples of alkenyl include, but are not limited to, ethenyl and propenyl.

As used herein, "alkynyl" is intended to include hydrocarbon chains of either straight or branched configuration having one or more carbon-carbon triple bonds occurring at any stable point along the chain. For example, $C_{2-6}$ alkynyl is intended to include $C_2$, $C_3$, $C_4$, $C_5$, and $C_6$ alkynyl groups. Examples of alkynyl include, but are not limited to, ethynyl and propynyl.

Furthermore, "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams such as azetidinones and pyrrolidinones, sultams, and sultones. Heterocyclic groups such as pyrrole and furan can have aromatic character. They include fused ring structures such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

As used herein, "halo" or "halogen" refers to fluoro, chloro, bromo, and iodo. "Counterion" is used to represent a small, negatively charged species, such as fluoride, chloride, bromide, iodide, hydroxide, acetate, and sulfate.

"Stable compound" and "stable structure" are meant to indicate a compound that is sufficiently robust to survive isolation, and as appropriate, purification from a reaction mixture, and formulation into an efficacious therapeutic agent.

"Free compound" is used herein to describe a compound in the unbound state.

"Extinction coefficient" is a constant used in the Beer-Lambert Law which relates the concentration of the substance being measured (in moles) to the absorbance of the substance in solution (how well the substance in solution blocks light beamed through it from getting out on the other side). It is an indicator of how much light a compound absorbs at a particular wavelength.

In the specification, the singular forms also include the plural, unless the context clearly dictates otherwise. Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

"Small molecule" refers to a molecule, which has a molecular weight of less than about 2000 amu, or less than about 1000 amu, and even less than about 500 amu.

All percentages and ratios used herein, unless otherwise indicated, are by weight.

The term "retina" refers to a region of the central nervous system with approximately 150 million neurons. It is located at the back of the eye where it rests upon a specialized epithelial tissue called retinal pigment epithelium or RPE. The retina initiates the first stage of visual processing by transducing visual stimuli in specialized neurons called "photoreceptors". Their synaptic outputs are processed by elaborate neural networks in the retina and then transmitted to the brain. The retina has evolved two specialized classes of photoreceptors to operate under a wide range of light conditions. "Rod" photoreceptors transduce visual images under low light conditions and mediate achromatic vision. "Cone" photoreceptors transduce visual images in dim to bright light conditions and mediate both color vision and high acuity vision.

Every photoreceptor is compartmentalized into two regions called the "outer" and "inner" segment. The inner segment is the neuronal cell body containing the cell nucleus. The inner segment survives for a lifetime in the absence of retinal disease. The outer segment is the region where the light sensitive visual pigment molecules are concentrated in a dense array of stacked membrane structures. Part of the outer segment is routinely shed and regrown in a diurnal process called outer segment renewal. Shed outer segments are ingested and metabolized by RPE cells.

The term "macula" refers to the central region of the retina, which contains the fovea where visual images are processed by long slender cones in high spatial detail ("visual acuity"). "Macular degeneration" is a form of retinal neurodegeneration, which attacks the macula and destroys high acuity vision in the center of the visual field. AMD can be in a "dry form" characterized by residual lysosomal granules called lipofuscin in RPE cells, and by extracellular deposits called "drusen". Drusen contain cellular waste products excreted by RPE cells. "Lipofuscin" and drusen can be detected clinically by ophthalmologists and quantified using fluorescence techniques. They can be the first clinical signs of macular degeneration.

Lipfuscin contains aggregations of A2E. Lipofuscin accumulates in RPE cells and poisons them by multiple known mechanisms. As RPE cells become poisoned, their biochemical activities decline and photoreceptors begin to degenerate. Extracellular drusen may further compromise RPE cells by interfering with their supply of vascular nutrients. Drusen also trigger inflammatory processes, which leads to choroidal neovascular invasions of the macula in one patient in ten who progresses to wet form AMD. Both the dry form and wet form progress to blindness.

The term "ERG" is an acronym for electroretinogram, which is the measurement of the electric field potential emitted by retinal neurons during their response to an experimentally defined light stimulus. ERG is a non-invasive measurement, which can be performed on either living subjects (human or animal) or a hemisected eye in solution that has been removed surgically from a living animal.

The term "RAL" means retinaldehyde. "Free RAL" is defined as RAL that is not bound to a visual cycle protein. The terms "trans-RAL" and "all-trans-RAL" are used interchangeably and mean all-trans-retinaldehyde.

Embodiments described herein relate to compounds and methods of treating an ocular disorder in a subject associated with light induced retinal degeneration, aberrant all-trans-retinal clearance and/or reactive oxygen species (ROS) generation in the retina. The ocular disorder can include, for example, retinal disorders, such as retinal degeneration, geographic atrophy (GA), macular degeneration, including age-related macular degeneration, Stargardt disease, and retinitis pigmentosa.

Figure 1:
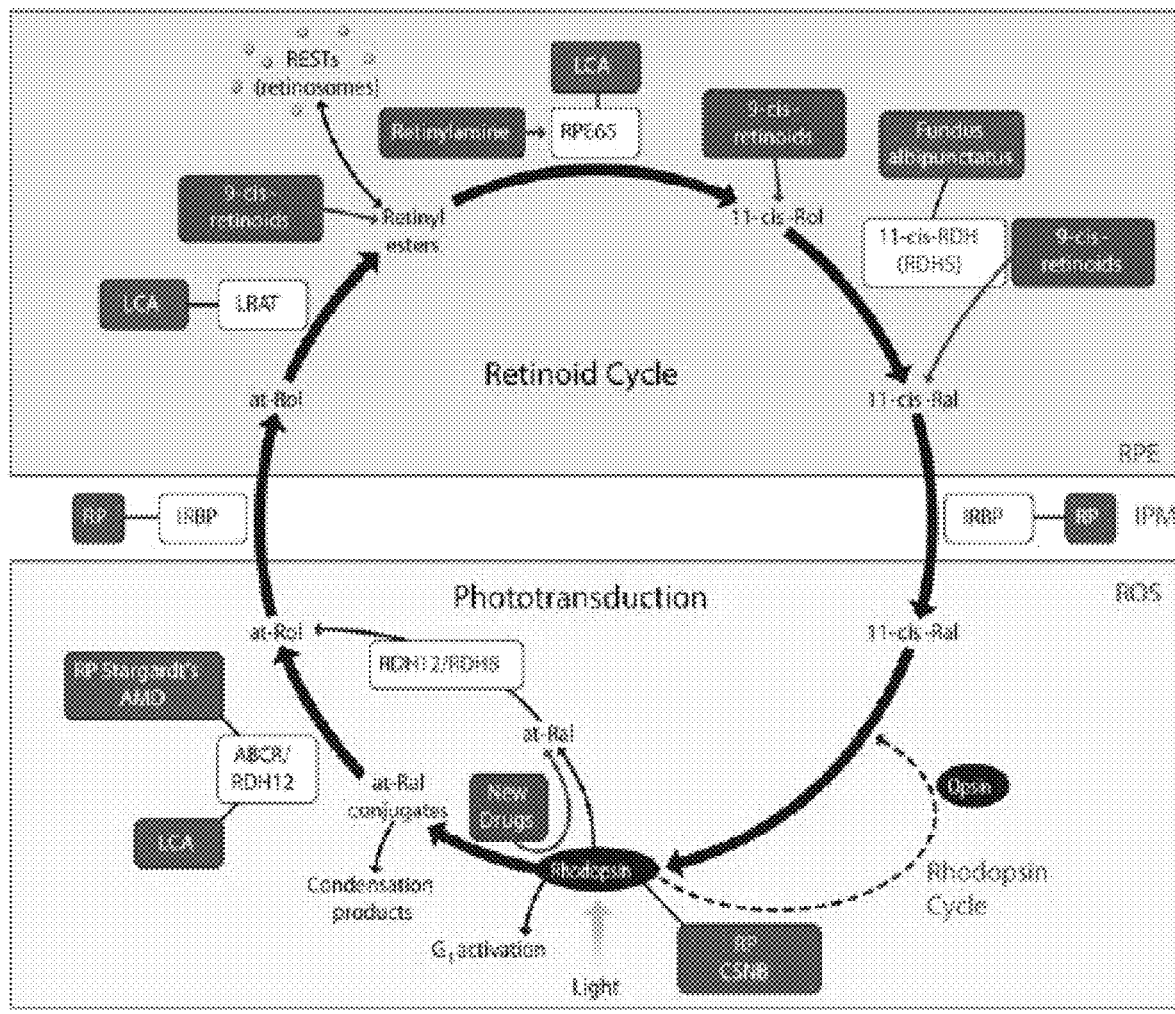
FIG. 1 is a schematic illustration of the visual cycle.
Figure 2:
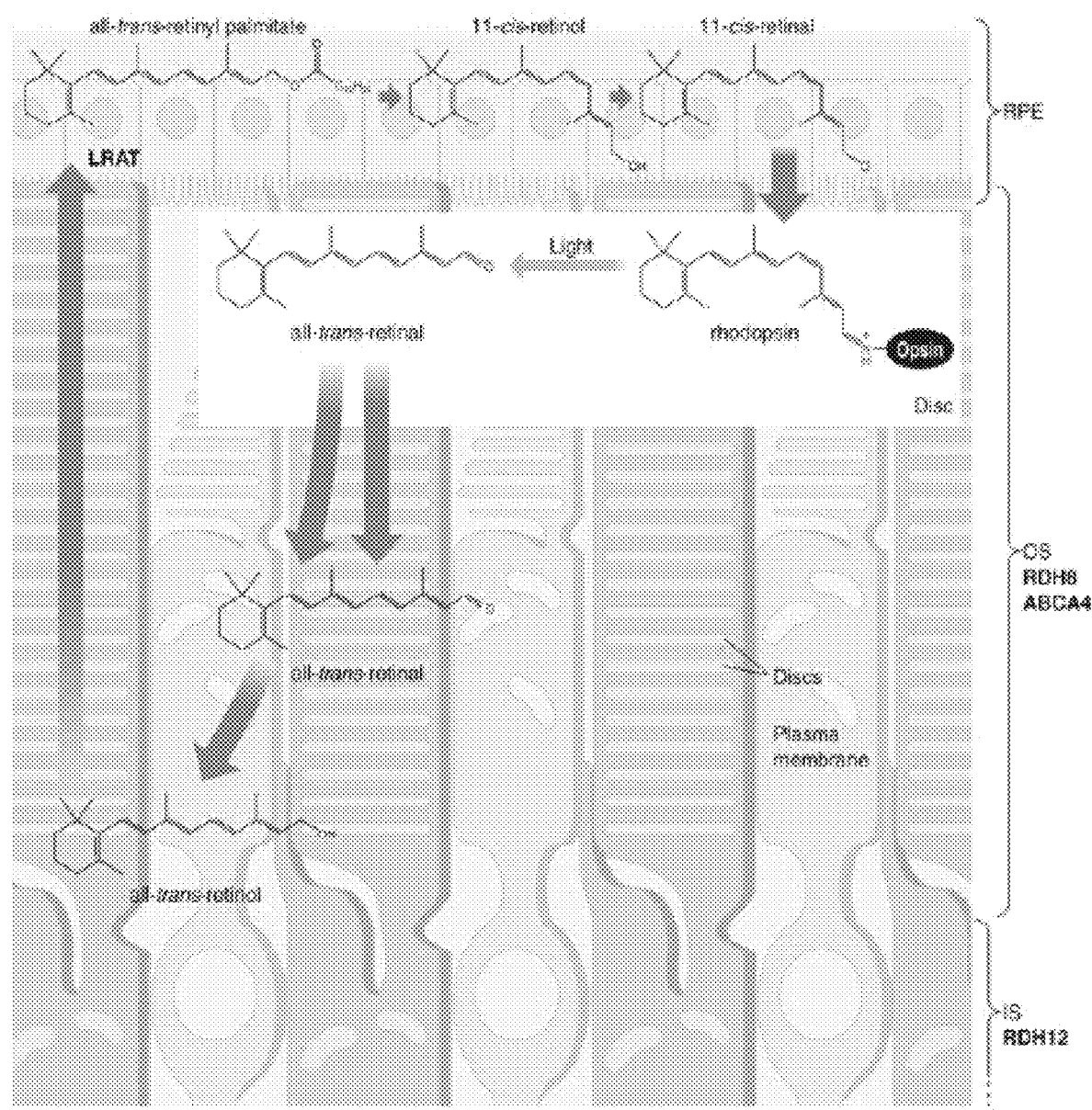
FIG. 2 is a schematic illustration of retinoid flow and all-trans-retinal clearance in the visual cycle.

FIGS. 1 and 2 show the retinoid flow in the visual cycle including condensation of all-trans-RAL, and all-trans-RAL clearance. After 11-cis-retinal binds to opsin from rhodopsin, the resulting visual chromophore 11-cis-retinylidene is photoisomerized to all-trans-retinylidene, the precursor or all-trans-RAL that is later released. Most of the all-trans-RAL dissociates from opsin into the cytoplasm before it is reduced to all-trans-retinol by RDHs including RDH8. The fraction of all-trans-RAL that dissociates into disc lumens is transported by ABCA4 before it is reduced. Thus, condensation products can be generated both within the disc lumens and the cytoplasm before it is reduced.

Figure 3:
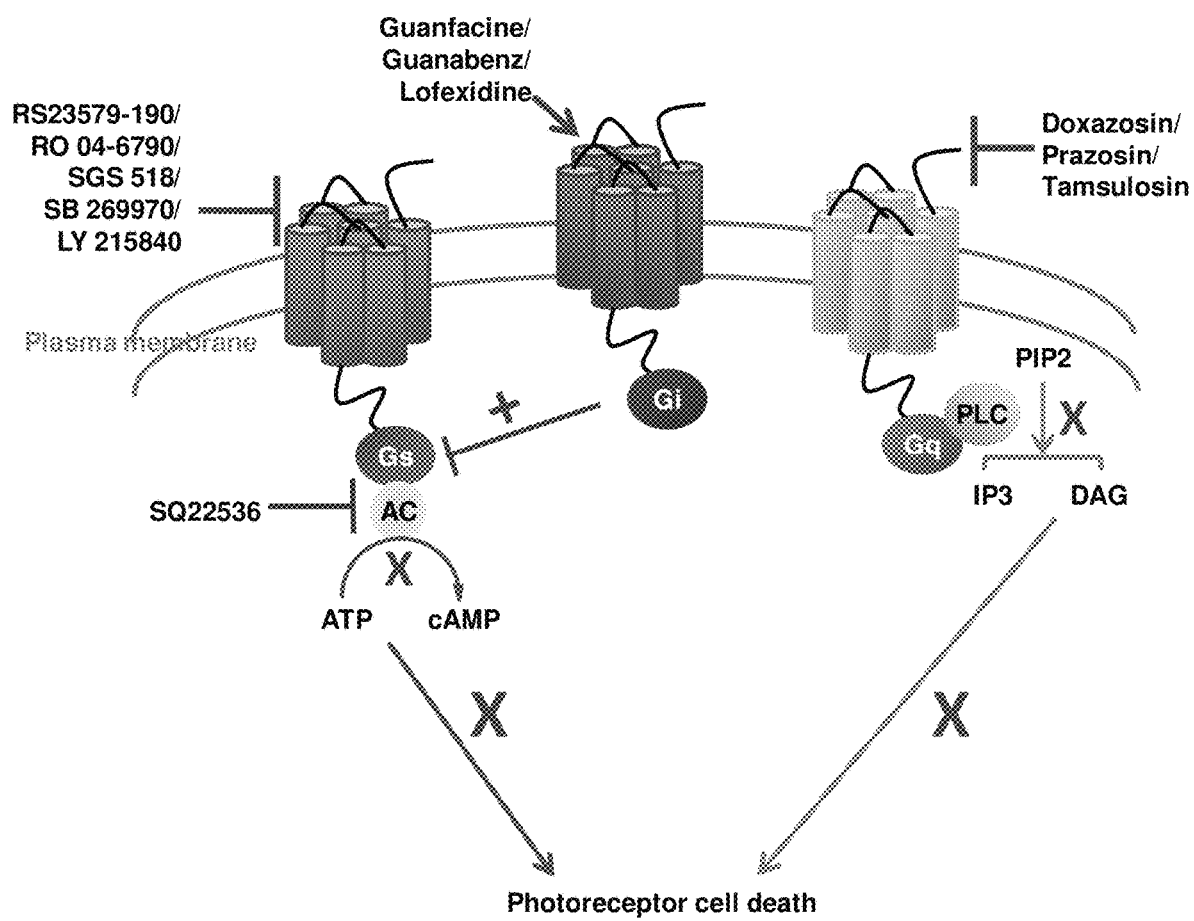
FIG. 3 is a schematic illustration of strategies targeting multiple GPCRs for therapeutic treating of photoreceptor degeneration.
Figure 4:
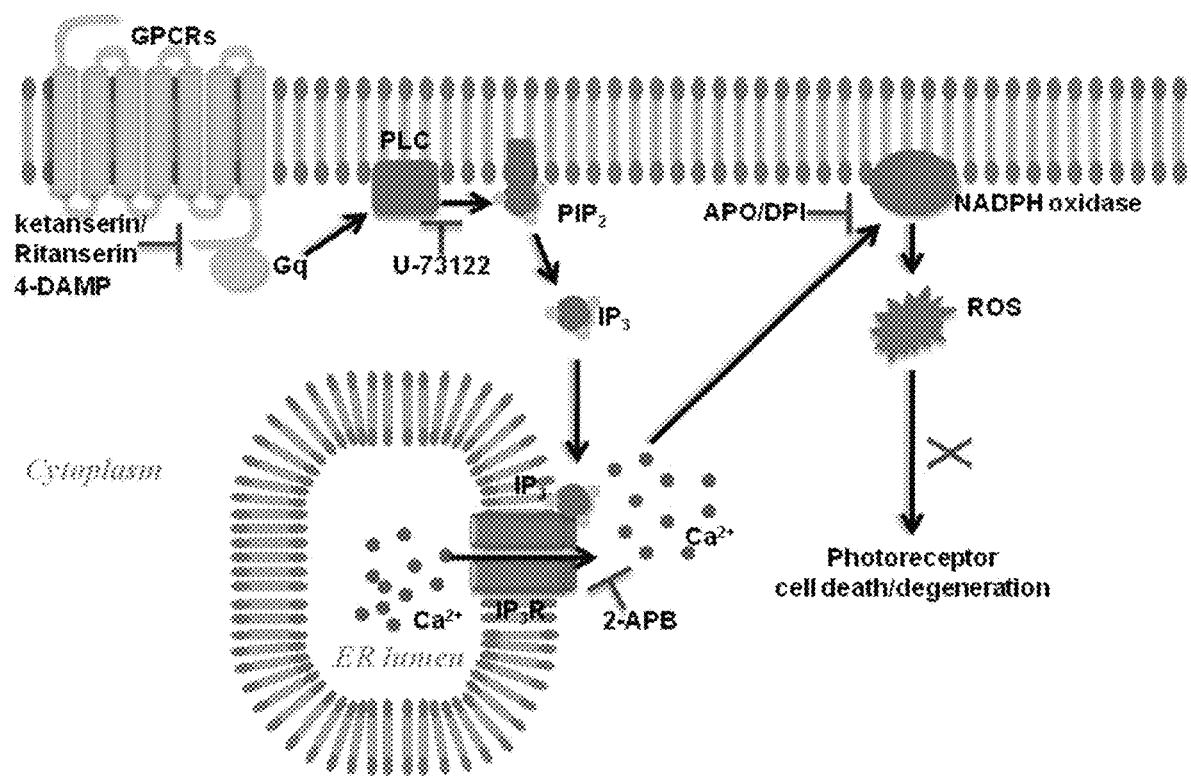
FIG. 4 is a schematic illustration of the phospholipase signaling pathway and targets for agents.

It was found that all-trans-RAL that has escaped sequestering by opsins in photoreceptor outer segments of the retina is toxic to retina cells and that aberrant all-trans-RAL clearance from the inner disc membrane to the outer disc membrane can cause retinal degeneration. As illustrated in FIGS. 3 and 4, aberrant all-trans-retinal clearance from the retina can trigger the activation of the Gs and Gq protein-coupled receptors, such as serotonin receptors (e.g., $5\text{-HT}_{2a}$ receptor, $5\text{-HT}_{2b}$ receptor, $5\text{-HT}_{2c}$ receptor, $5\text{-HT}_{2a/c}$ receptor, $5\text{-HT}_4$ receptor, $5\text{-HT}_6$ receptor, and $5\text{-HT}_7$ receptor), alpha-1 adrenergic receptors, H1 histamine receptor, or $M_3$ muscarinic receptor ($M_3R$), and pathways associated with Gs and Gq activation.

Increased functionality or activity of Gs-coupled GPCRs and subsequent activation of adenylyl cyclase (AC) was found to cause photoreceptor cell death. On the other hand, Gi-coupled GPCRs functionally lead to suppression of AC activity. Agonists activating α2 adrenergic receptor, a Gi-coupled GPCR, prevented photoreceptor death. Therefore, AC as the central player mediating Gs-coupled and Gi-coupled GPCR signaling, can serve as therapeutic target to preserve photoreceptors during degeneration, which could be achieved by inhibition of AC activity by an AC inhibitor.

In addition, activation of Gq-coupled GPCRs leads to the activation of phospholipase C (PLC), which in turn cleaves phosphatidylinositol 4,5-bisphosphate ($PIP_2$), into diglyceride (DAG) and inositol triphosphate ($IP_3$). Subsequently, $IP_3$ binds to its receptor, inositol triphosphate receptor ($IP_3R$) located on the endoplasmic reticulum (ER). This binding triggers the release of $Ca^{2+}$ from the ER and leads to the increased production of ROS by NADPH oxidase. The ROS generated via this signaling cascade is a major cause of retinal degeneration and ocular disorders.

Agents that inhibit and/or antagonize activation of the Gs- or Gq-protein coupled receptors or the Gs- or Gq-signaling cascade, which is induced or triggered by light induced all-trans-retinal generation, can therefore inhibit ROS generation and treat retinal disorders associated with light induced retinal degeneration or all-trans-retinal accumulation. In embodiments described herein, agents used to treat an ocular disorder associated with light induced retinal degeneration, aberrant all-trans-RAL clearance and/or ROS production can include those agents that can inhibit and/or antagonize Gs- or Gq-protein coupled receptor activation, inhibit and/or antagonize the Gq signaling cascade (e.g., agents that inhibit or antagonize PLC activation, $IP_3$ binding to its receptor), inhibit or antagonize the Gs signaling cascade (e.g., agents that inhibit and/or antagonize andenylyl cyclase activation) and/or agents that activate Gi signaling cascade in a retinal cell). These agents can be used alone and/or in combination with each other as well as with other agents to treat retinal disorders associated with light induced retinal degeneration, all-trans-retinal accumulation, and/or ROS production.

In some embodiments, agents used to treat an ocular disorder associated with light induced retinal degeneration, aberrant all-trans-RAL clearance and/or ROS production can include Gs or Gq coupled serotonin receptor antagonists, such as $5\text{-HT}_{2a}$ receptor antagonists, $5\text{-HT}_{2b}$ receptor antagonists, $5\text{-HT}_{2c}$ receptor antagonists, $5\text{-HT}_{2a/c}$ receptor antagonists, $5\text{-HT}_4$ receptor antagonists, $5\text{-HT}_6$ receptor antagonists, and $5\text{-HT}_7$ receptor antagonists.

Examples of serotonin receptor antagonists are citalopram, escitalopram, fluoxetine, R-fluoxetine, sertraline, paroxetine, fluvoxamine, venlafaxine, duloxetine, dapoxetine, nefazodone, imipramine, imipramine N-oxide, desipramine, pirandamine, dazepinil, nefopam, befuraline, fezolamine, femoxetine, clomipramine, cianoimipramine, litoxetine, cericlamine, seproxetine, WY 27587, WY 27866, imeldine, ifoxetine, tiflucarbine, viqualine, milnacipran, bazinaprine, YM 922, S 33005, F 98214-TA, OPC 14523, alaproclate, cyanodothepine, trimipramine, quinupramine, dothiepin, amoxapine, nitroxazepine, McN 5652, McN 5707, O177, Org 6582, Org 6997, Org 6906, amitriptyline, amitriptyline N-oxide, nortriptyline, CL 255.663, pirlindole, indatraline, LY 113.821, LY 214.281, CGP 6085 A, RU 25.591, napamezole, diclofensine, trazodone, EMD 68.843, BMY 42.569, NS 2389, sercloremine, nitroquipazine, ademethionine, sibutramine, clovoxamine, desmethylsubitramine, didesmethylsubitramine, clovoxamine vilazodone, N-[(1-[(6-Fluoro-2-napthalenyl)methyl]-4-piperidinyl]amino]carbonyl]-3-pyridine carboxamide, [trans-6-(2-chlorophenyl)-1,2,3,5,6,10b-hexahydropyrrolo-(2,1-a)isoquinol-ine] (McN 5707), (dl-4-exo-amino-8-chloro-benzo-(b)-bicyclo[3.3.1] nona-2-6 alpha (10 alpha)-diene hydrochloride) (Org 6997), (dl)-(5 alpha,8 alpha,9 alpha)-5,8,9,10-Tetrahydro-5,9-methanobenzocycloocten-8-amine hydrochloride (Org 6906), -[2-[4[(6-fluoro-1H-indol-3-yl)-3,6-dihydro-1(2H)-pyridinyl]ethyl]-3-isop-ropyl-6-(methylsulphonyl)-3,4-dihydro-1H-2,1,3-benzothiadiazine-2,2-dioxid-e (LY393558), [4-(5,6-dimethyl-2-benzofuranyl)-piperidine] (CGP 6085), dimethyl-[5-(4-nitro-phenoxy)-6,7,8,9-tetrahydro-5H-benzocyclohepten-7-yl-]amine (RU 25.591), or a pharmaceutically acceptable salt of any of these compounds.

In one embodiment, the serotonin receptor antagonist is selected from agomelatine, pizotifen, RS 23579-190, Ro 04-6790 (4-Amino-N-[2,6-bis(methylamino)-4-pyrimidinyl]benzenesulfonamidev), SGS 518 oxalate (1-methyl-3-(1-methyl-4-piperidyl)indol-5-yl]2,6-difluorobenzenesulfonate; oxalic acid), SB 269970 (3-({(2R)-2-[2-(4-Methyl-1-piperidinyl)ethyl]-1-pyrrolidinyl}sulfonyl)phenol hydrochloride (1:1)), LY 215840 ((8β)—N-[(1S,2R)-2-Hydroxycyclopentyl]-1-isopropyl-6-methylergoline-8-carboxamide), citalopram, escitalopram, fluoxetine, sertraline, paroxetine, fluvoxamine, venlafaxine, duloxetine, dapoxetine, nefazodone, imipramine, femoxetine and clomipramine or a pharmaceutically acceptable salt of any of these compounds.

In other embodiments, the agent can include a $5\text{-HT}_{2a}$ receptor antagonist. Examples of $5\text{-HT}_{2a}$ receptor antagonists are described in U.S. Pat. No. 4,444,778 and can include nefazodone, pizotifen, ketanserin, desipramine, imipramine, chlorimipramine, protriptylene, dibenzepine, amitryptyline, doxepin, prothiadene, pirandamine, spirobenzofuran, ciclazindol, nefopam, deximafen, daledalin, amedalin, quipazine, trazodone, zimelidine, tofenacine, fenetazole and fenflurame. Additional compounds which have $5\text{-HT}_{2a}$ antagonist activity and can be used are 11-amino-1,5-methano-1,2,5,6-tetrahydrobenzocine; 1-methylamino-4-phenyl-1,2,3,4-tetrahydronaphthylene; 6-cyano-1,3-dihydro-3-dimethylaminopropyl-3-(p-fluorophenyl)-isobenzofuran; 4-benzyl-1-(2-benzofurancarbonyl)-piperidide, 1,4-ethano-4-phenyl-cyclohexylamine, α-(p-chlorophenyl)-2-methylaminomethylbenzyl alcohol; α-(2-methylaminoethyl)-2-methoxy or 4-trifluoromethylphenylbenzyl ether or p-anisyl-(1-methyl-4-phenyl-3-pipecolinyl)-ether. Still other examples of $5\text{-HT}_{2a}$ receptor antagonists include piperidinylamino-thieno[2,3-d]pyrimidine compounds described in U.S. Pat. No. 7,030,240 and 1,4-substituted cyclic amine derivatives described in U.S. Pat. No. 7,541,371

In other embodiments, agents used to treat an ocular disorder associated with light induced retinal degeneration, aberrant all-trans-RAL clearance and/or ROS production can include alpha 1 adrenergic antagonists. Examples of alpha 1 adrenergic receptor antagonists that can be used to treat ocular disorders described herein include phentolamine family antagonists, known as imidazolines, alkylating agents such as phenoxybenzamine, or piperazinyl quinazolines.

In specific embodiments, the alpha 1 adrenergic receptor antagonist can include, for example, doxazosin, prazosin, tamsulosin, terazosin and 5-methylurapadil. The syntheses of these compounds are described in U.S. Pat. Nos. 3,511,836, 3,957,786, 4,026,894, 5,798,362, 5,792,767, 5,891,882, 5,959,108, and 6,046,207. Additionally, other alpha 1 adrenergic receptor antagonist are well known in the art. See, for example, Lagu, "Identification of alpha 1A-adrenoceptor selective antagonists for the treatment of benign prostatic hyperplasia", Drugs of the Future 2001, 25(8), 757-765 and Forray et al., 8 Exp. Opin. Invest. Drugs 2073 (1999), hereby incorporated by reference in its entirety, which provide examples of numerous alpha 1 adrenergic receptor antagonists.

In other embodiments, agents used to treat an ocular disorder associated with light induced retinal degeneration, aberrant all-trans-RAL clearance and/or ROS production can include alpha-2 adrenergic receptor agonists that can activate the Gi signaling cascade and inhibit andenylyl cyclase activity. Examples of alpha-2 adrenergic receptor agonists include L-norepinephrine, clonidine, dexmetdetomidine, apraclonidine, methyldopa, tizanidine, brimonidine, xylometazoline, tetrahydrozoline, oxymetazoline, guanfacine, guanabenz, guanoxabenz, guanethidine, xylazine, medetomide, moxonidine, mivazerol, rilmenidine, UK 14,304, B-HT 933, B-HT 920, octopamine or a combination thereof.

Other examples of alpha-2 adrenergic receptor agonists include, but are not limited to amidephrine, amitraz, anisodamine, apraclonidine, cirazoline, detomidine, epinephrine, ergotamine, etilefrine, indanidine, lofexidine, medetomidine, mephentermine, metaraminol, methoxamine, midodrine, naphazoline, norepinephrine, norfenefrine, octopamine, oxymetazoline, phenylpropanolamine, rilmenidine, romifidine, synephrine, talipexole, tizanidine, or a combination thereof.

In still other embodiments, agents used to treat an ocular disorder associated with light induced retinal degeneration, aberrant all-trans-RAL clearance and/or ROS production can include an adenylyl cyclase inhibitor. Examples of adenylyl cyclase inhibitors are 9-tetrahydrofuryl adenine, such as THFA or SQ 22536, 2',5'-dideoxyadenosine, or 9-(cyclopentyl)-adenine.

In another embodiment of the application, the agent can include a M3 receptor antagonist, such as 4-DAMP or tolterodine. Other examples of M3 receptor antagonists are described in U.S. Pat. Nos. 7,723,356, 7,361,648, and 7,947,730.

In another embodiment of the application, the agent can include a phospholipase C (PLC) inhibitor. Examples of PLC inhibitors are described in U.S. Pat. No. 6,235,729 and can include U73122 (1-(6-((17β-3-methoxyestra-1,3,5(10)-trien-17-yl)amino)hexyl)-1H-pyrrole-2,5-dione), ET-18-OCH$_3$ (1-O-octadecyl-2-O-methyl-sn-glycero-3-phosphorylcholine), and RHC-80267 (1,6-bis-(cyclohexyloximinocarbonylamino)-hexane). Still other examples of PLC inhibitors can include α-hydroxyphosphonate compounds described in U.S. Pat. No. 5,519,163.

The agents used in methods described herein can be administered to the subject to treat the ocular disorder (e.g., macular degeneration, geographic atrophy, or Stargardt disease) using standard delivery methods including, for example, ophthalmic, topical, parenteral, subcutaneous, intravenous, intraarticular, intrathecal, intramuscular, intraperitoneal, intradermal injections, or by transdermal, buccal, oromucosal, oral routes or via inhalation. The particular approach and dosage used for a particular subject depends on several factors including, for example, the general health, weight, and age of the subject. Based on factors such as these, a medical practitioner can select an appropriate approach to treatment.

Treatment according to the method described herein can be altered, stopped, or re-initiated in a subject depending on the status of ocular disorder. Treatment can be carried out as intervals determined to be appropriate by those skilled in the art. For example, the administration can be carried out 1, 2, 3, or 4 times a day. In another embodiment, the primary amine compound can be administered after induction of macular degeneration has occurred.

The treatment methods can include administering to the subject a therapeutically effective amount of the agents alone or in combination. Determination of a therapeutically effective amount is within the capability of those skilled in the art. The exact formulation, route of administration, and dosage can be chosen by the individual physician in view of the subject's condition.

In some embodiments, a combination of agents described herein can be administered to a subject as a combination therapy to treat the ocular disorder. The phrase "combinatorial therapy" or "combination therapy" embraces the administration of one or more agents described herein, and/or potentially one or more other therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

For example, a therapeutically effective amount at least two or more, three or more, or four or more of a Gs or Gq coupled serotonin receptor antagonist, an alpha 1 adrenergic antagonist, an alpha-2 adrenergic receptor agonist, an adenylyl cyclase inhibitor, an M3 receptor antagonist, or a PLC inhibitor can be administered to a subject to treat the ocular disorder. In still other examples, a combination of agents that is administered to a subject to treat an ocular disorder can include: at least two or more of a serotonin receptor antagonist, alpha 1 adrenergic antagonist, alpha-2 adrenergic receptor agonist, adenylyl cyclase inhibitor, and/or M3 receptor antagonist, but not a PLC inhibitor; at least two or more of a serotonin receptor antagonist, alpha 1 adrenergic antagonist, alpha-2 adrenergic receptor agonist, adenylyl cyclase inhibitor, and/or PLC inhibitor, but not an M3 receptor antagonist; at least two or more of a serotonin receptor antagonist, alpha 1 adrenergic antagonist, alpha-2 adrenergic receptor agonist, PLC inhibitor, and/or M3 receptor antagonist, but not an adenylyl cyclase inhibitor; at least two or more of a serotonin receptor antagonist, alpha 1 adrenergic antagonist, adenylyl cyclase inhibitor, PLC inhibitor, and/or M3 receptor antagonist, but not an alpha-2 adrenergic receptor agonist; at least two or more of a one serotonin receptor antagonist, alpha-2 adrenergic receptor agonist, adenylyl cyclase inhibitor, PLC inhibitor, and/or M3 receptor antagonist, but not a alpha 1 adrenergic antagonist; at least two or more of an alpha 1 adrenergic antagonist, alpha-2 adrenergic receptor agonist, adenylyl cyclase inhibitor, PLC inhibitor, and/or M3 receptor antagonist, but not a serotonin receptor antagonist; or at least two or more of an adenylyl cyclase inhibitor, PLC inhibitor, and/or M3 receptor antagonist, but not a serotonin receptor antagonist, alpha 1 adrenergic antagonist, and alpha-2 adrenergic receptor agonist.

The dose, amount, and/or quantity of the agents described herein which are administered to the subject, can depend on the specific Gs or Gq coupled serotonin receptor antagonist, alpha 1 adrenergic antagonist, alpha-2 adrenergic receptor agonist, adenylyl cyclase inhibitor, M3 receptor antagonist, and/or PLC inhibitor selected. It will be appreciated that the dosage amounts used will depend on the potency of the specific Gs or Gq coupled serotonin receptor antagonist, alpha 1 adrenergic antagonist, alpha-2 adrenergic receptor agonist, adenylyl cyclase inhibitor, M3 receptor antagonist, and/or PLC inhibitor and the therapeutic regimen employed.

In another aspect, the specific Gs or Gq coupled serotonin receptor antagonist, alpha 1 adrenergic antagonist, alpha-2 adrenergic receptor agonist, adenylyl cyclase inhibitor, M3 receptor antagonist, and/or PLC inhibitor when administered in combination to subject can be administered at an amount or dosage to achieve a therapeutic effect that is substantially less (i.e., subtherapeutic dose or amount) than the amount or dose that would be required to achieve a therapeutic effect if each compound was administered alone. Co-administration of a Gs or Gq coupled serotonin receptor antagonists, alpha 1 adrenergic antagonist, alpha-2 adrenergic receptor agonist, adenylyl cyclase inhibitor, M3 receptor antagonist, and/or PLC inhibitor to the subject can also mitigate resistance to one single agent. Such resistance results either in the requirement for higher dosages of the drug and/or the renewed symptoms.

Moreover, co-administration of a Gs or Gq coupled serotonin receptor antagonists, alpha 1 adrenergic antagonist, alpha-2 adrenergic receptor agonist, adenylyl cyclase inhibitor, M3 receptor antagonist, and/or PLC inhibitor to the subject can mitigate toxicity and side effects associated with potentially administering a single agent at an amount effective to achieve a therapeutic effect. If two or more agents are used in concert, the dosage of any single drug can be lowered. This is beneficial to the patient since using lower levels of therapeutic agents is generally safer for the patient. Additionally, cells are less likely to generate resistance to the combination of drugs as they are to a single drug. Thus in some aspects, the agents described herein can be administered to a subject at a subtherapeutic level.

Formulation of pharmaceutical compositions using agents described herein for use in the modes of administration noted above (and others) are described, for example, in Remington's Pharmaceutical Sciences (18th edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

In one example, one or more of the agents can be provided in an ophthalmic preparation that can be administered to the subject's eye. The ophthalmic preparation can contain the agent in a pharmaceutically acceptable solution, suspension or ointment. Some variations in concentration will necessarily occur, depending on the particular agent employed, the condition of the subject to be treated and the like, and the person responsible for treatment will determine the most suitable concentration for the individual subject. The ophthalmic preparation can be in the form of a sterile aqueous solution containing, if desired, additional ingredients, for example, preservatives, buffers, tonicity agents, antioxidants, stabilizers, nonionic wetting or clarifying agents, and viscosity increasing agents.

Examples of preservatives for use in such a solution include benzalkonium chloride, benzethonium chloride, chlorobutanol, thimerosal and the like. Examples of buffers include boric acid, sodium and potassium bicarbonate, sodium and potassium borates, sodium and potassium carbonate, sodium acetate, and sodium biphosphate, in amounts sufficient to maintain the pH at between about pH 6 and about pH 8, and for example, between about pH 7 and about pH 7.5. Examples of tonicity agents are dextran 40, dextran 70, dextrose, glycerin, potassium chloride, propylene glycol, and sodium chloride.

Examples of antioxidants and stabilizers include sodium bisulfite, sodium metabisulfite, sodium thiosulfite, and thiourea. Examples of wetting and clarifying agents include polysorbate 80, polysorbate 20, poloxamer 282 and tyloxapol. Examples of viscosity-increasing agents include gelatin, glycerin, hydroxyethylcellulose, hydroxmethylpropylcellulose, lanolin, methylcellulose, petrolatum, polyethylene glycol, polyvinyl alcohol, polyvinylpyrrolidone, and carboxymethylcellulose. The ophthalmic preparation will be administered topically to the eye of the subject in need of treatment by conventional methods, for example, in the form of drops or by bathing the eye in the ophthalmic solution.

The agents can also be formulated for topical administration through the skin. "Topical delivery systems" also include transdermal patches containing the ingredient to be administered. Delivery through the skin can further be achieved by iontophoresis or electrotransport, if desired.

Formulations for topical administration to the skin can include, for example, ointments, creams, gels and pastes comprising the agent in a pharmaceutical acceptable carrier. The formulation of the agent for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Subjects affected with or at risk of macular degeneration, which are not readily accessible or suitable for ophthalmic (e.g. eye-drops) and/or topical administration, can be treated by a systemic approach, such as intravenous infusion. For example, the agent can be administered at a low dosage by continuous intravenous infusion. In another example, in which a patient requires longer-term care, the agent can be administered intermittently (e.g., every 12-24 hours). In a variation of this approach, the initial or loading dose can be followed by maintenance doses that are less than, (e.g., half) the loading dose or by continuous infusion. The duration of such treatment can be determined by those having skill in the art, based on factors, for example, the severity of the condition and the observation of improvements.

When administering the agent to the subject by intravenous infusion, devices and equipment (e.g., catheters, such as central or peripheral venous catheters, tubing, drip chambers, flashback bulbs, injection Y sites, stopcocks, and infusion bags) can be used that are compatible with the agent.

As discussed above, the agent may be administered to a subject in order to treat or prevent macular degeneration and other forms of retinal disease whose etiology involves light induced retinal degeneration, aberrant all-trans-RAL clearance, and/or ROS generation, such as molecular degeneration, geographic atrophy, Stargardt disease, and retinitis pigmentosa. Other diseases, disorders, or conditions characterized by light induced degeneration, aberrant all-trans-RAL and ROS generation may be similarly treated.

In one embodiment, a subject is diagnosed as having symptoms of macular degeneration, and then a disclosed compound is administered. In another embodiment, a subject may be identified as being at risk for developing macular degeneration (risk factors include a history of smoking, age, female gender, and family history), and then a disclosed compound is administered. In another embodiment, a subject may have dry AMD in both eye, and then a disclosed compound is administered. In another embodiment, a subject may have wet AMD in one eye but dry AMD in the other eye, and then a disclosed compound is administered. In yet another embodiment, a subject may be diagnosed as having Stargardt disease and then a disclosed compound is administered. In another embodiment, a subject is diagnosed as having symptoms of other forms of retinal disease whose etiology involves aberrant all-trans-RAL clearance, such as geographic atrophy (GA), and then the compound is administered. In another embodiment, a subject may be identified as being at risk for developing other forms of retinal disease whose etiology involves all-trans-RAL clearance, and then the disclosed compound is administered. In some embodiments, a compound is administered prophylactically. In some embodiments, a subject has been diagnosed as having the disease before retinal damage is apparent. In some embodiments, a human subject may know that he or she is in need of the macular generation treatment or prevention.

In some embodiments, a subject may be monitored for the extent of macular degeneration. A subject may be monitored in a variety of ways, such as by eye examination, dilated eye examination, fundoscopic examination, visual acuity test, and/or biopsy. Monitoring can be performed at a variety of times. For example, a subject may be monitored after a compound is administered. The monitoring can occur, for example, one day, one week, two weeks, one month, two months, six months, one year, two years, five years, or any other time period after the first administration of a compound. A subject can be repeatedly monitored. In some embodiments, the dose of a compound may be altered in response to monitoring.

In some embodiments, the disclosed methods may be combined with other methods for treating or preventing macular degeneration or other forms of retinal disease whose etiology involves light induced retard degeneration aberrant all-trans-RAL clearance, and/or ROS generation, such as photodynamic therapy. For example, a patient may be treated with more than one therapy for one or more diseases or disorders. For example, a patient may have one eye afflicted with dry form AMD, which is treated with a compound of the invention, and the other eye afflicted with wet form AMD, which is treated with, e.g., photodynamic therapy.

In still other embodiments, the agents can be administered alone or as part of a combinatorial therapy with additional therapeutic agents that can inhibit and/or antagonize the Gs or Gq signaling cascade and inhibit ROS production and/or inhibit and/or antagonize all-trans-retinal accumulation. In some embodiments, the additional therapeutic agents can include NADPH oxidase inhibitors, such as apocynin (1-(4-hydroxy-3-methoxyphenylethanone) or diacylglycerols) and agents that selectively target aberrant all-trans-retinal accumulation in the retina.

Examples of agents that selectively target all-trans-retinal accumulation are described in PCT/US2011/071995 and can include primary amines (i.e., primary amine compounds) that form reversible Schiff-bases with free all-trans-RAL, which has escaped sequestering in photoreceptor outer segments of the retina without adversely affecting normal retinoid cycle.

In an embodiment of the application, the primary amine compounds that can form stable Schiff-bases with all-trans-RAL under physiological conditions of the retina and that can inhibit retinal degeneration upon administration to a subject can be selected using an in vitro assay that measures the ability of a primary amine compound to form a Schiff base with retinal under physiological condition of the retina and in vivo assays that measure, respectively, 11-cis-retinal formation and the optical coherence tomography score of retinas of Rdh8$^{-/-}$Abca4$^{-/-}$ mice. Primary amine compounds that form a Schiff-base with all-trans-RAL or its metabolite under physiologic conditions of the retina and that when administered to a Rdh8$^{-/-}$Abca4$^{-/-}$ mouse increase the optical coherence tomography score of the mouse to at least about 2.5 and increase 11-cis-retinal amount at least about 30% in comparison to untreated control animal are effective in treating retinal degeneration in a subject associated with aberrant all-trans-RAL clearance. Primary amines compounds that do not form a form a Schiff-base with all-trans-RAL or its metabolite under physiologic conditions of the retina or which when administered to a Rdh8$^{-/-}$Abca4$^{-/-}$ mouse do not increase the optical coherence tomography score of the mouse to at least about 2.5 and increase 11-cis-retinal amount at least about 30% in comparison to untreated control animal, were found to be ineffective in treating retinal degeneration in a subject associated with aberrant all-trans-RAL clearance. Additionally, therapeutic efficacy of the primary amine compounds of the application can be determined using an in vitro assay that measures the ability of a primary amine compound to improve viability of RPE cells treated with retinal.

In some embodiments, the primary amine compound can include the structural formula (VIII):

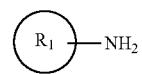

(VIII)

wherein $R_1$ is an aliphatic and/or aromatic compound.

Primary amine compounds having formula I that are used to treat retinal degeneration in accordance with an embodiment of the application can upon administration to the subject form a reversible Schiff-base with the all-trans-RAL without adversely affecting normal retinoid cycle performance and when administered to a $Rdh8^{-/-}Abca4^{-/-}$ mouse increase the optical coherence tomography score of the mouse to at least about 2.5 and increase 11-cis-retinal amount at least about 30% in comparison to untreated control animal. Primary amine compounds in accordance with the application, however, do not include and are not a local anesthetic, which includes an aromatic amine that demonstrates sodium channel blockade when administered to the subject.

Advantageously, the primary amine compounds in accordance with the application do not inhibit RPE65 enzymatic activity or any other proteins involved in retinoid metabolism in the eye of the subject. The primary amine compounds can reduce the formation of A2E and/or retinal dimer in the subject's retina, promote 11-cis-retinal production in the subject, and does not cause night blindness.

In some embodiments, primary compounds having formula I that upon administration to a subject form a reversible Schiff-base with the all-trans-RAL without adversely affecting normal retinoid cycle performance and that when administered to a $Rdh8^{-/-}$ $Abca4^{-/-}$ mouse increase the optical coherence tomography score of the mouse to at least about 2.5 and increase 11-cis-retinal amount at least about 30% in comparison to untreated control animal can be selected using the methods described in the Examples from known primary amine compounds.

In an embodiment of the application, the primary amine compounds can include known primary amine compounds having the following structural formulas:

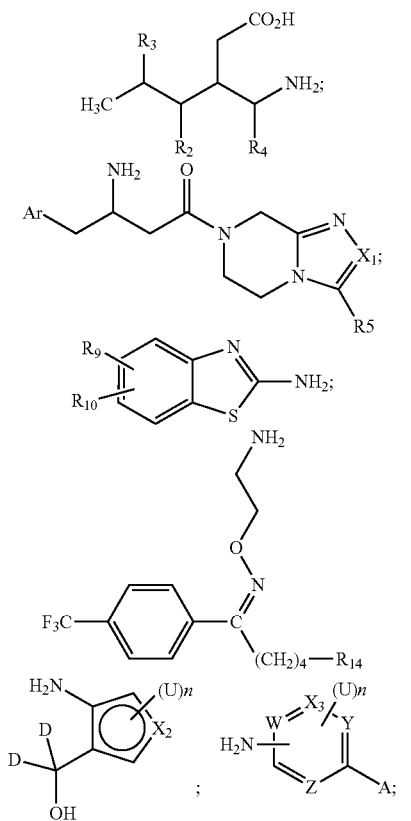

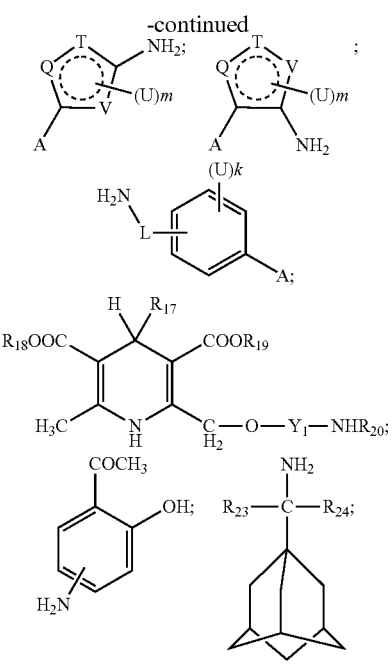

wherein $R_2$ is hydrogen or $(C_1-C_6)$ straight chain or branched unsubstituted or substituted alkyl or phenyl;

$R_3$ is straight or branched unsubstituted or substituted alkyl of from 1 to 8 carbon atoms, straight or branched alkenyl of from 2 to 8 carbon atoms, cycloalkyl of from 3 to 7 carbon atoms, alkoxy of from 1 to 6 carbon atoms, -alkylcycloalkyl, -alkylalkoxy, -alkyl, OH, -alkylphenyl, -alkylphenoxy, -phenyl or substituted phenyl;

$R_4$ is hydrogen or $(C_1-C_6)$ straight chain or branched unsubstituted or substituted alkyl, or carboxyl;

Ar is phenyl which is unsubstituted or substituted with 1-5 of $R_7$, wherein $R_7$ is independently selected from the group consisting of:
(1) halogen,
(2) $C_{1-6}$ alkyl, which is linear or branched and is unsubstituted or substituted with 1-5 halogens,
(3) $OC_{1-6}$ alkyl, which is linear or branched and is unsubstituted or substituted with 1-5 halogens, and
(4) CN;

$X_1$ is selected from the group consisting of:
(1) N, and
(2) $CR_6$;

$R_5$ and $R_6$ are independently selected from the group consisting of:
(1) hydrogen,
(2) CN,
(3) $C_{1-10}$ alkyl, which is linear or branched and which is unsubstituted or substituted with 1-5 halogens or phenyl, which is unsubstituted or substituted with 1-5 substituents independently selected from halogen, CN, OH, $R_8$, $OR_8$, $NHSO_2R_8$, $SO_2R_8$, $CO_2H$, and $CO_2C_{1-6}$ alkyl, wherein the $CO_2C_{1-6}$ alkyl is linear or branched,
(4) phenyl which is unsubstituted or substituted with 1-5 substituents independently selected from halogen, CN, OH, $R_8$, $OR_8$, $NHSO_2R_8$, $SO_2R_8$, $CO_2H$, and $CO_2C_{1-6}$ alkyl, wherein the $CO_2C_{1-6}$ alkyl is linear or branched, and (5) a 5- or 6-membered heterocycle which may be saturated or unsaturated comprising 1-4 heteroatoms independently selected from N, S and O, the heterocycle being unsubstituted or substituted with 1-3 substituents independently selected from oxo, OH, halogen, $C_{1-6}$ alkyl, and $OC_{1-6}$ alkyl, wherein the $C_{1-6}$ alkyl and $OC_{1-6}$ alkyl are linear or branched and optionally substituted with 1-5 halogens;

$R_8$ is $C_{1-6}$ alkyl, which is linear or branched and which is unsubstituted or substituted with 1-5 groups independently selected from halogen, $CO_2H$, and $CO_2C_{1-6}$ alkyl, wherein the $CO_2C_{1-6}$ alkyl is linear or branched;

$R_9$ and $R_{10}$ may be the same or different and are hydrogen, straight or branched alkyl of from one to six carbon atoms, lower alkylaryl, lower alkenyl, phenyl, $CF_3$, hydroxy, lower alkoxy, lower alkylthio, lower alkylsulphonyl, $CF_3O$, at the six position halogen, nitro, carboxy, lower alkoxycarbonyl, $NR_{11}R_{12}CO$, $NR_{11}R_{12}$, $R_{11}CONR_{12}$, CN, $NR_{11}R_{12}SO_2$, wherein $R_{11}$ and $R_{12}$ may be the same or different and are hydrogen, lower alkyl, or aryl; $R_9$ and $R_{10}$ may together form a carbocyclic or methylenedioxy ring;

$R_{14}$ is cyano, cyanomethyl, methoxymethyl, or ethoxymethyl;

$X_2$ is O, N(H), or S, het is a 5 or 6-membered heterocycle, n is 0, 1, 2, or 3, and each D is an unbranched lower alkyl group;

U is a substituent selected from halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more heteroatoms selected from nitrogen, oxygen, and sulfur atoms; lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino) sulfonylamino; aryl, optionally substituted by groups selected from a halogen atom, hydroxyl, carbamoyl, aryl and amino; and a monocyclic or bicyclic heterocyclic group containing one or more hetero-atoms selected from nitrogen, oxygen, and sulfur atoms;

Q, T, and V are each, independently, N, S, O CU or CH;
W, X, Y, and Z are each, independently, N, S, O CU or CH, such that at least one of W, X, Y, and Z is N;
A is

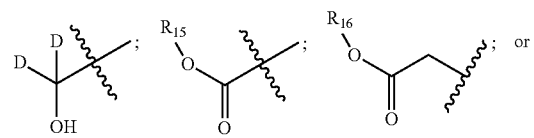

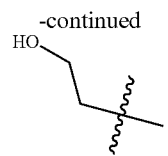

D is unbranched lower alkyl;
$R_{15}$ and $R_{16}$ are each independently substituted or unsubstituted $C_1$, $C_2$, $C_3$, $C_4$, $C_5$, $C_6$, $C_7$, or $C_8$, straight chain alkyl, or substituted or unsubstituted $C_3$, $C_4$, $C_5$, $C_6$, $C_7$, or $C_8$, branched chain alkyl;
L is a single bond or $CH_2$;
m is 0, 1, or 2;
n is 0, 1, 2, 3, or 4;
$Y_1$ is —$(CH_2)_2$—, —$(CH_2)_3$—, —$CH_2CH(CH_3)$— or —$CH_2C(CH_3)_2$—;
$R_{17}$ is aryl or heteroaryl;
$R_{18}$ and $R_{19}$ are each independently $C_1$-$C_4$ alkyl or 2-methoxyethyl;
$R_{20}$ is hydrogen, $C_1$-$C_4$ alkyl, 2-($C_1$-$C_4$ alkoxy)ethyl, cyclopropylmethyl, benzyl, or —$(CH_2)_{m1}COR_{21}$ where m1 is 1, 2 or 3 and $R^{21}$ is hydroxy, $C_1$-$C_4$ alkoxy or —$NR_{22}$ where $R_{22}$ hydrogen or $C_1$-$C_4$ alkyl;
$R_{23}$ and $R_{24}$ can be the same or different and are hydrogen, methyl, or ethyl
as well as pharmaceutically acceptable salts thereof.

In some embodiments, the primary amine compound is a compound having the following structural formula:

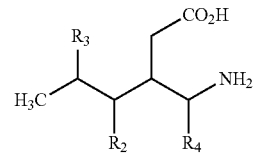

wherein $R_2$ is hydrogen or ($C_1$-$C_6$) straight chain or branched unsubstituted or substituted alkyl;
$R_3$ is straight or branched unsubstituted or substituted alkyl of from 1 to 8 carbon atoms, straight or branched alkenyl of from 2 to 8 carbon atoms, cycloalkyl of from 3 to 7 carbon atoms, alkoxy of from 1 to 6 carbon atoms, -alkylcycloalkyl, -alkylalkoxy, -alkyl, OH, -alkylphenyl, -alkylphenoxy, -phenyl or substituted phenyl;
$R_4$ is hydrogen or ($C_1$-$C_6$) straight chain or branched unsubstituted or substituted alkyl, or carboxyl;
as well as pharmaceutically acceptable salts thereof.

In other embodiments, the primary amine compound is a compound having the following structural formula:

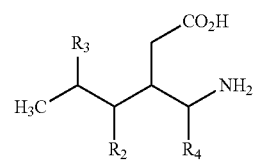

wherein $R_2$ is hydrogen, straight or branched alkyl of from 1 to 6 carbon atoms or phenyl;
$R_3$ is straight or branched alkyl of from 1 to 8 carbon atoms, straight or branched alkenyl of from 2 to 8 carbon atoms, cycloalkyl of from 3 to 7 carbon atoms, alkoxy of from 1 to 6 carbon atoms, -alkylcycloalkyl, -alkylalkoxy, -alkyl OH -alkylphenyl, -alkylphenoxy, -phenyl or substituted phenyl; and $R_4$ is hydrogen, and $R_2$ is straight or branched alkyl of from 1 to 6 carbon atoms or phenyl when $R_3$ is methyl, or a pharmaceutically acceptable salt thereof.

In other embodiments, the primary amine compound can have the following structural formula:

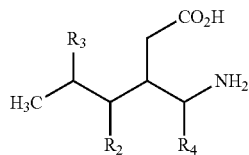

wherein $R_2$ is methyl, $R_3$ is an alkyl, and $R_4$ is a hydrogen, or a pharmaceutically acceptable salt thereof;

Specific examples of compounds of above noted formulas are selected from: 3-Aminomethyl-5-methylhexanoic acid; 3-Aminomethyl-5-methylheptanoic acid; 3-Aminomethyl-5-methyl-octanoic acid; 3-Aminomethyl-5-methyl-nonanoic acid; 3-Aminomethyl-5-methyl-decanoic acid; 3-Aminomethyl-5-methyl-undecanoic acid; 3-Aminomethyl-5-methyl-dodecanoic acid; 3-Aminomethyl-5-methyl-tridecanoic acid; 3-Aminomethyl-5-cyclopropyl-hexanoic acid; 3-Aminomethyl-5-cyclobutyl-hexanoic acid; 3-Aminomethyl-5-cyclopentyl-hexanoic acid; 3-Aminomethyl-5-cyclohexyl-hexanoic acid; 3-Aminomethyl-5-trifluoromethyl-hexanoic acid; 3-Aminomethyl-5-phenyl-hexanoic acid; 3-Aminomethyl-5-(2-chlorophenyl)-hexanoic acid; 3-Aminomethyl-5-(3-chlorophenyl)-hexanoic acid; 3-Aminomethyl-5-(4-chlorophenyl)-hexanoic acid; 3-Aminomethyl-5-(2-methoxyphenyl)-hexanoic acid; 3-Aminomethyl-5-(3-methoxyphenyl)-hexanoic acid; 3-Aminomethyl-5-(4-methoxyphenyl)-hexanoic acid; 3-Aminomethyl-5-(phenylmethyl)-hexanoic acid; (S)-3-(Aminomethyl)-5-methylhexanoic acid; (R)-3-(Aminomethyl)-5-methylhexanoic acid; (3R,4S)-3-Aminomethyl-4,5-dimethyl-hexanoic acid; 3-Aminomethyl-4,5-dimethyl-hexanoic acid; (3R,4S)-3-Aminomethyl-4,5-dimethyl-hexanoic acid MP; (3S,4S)-3-Aminomethyl-4,5-dimethyl-hexanoic acid; (3R,4R)-3-Aminomethyl-4,5-dimethyl-hexanoic acid MP; 3-Aminomethyl-4-isopropyl-hexanoic acid; 3-Aminomethyl-4-isopropyl-heptanoic acid; 3-Aminomethyl-4-isopropyl-octanoic acid; 3-Aminomethyl-4-isopropyl-nonanoic acid; 3-Aminomethyl-4-isopropyl-decanoic acid; 3-Aminomethyl-4-phenyl-5-methyl-hexanoic acid; (3S,5S)-3-Aminomethyl-5-methoxy-hexanoic acid; (3S,5S)-3-Aminomethyl-5-ethoxy-hexanoic acid; (3S,5S)-3-Aminomethyl-5-propoxy-hexanoic acid; (3S,5S)-3-Aminomethyl-5-isopropoxy-hexanoic acid; (3S,5S)-3-Aminomethyl-5-tert-butoxy-hexanoic acid; (3S,5S)-3-Aminomethyl-5-fluoromethoxy-hexanoic acid; (3S,5S)-3-Aminomethyl-5-(2-fluoro-ethoxy)-hexanoic acid; (3S,5S)-3-Aminomethyl-5-(3,3,3-trifluoro-propoxy)-hexanoic acid; (3S,5S)-3-Aminomethyl-5-phenoxy-hexanoic acid; (3S,5S)-3-Aminomethyl-5-(4-chloro-phenoxy)-hexanoic acid; (3S,5S)-3-Aminomethyl-5-(3-chloro-phenoxy)-hexanoic acid; (3S,5S)-3-Aminomethyl-5-(2-chloro-phenoxy)-hexanoic acid; (3S,5S)-3-Aminomethyl-5-(4-fluoro-phenoxy)-hexanoic acid; (3S,5S)-3-Aminomethyl-5-(3-fluoro-phenoxy)-hexanoic acid; (3S,5S)-3-Aminomethyl-5-(2-fluoro-phenoxy)-hexanoic acid; (3S,5S)-3-Aminomethyl-5-(4-methoxy-phenoxy)-hexanoic acid; (3S,5S)-3-Aminomethyl-5-(3-methoxy-phenoxy)-hexanoic acid; (3S,5S)-3-Aminomethyl-5-(2-methoxy-phenoxy)-hexanoic acid; (3S,5S)-3-Aminomethyl-5-(4-nitro-phenoxy)-hexanoic acid; (3S,5S)-3-Aminomethyl-5-(3-nitro-phenoxy)-hexanoic acid; (3S,5S)-3-Aminomethyl-5-(2-nitro-phenoxy)-hexanoic acid; (3S,5S)-3-Aminomethyl-6-hydroxy-5-methyl-hexanoic acid; (3S,5S)-3-Aminomethyl-6-methoxy-5-methyl-hexanoic acid; (3S,5S)-3-Aminomethyl-6-ethoxy-5-methyl-hexanoic acid; (3S,5S)-3-Aminomethyl-5-methyl-6-propoxy-hexanoic acid; (3S,5S)-3-Aminomethyl-6-isopropoxy-5-methyl-hexanoic acid; (3S,5S)-3-Aminomethyl-6-tert-butoxy-5-methyl-hexanoic acid; (3S,5S)-3-Aminomethyl-6-fluoromethoxy-5-methyl-hexanoic acid; (3S,5S)-3-Aminomethyl-6-(2-fluoro-ethoxy)-5-methyl-hexanoic acid; (3S,5S)-3-Aminomethyl-5-methyl-6-(3,3,3-trifluoro-propoxy)-hexanoic acid; (3S,5S)-3-Aminomethyl-5-methyl-6-phenoxy-hexanoic acid; (3S,5S)-3-Aminomethyl-6-(4-chloro-phenoxy)-5-methyl-hexanoic acid; (3S,5S)-3-Aminomethyl-6-(3-chloro-phenoxy)-5-methyl-hexanoic acid; (3S,5S)-3-Aminomethyl-6-(2-chloro-phenoxy)-5-methyl-hexanoic acid; (3S,5S)-3-Aminomethyl-6-(4-fluoro-phenoxy)-5-methyl-hexanoic acid; (3S,5S)-3-Aminomethyl-6-(3-fluoro-phenoxy)-5-methyl-hexanoic acid; (3S,5S)-3-Aminomethyl-6-(2-fluoro-phenoxy)-5-methyl-hexanoic acid; (3S,5S)-3-Aminomethyl-6-(4-methoxy-phenoxy)-5-methyl-hexanoic acid; (3S,5S)-3-Aminomethyl-6-(3-methoxy-phenoxy)-5-methyl-hexanoic acid; (3S,5S)-3-Aminomethyl-6-(2-methoxy-phenoxy)-5-methyl-hexanoic acid; (3S,5S)-3-Aminomethyl-5-methyl 6-(4-trifluoromethyl-phenoxy)-hexanoic acid; (3S,5S)-3-Aminomethyl-5-methyl 6-(3-trifluoromethyl-phenoxy)-hexanoic acid; (3S,5S)-3-Aminomethyl-5-methyl 6-(2-trifluoromethyl-phenoxy)-hexanoic acid; (3S,5S)-3-Aminomethyl-5-methyl 6-(4-nitro-phenoxy)-hexanoic acid; (3S,5S)-3-Aminomethyl-5-methyl 6-(3-nitro-phenoxy)-hexanoic acid; (3S,5S)-3-Aminomethyl-5-methyl 6-(2-nitro-phenoxy)-hexanoic acid; (3S,5S)-3-Aminomethyl-6-benzyloxy-5-methyl-hexanoic acid; (3S,5S)-3-Aminomethyl-7-hydroxy-5-methyl-heptanoic acid; (3S,5S)-3-Aminomethyl-7-methoxy-5-methyl-heptanoic acid; (3S,5S)-3-Aminomethyl-7-ethoxy-5-methyl-heptanoic acid; (3S,5S)-3-Aminomethyl-5-methyl-7-propoxy-heptanoic acid; (3S,5S)-3-Aminomethyl-7-isopropoxy-5-methyl-heptanoic acid; (3S,5S)-3-Aminomethyl-7-tert-butoxy-5-methyl-heptanoic acid; (3S,5S)-3-Aminomethyl-7-fluoromethoxy-5-methyl-heptanoic acid; (3S,5S)-3-Aminomethyl-7-(2-fluoro-ethoxy)-5-methyl-heptanoic acid; (3S,5S)-3-Aminomethyl-5-methyl-7-(3,3,3-trifluoro-propoxy)-heptanoi-c acid; (3S,5S)-3-Aminomethyl-7-benzyloxy-5-methyl-heptanoic acid; (3S,5S)-3-Aminomethyl-5-methyl-7-phenoxy-heptanoic acid; (3S,5S)-3-Aminomethyl-7-(4-chloro-phenoxy)-5-methyl-heptanoic acid; (3S,5S)-3-Aminomethyl-7-(3-chloro-phenoxy)-5-methyl-heptanoic acid; (3S,5S)-3-Aminomethyl-7-(2-chloro-phenoxy)-5-methyl-heptanoic acid; (3S,5S)-3-Aminomethyl-7-(4-fluoro-phenoxy)-5-methyl-heptanoic acid; (3S,5S)-3-Aminomethyl-7-(3-fluoro-phenoxy)-5-methyl-heptanoic acid; (3S,5S)-3-Aminomethyl-7-(2-fluoro-phenoxy)-5-methyl-heptanoic acid; (3S,5S)-3-Aminomethyl-7-(4-methoxy-phenoxy)-5-methyl-heptanoic acid; (3S,5S)-3-Aminomethyl-7-(3-methoxy-phenoxy)-5-methyl-heptanoic acid; (3S,5S)-3-Aminomethyl-7-(2-methoxy-phenoxy)-5-methyl-heptanoic acid; (3S,5S)-3-Aminomethyl-5-methyl-7-(4-trifluoromethyl-phenoxy)-heptan-oic acid; (3S,5S)-3-Aminomethyl-5-methyl-7-(3-trifluoromethyl-phenoxy)-heptan-oic acid; (3S,5S)-3-Aminomethyl-5-methyl-7-(2-trifluoromethyl-phenoxy)-heptan-oic acid; (3S, 5S)-3-Aminomethyl-5-methyl-7-(4-nitro-phenoxy)-heptanoic acid; (3S,5S)-3-Aminomethyl-5-methyl-7-(3-nitro-phenoxy)-heptanoic acid; (3S,5S)-3-Aminomethyl-5-methyl-7-(2-nitro-phenoxy)-heptanoic acid; (3S,5S)-3-Aminomethyl-5-methyl-6-phenyl-hexanoic acid; (3S,5S)-3-Aminomethyl-6-(4-chloro-phenyl)-5-methyl-hexanoic acid; (3S,5S)-3-Aminomethyl-6-(3-chloro-phenyl)-5-methyl-hexanoic acid; (3S,5S)-3-Aminomethyl-6-(2-chloro-phenyl)-5-methyl-hexanoic acid; (3S,5S)-3-Aminomethyl-6-(4-methoxy-phenyl)-5-methyl-hexanoic acid; (3S,5S)-3-Aminomethyl-6-(3-methoxy-phenyl)-5-methyl-hexanoic acid; (3S,5S)-3-Aminomethyl-6-(2-methoxy-phenyl)-5-methyl-hexanoic acid; (3S,5S)-3-Aminomethyl-6-(4-fluoro-phenyl)-5-methyl-hexanoic acid; (3S,5S)-3-Aminomethyl-6-(3-fluoro-phenyl)-5-methyl-hexanoic acid; (3S,5S)-3-Aminomethyl-6-(2-fluoro-phenyl)-5-methyl-hexanoic acid; (3S,5R)-3-Aminomethyl-5-methyl-7-phenyl-heptanoic acid; (3S,5R)-3-Aminomethyl-7-(4-chloro-phenyl)-5-methyl-heptanoic acid; (3S,5R)-3-Aminomethyl-7-(3-chloro-phenyl)-5-methyl-heptanoic acid; (3S,5R)-3-Aminomethyl-7-(2-chloro-phenyl)-5-methyl-heptanoic acid; (3S,5R)-3-Aminomethyl-7-(4-methoxy-phenyl)-5-methyl-heptanoic acid; (3S,5R)-3-Aminomethyl-7-(3-methoxy-phenyl)-5-methyl-heptanoic acid; (3S,5R)-3-Aminomethyl-7-(2-methoxy-phenyl)-5-methyl-heptanoic acid; (3S,5R)-3-Aminomethyl-7-(4-fluoro-phenyl)-5-methyl-heptanoic acid; (3S,5R)-3-Aminomethyl-7-(3-fluoro-phenyl)-5-methyl-heptanoic acid; (3S,5R)-3-Aminomethyl-7-(2-fluoro-phenyl)-5-methyl-heptanoic acid; (3S,5R)-3-Aminomethyl-5-methyl-oct-7-enoic acid; (3S,5R)-3-Aminomethyl-5-methyl-non-8-enoic acid; (E)-(3S,5S)-3-Aminomethyl-5-methyl-oct-6-enoic acid; (Z)-(3S,5S)-3-Aminomethyl-5-methyl-oct-6-enoic acid; (Z)-(3S,5S)-3-Aminomethyl-5-methyl-non-6-enoic acid; (E)-(3S,5S)-3-Aminomethyl-5-methyl-non-6-enoic acid; (E)-(3S,5R)-3-Aminomethyl-5-methyl-non-7-enoic acid; (Z)-(3S,5R)-3-Aminomethyl-5-methyl-non-7-enoic acid; (Z)-(3S,5R)-3-Aminomethyl-5-methyl-dec-7-enoic acid; (E)-(3S,5R)-3-Aminomethyl-5-methyl-undec-7-enoic acid; (3S,5S)-3-Aminomethyl-5,6,6-trimethyl-heptanoic acid; (3S,5S)-3-Aminomethyl-5,6-dimethyl-heptanoic acid; (3S,5S)-3-Aminomethyl-5-cyclopropyl-hexanoic acid; (3S,5S)-3-Aminomethyl-5-cyclobutyl-hexanoic acid; (3S,5S)-3-Aminomethyl-5-cyclopentyl-hexanoic acid; (3S,5S)-3-Aminomethyl-5-cyclohexyl-hexanoic acid; (3S,5R)-3-Aminomethyl-5-methyl-heptanoic acid; (3S,5R)-3-Aminomethyl-5-methyl-octanoic acid; (3S,5R)-3-Aminomethyl-5-methyl-nonanoic acid; (3S,5R)-3-Aminomethyl-5-methyl-decanoic acid; (3S,5R)-3-Aminomethyl-5-methyl-undecanoic acid; (3S,5R)-3-Aminomethyl-5-methyl-dodecanoic acid; (3S,5R)-3-Aminomethyl-5,9-dimethyl-decanoic acid; (3S,5R)-3-Aminomethyl-5,7-dimethyl-octanoic acid; (3S,5R)-3-Aminomethyl-5,8-dimethyl-nonanoic acid; (3S,5R)-3-Aminomethyl-6-cyclopropyl-5-methyl-hexanoic acid; (3S,5R)-3-Aminomethyl-6-cyclobutyl-5-methyl-hexanoic acid; (3S,5R)-3-Aminomethyl-6-cyclopentyl-5-methyl-hexanoic acid; (3S,5R)-3-Aminomethyl-6-cyclohexyl-5-methyl-hexanoic acid; (3S,5R)-3-Aminomethyl-7-cyclopropyl-5-methyl-heptanoic acid; (3S,5R)-3-Aminomethyl-7-cyclobutyl-5-methyl-heptanoic acid; (3S,5R)-3-Aminomethyl-7-cyclopentyl-5-methyl-heptanoic acid; (3S,5R)-3-Aminomethyl-7-cyclohexyl-5-methyl-heptanoic acid; (3S,5R)-3-Aminomethyl-8-cyclopropyl-5-methyl-octanoic acid; (3S,5R)-3-Aminomethyl-8-cyclobutyl-5-methyl-octanoic acid; (3S,5R)-3-Aminomethyl-8-cyclopentyl-5-methyl-octanoic acid; (3S,5R)-3-Aminomethyl-8-cyclohexyl-5-methyl-octanoic acid; (3S,5S)-3-Aminomethyl-6-fluoro-5-methyl-hexanoic acid; (3S,5S)-3-Aminomethyl-7-fluoro-5-methyl-heptanoic acid; (3S,5R)-3-Aminomethyl-8-fluoro-5-methyl-octanoic acid; (3S,5R)-3-Aminomethyl-9-fluoro-5-methyl-nonanoic acid; (3S,5S)-3-Aminomethyl-7,7,7-trifluoro-5-methyl-heptanoic acid; (3S,5R)-3-Aminomethyl-8,8,8-trifluoro-5-methyl-octanoic acid; (3S,5R)-3-Aminomethyl-5-methyl-8-phenyl-octanoic acid; (3S,5S)-3-Aminomethyl-5-methyl-6-phenyl-hexanoic acid; (3S,5R)-3-Aminomethyl-5-methyl-7-phenyl-heptanoic acid; and pharmaceutically acceptable salts thereof. Methods of synthesizing the above noted compounds are described in PCT Patent Application No. WO 00/76958, which is incorporated herein by reference in its entirety.

In other embodiments, the primary amine compound can comprise at least one of (S)-3-(Aminomethyl)-5-methylhexanoic acid or (R)-3-(Aminomethyl)-5-methylhexanoic acid. In still other embodiments, the primary amine compound can include a mixture of (S)-3-(Aminomethyl)-5-methylhexanoic acid and (R)-3-(Aminomethyl)-5-methylhexanoic acid. For example, the primary amine compound can comprise a racemic mixture of (S)-3-(Aminomethyl)-5-methylhexanoic acid and (R)-3-(Aminomethyl)-5-methylhexanoic acid. In other examples, the primary amine compound can comprise a mixture of: less than about 50% by weight (S)-3-(Aminomethyl)-5-methylhexanoic acid and greater than about 50% by weight (R)-3-(Aminomethyl)-5-methylhexanoic acid, less than about 25% by weight (S)-3-(Aminomethyl)-5-methylhexanoic acid and greater than about 75% by weight (R)-3-(Aminomethyl)-5-methylhexanoic acid, less than about 10% by weight (S)-3-(Aminomethyl)-5-methylhexanoic acid and greater than about 90% by weight (R)-3-(Aminomethyl)-5-methylhexanoic acid, less than about 1% by weight (S)-3-(Aminomethyl)-5-methylhexanoic acid and greater than about 99% by weight (R)-3-(Aminomethyl)-5-methylhexanoic acid, greater than about 50% by weight (S)-3-(Aminomethyl)-5-methylhexanoic acid and less than about 50% by weight (R)-3-(Aminomethyl)-5-methylhexanoic acid, greater than about 75% by weight (S)-3-(Aminomethyl)-5-methylhexanoic acid and less than about 25% by weight (R)-3-(Aminomethyl)-5-methylhexanoic acid, greater than about 90% by weight (S)-3-(Aminomethyl)-5-methylhexanoic acid and less than about 10% by weight (R)-3-(Aminomethyl)-5-methylhexanoic acid, or greater than about 99% by weight (S)-3-(Aminomethyl)-5-methylhexanoic acid and less than about 1% by weight (R)-3-(Aminomethyl)-5-methylhexanoic acid.

In a still further embodiment, the primary amine compound can consist essentially of or consist of (S)-3-(Aminomethyl)-5-methylhexanoic acid. In yet another embodiment, the primary amine compound can consist essentially of or consist of (R)-3-(Aminomethyl)-5-methylhexanoic acid.

In some embodiments, the primary amine compound is a compound having the following structural formula:

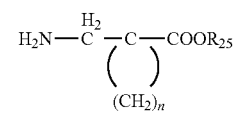

wherein $R_{25}$ is hydrogen or a lower alky, such as a ($C_1$-$C_6$) straight chain or branched unsubstituted or substituted alkyl, n is 4, 5, or 6 and pharmaceutically acceptable salts thereof. Compounds having the above noted structural formula and methods of forming such compounds are described in U.S. Pat. No. 4,024,175, which is incorporated by reference in its entirety.

Other examples of primary amine compounds that can be administered in combination with the agent are selected from the group consisting of: 5-amino-2,3-dihydrophthalazine-1,4-dione, 3,4-diethoxyaniline, 1-isopropyl-2-methyl-benzimidazol-5-amine, N2-(4-dimethylaminophenyl)-1,3-benzothiazole-2,6-diamine, N-[(3-aminophenyl)methyl]-6-methoxy-chroman-4-amine, 1-[[4-(aminomethyl)phenyl]methyl]hexahydropyrimidin-2-one, 1-(2,4-diphenylpyrimidin-5-yl)ethanamine, 3-(5-aminopentyl)-1-[(E)-(5-nitro-2-furyl)methyleneamino]imidazolidine-2,4-dione, 2-amino-N-[1-[[1-[(2-amino-1-benzyl-2-oxo-ethyl)carbamoyl]-2-methyl-propyl]carbamoyl]-3-methyl-butyl]-4-methyl-pentanamide, 2-(2-furyl)bicyclo[2.2.1]hept-5-en-3-amine, 5-(3-aminophenyl)furan-2-carboxamidine, 3-(3-aminopropanoyl)-1-[(E)-[5-(4-methoxyphenyl)-2-furyl]methyleneamino]imidazolidine-2,4-dione, 4-amino-N-(2-amino-2-oxo-ethyl)benzamide, 4-amino-N-[2-oxo-2-[(2-oxooxazolidin-3-yl)amino]ethyl]benzamide, (1S,2S,4R)-2-amino-4-isopropenyl-1-methyl-cyclohexanol, 2-amino-4-benzyl-phenol, (3S,5R,8R,9S,10S,13R,14S)-14-amino-3-hydroxy-10,13-dimethyl-1,2,3,4,5,6,7,8,9,11,12,15,16,17-tetradecahydrocyclopenta[a]phenanthrene-17-carboxylic acid, methyl (3S,5R,8R,9S,10S,13R,14S)-14-amino-3-[(2S,5R)-5-hydroxy-6-methyl-tetrahydropyran-2-yl]oxy-10,13-dimethyl-1,2,3,4,5,6,7,8,9,11,12,15,16,17-tetradecahydro-cyclopenta[a]phenanthrene-17-carboxylate, 1-[(E)-[5-(4-aminophenyl)-2-furyl]methyleneamino]-3-[4-(4-methylpiperazin-1-yl)butyl]imidazolidine-2,4-dione, 4-amino-2-hydroxy-benzoic acid, fluoranthen-3-amine, phenazine-2,3-diamine, 3-chloro-4-(4-chlorophenoxy)aniline, 4-(6-methyl-1,3-benzothiazol-2-yl)aniline, 3-[5-(1H-benzimidazol-2-yl)-2-furyl]aniline, N-(2-aminoethyl)-7-tert-butyl-3,3-dimethyl-2H-benzofuran-5-carboxamide, N'-benzylpropane-1,3-diamine, 5,6-dihydro-2-methyl-4H-pyrrolo[3,2,1-ij]quinoline-1-propanamine, 5-(4-aminophenyl)-2-(o-tolyl)pyrazol-3-amine, (2,3-dimethyl-1H-indol-5-yl)methanamine, 2,4-dimethyl-6-nitro-aniline, methyl 2-amino-4,5-dimethoxy-benzoate, 2-(5-propyl-1H-indol-3-yl)ethanamine, 2-(7-methoxy-5-nitro-1H-indol-3-yl)ethanamine, 5-amino-2-[(4-carboxyphenyl)carbamoyl]benzoic acid, 5-amino-2-[(3-carboxyphenyl)carbamoyl]benzoic acid, [2-[2-(3-aminobenzoyl)oxyphenyl]phenyl]3-aminobenzoate, [4-[1-[4-(4-aminobenzoyl)oxyphenyl]-1-methyl-ethyl]phenyl]4-aminobenzoate, 4-amino-N'-(4-chlorobenzoyl)benzohydrazide, 3-(4-aminophenyl)propanoic acid, 2,1,3-benzothiadiazole-4,5-diamine, 1H-benzimidazol-2-yl-methanamine, 2-amino-1-[16-(2-aminoacetyl)-1,4,10,13-tetraoxa-7,16-diazacyclooctadec-7-yl]ethanone, methyl 6-(2-aminophenyl)-6-oxo-hexanoate, 2-(3-amino-4-ethyl-phenyl)pyridin-3-ol, (5-amino-6,7-dimethoxy-3-methyl-benzofuran-2-yl)-morpholino-methanone, (3,5-diaminophenyl)methyl N-butylcarbamate, (3,5-diaminophenyl)methyl N-(2,4-dimethoxyphenyl)carbamate, 1-(4-aminophenyl)-3-(3,4-difluorophenyl)-1-phenyl-propan-2-one, N-(2-amino-ethyl)-2-[bis(2-hydroxyethyl)amino]acetamide, (Z)—N-(2-aminoethyl)-3-(1-naphthyl)prop-2-enamide, N-(2-aminoethyl)naphthalene-1-carboxamide, (2-amino-5-chloro-phenyl)-phenyl-methanone, 4-(4-bromophenoxy)aniline, 3-aminophenazin-2-ol, 5-amino-N-butyl-2-hydroxy-benzenesulfonamide, ethyl 2-[(2-aminophenyl)carbamothioylamino]acetate, 2-(2-aminophenyl)sulfanyl-4,6-dimethyl-pyridine-3-carbonitrile, 2-amino-1-phenyl-ethanone, 2-(2-methylphenoxy)aniline, (2-amino-5-chloro-phenyl)-(2-chlorophenyl)methanone, (1-phenylcyclopentyl)methanamine, tetralin-5-amine, 2-amino-3-(2-hydroxyphenyl)propanoic acid, 3-aminopropane-1-sulfinic acid, (3R,4R,5R)-2-[(1S,2S)-4,6-diamino-3-[(2R,3R)-3-amino-6-[1-(methylamino)ethyl]tetrahydropyran-2-yl]oxy-2-hydroxy-cyclohexoxy]-5-methyl-4-(methylamino)tetrahydropyran-3,5-diol, 4-ethoxyaniline, N-(4-amino-5-chloro-2-hydroxy-phenyl)benzenesulfonamide, 3-amino-N-(3,5-dichloro-2-hydroxy-4-methyl-phenyl)benzamide, 5,6,7,8-tetrahydrophenanthren-2-amine, 2-amino-N-(2-amino-1-benzyl-2-oxo-ethyl)-3-methyl-pentanamide, 1-benzylpiperidin-4-amine, (2R)-2-amino-3-ethylsulfanyl-propanoic acid, 2-amino-N-[2-(2,5-dioxopiperazin-1-yl)-2-oxo-ethyl]propanamide, 2-amino-3-(1H-imidazol-4-yl)propanamide, 2-amino-N-(2-naphthyl)acetamide, (2-amino-6-methyl-phenyl)-phenyl-methanone, 3-[2-(2-aminoethylamino)ethylamino]propanenitrile, 2-amino-1-(3-bromophenyl)ethanone, (1,1-dioxothiolan-3-yl)methanamine, 2,4,6-tritert-butylaniline, N1,N4-bis(4-amino-2-chloro-phenyl)terephthalamide, 4-[(3,4-diaminophenyl)methyl]benzene-1,2-diamine, 5-methoxy-2-methyl-1,3-benzothiazol-6-amine, 2-(2-methyl-5-nitro-imidazol-1-yl)ethanamine, 1-bromonaphthalen-2-amine, 4-amino-2,6-dibromo-benzenesulfonamide, N'-[(E)-(2-aminophenyl)methyleneamino]-N-(4-chloro-3-nitro-phenyl)oxamide, 2-bromo-4,5-dimethyl-aniline, ethyl 2-[(4-amino-3-nitro-benzoyl)amino]-4,5,6,7-tetrahydrobenzothiophene-3-carboxylate, 4-amino-2-morpholinosulfonyl-phenol, 4-[(4-amino-3,5-diethyl-phenyl)methyl]-2,6-diethyl-aniline, 5-[1-(3-amino-4-methyl-phenyl)-2,2,2-trifluoro-1-(trifluoromethyl)ethyl]-2-methyl-aniline, 4-pyridylmethanamine, 2-phenylbenzotriazole-4,5-diamine, 5-amino-2-hydroxy-N,N-dimethyl-benzenesulfonamide, methyl 2-amino-3-phenyl-propanoate, 4-amino-N-[4-[6-[(4-aminobenzoyl)amino]-7-chloro-1H-benzimidazol-2-yl]phenyl]benzamide, 3-chloro-4-(2-naphthyloxy)aniline, 2-bromo-6-(difluoromethylsulfonyl)-4-nitro-aniline, 5-(4-aminophenoxy)-2-(1-naphthyl)isoindoline-1,3-dione, 5-(3-aminophenoxy)-2-(1-naphthyl)isoindoline-1,3-dione, 7-[3-(aminomethyl)-1-piperidyl]-1-cyclopropyl-8-methoxy-4-oxo-quinoline-3-carboxylic acid, 7-[3-(1-amino-1-methyl-ethyl)-1-piperidyl]-1-cyclopropyl-8-methoxy-4-oxo-quinoline-3-carboxylic acid, N-(3-amino-4-chloro-phenyl)-4,4-dimethyl-3-oxo-pentanamide, (4-aminophenyl)-(4-fluorophenyl)methanone, 2-(5-fluoro-1H-indol-3-yl)ethanamine, N1-(4-methoxyphenyl)benzene-1,4-diamine, 2-nitro-5-piperazin-1-yl-aniline, 5-(4-methylpiperazin-1-yl)-2-nitro-aniline, 2-amino-N—[(Z)-1-(4-chlorophenyl)ethylideneamino]benzamide, 3-amino-N-(2-amino-5-methyl-phenyl)-N-benzyl-benzamide, 1-[(Z)-1-(4-aminophenyl)ethylideneamino]-3-(m-tolyl)thiourea, 2-amino-4-cyclopropyl-6-(4-methoxyphenyl)benzene-1,3-dicarbonitrile, 2-(2-naphthyl)-1,3-benzoxazol-5-amine, N-[(E)-1-(4-aminophenyl)ethylideneamino]furan-2-carboxamide, 4-(4-aminophenyl)thiazol-2-amine, (2R)-2-acetamido-6-[[(2R)-2-aminobutanoyl]amino]-N-[[3-(trifluoromethyl)phenyl]methyl]hexanamide, (4S)-5-[[(5R)-5-acetamido-6-oxo-6-(propylamino)hexyl]amino]-4-amino-5-oxo-pentanoic acid, N-[(1R)-5-[[4-(aminomethyl)cyclohexanecarbonyl]amino]-1-[[(2R)-2-hydroxypropyl]carbamoyl]pentyl]thiophene-2-carboxamide, N-[(1R)-1-(allylcarbamoyl)-5-[(4-aminobenzoyl)amino]pentyl]thiophene-2-carboxamide, (4S)-4-amino-5-oxo-5-[[(5R)-6-oxo-6-[2-(2-thienyl)ethylamino]-5-(thiophene-2-carbonylamino)hexyl]amino]pentanoic acid, 2-[(6-amino-1,3-benzothiazol-2-yl)sulfanyl]-N-(2-fluorophenyl)acetamide, N-(5-amino-2-methoxy-phenyl)-2,4-dichlorobenzamide, N-(6-amino-4-methyl-1,3-benzothiazol-2-yl) acetamide, 3-amino-N'-[2-(2-naphthyloxy)acetyl]-5-nitro-benzohydrazide, 2-(2-aminophenyl)sulfanyl-N-[3,5-bis(trifluoromethyl)phenyl]-2-phenyl-acetamide, ethyl 2-[[2-[2-[[2-amino-3-(4-hydroxyphenyl)propanoyl]amino]propanoylamino]acetyl]amino]acetate, 2-amino-5-chloro-N-(4-pyridylmethyl)benzamide, 8-nitronaphthalen-1-amine, 2-amino-3-cyclopropyl-propanoic acid, 2-(2-isopropyl-5-methyl-phenoxy)ethanamine, 2-amino-N-[(E)-1-(2-hydroxyphenyl)ethylideneamino]benzamide, (2R)-2-amino-3-benzhydrylsulfanyl-propanoic acid, tert-butyl 2-aminopropanoate, 2-[4-(1-ethylpropyl)phenoxy]-5-(trifluoromethyl)aniline, N1-methylbenzene-1,3-diamine, 1-(4-aminophenyl)sulfanyl-3-(diethylamino)propan-2-ol, N-(4-aminophenyl)-2,2-dimethyl-propanamide, 2-amino-3-(4-nitrophenyl)butanoic acid, 2-(2-amino-5-bromo-phenyl)-4-methyl-benzo[g]quinoxalin-3-one, N-[3-[(2-aminophenyl)methylamino]-1-methyl-3-oxo-propyl]-2-phenyl-quinoline-4-carboxamide, N-[2-[(2-aminophenyl)methylamino]-2-oxo-1-phenyl-ethyl]-2-phenyl-quinoline-4-carboxamide, (5S)-5-(4-aminobutyl)-3-[4-(o-tolyl)phenyl]imidazolidine-2,4-dione, (5S)-5-(4-aminobutyl)-3-[4-(benzothiophen-2-yl)-1-naphthyl]-2-thioxo-imidazolidin-4-one, 2-amino-4,6-ditert-butyl-phenol, 5-(aminomethyl)-2,4-dimethyl-pyridin-3-amine, 3-amino-N-[5-hydroxy-1-(2,4,6-trichlorophenyl)pyrazol-3-yl]benzamide, (2R)-2-amino-3-(4-fluorophenyl)-N-[4-guanidino-1-(1-piperidylmethyl)butyl]propanamide, 3-[[2-[2-(3-aminopropylcarbamoyl)phenyl]benzoyl]-[(2,5-difluorophenyl)methyl]amino]propanoic acid, N-[(4-acetamidophenyl)methyl]-N-(3-amino-2,2-dimethyl-propyl)-2-(4-ethylphenyl)pyridine-4-carboxamide, N-(3-aminopropyl)-2-(4-ethylphenyl)-N-[(3,4,5-trimethoxyphenyl)methyl]pyridine-4-carboxamide, N-(2-aminoethyl)-5-(4-fluorophenyl)-N-(2-pyridylmethyl)pyridine-3-carboxamide, N-[[4-(aminomethyl)phenyl]methyl]-5-(1-naphthyl)-N-(2-pyridylmethyl)pyridine-3-carboxamide, 2-(3-acetylphenyl)-N-(3-aminopropyl)-N-(2,3-dihydro-1,4-benzodioxin-6-ylmethyl)pyridine-4-carboxamide, 2-[(4S,5R)-2-[(1R)-1-amino-2-(4-fluorophenyl)ethyl]-5-(2-naphthyl)tetrahydropyran-4-yl]acetonitrile, (2R)-2-amino-1-[(2S,4R)-4-benzyloxy-2-[2-(1,2,4-triazol-4-yl)ethyl]pyrrolidin-1-yl]-3-(4-fluorophenyl)propan-1-one, (2R)-2-amino-3-phenyl-1-[4-phenyl-4-(1,2,4-triazol-1-ylmethyl)-1-piperidyl]propan-1-one, N'-cyclododecylethane-1,2-diamine, 7-[2-[(2-amino-2-methyl-propyl)amino]pyrimidin-4-yl]-6-(4-fluorophenyl)-2,3-dihydro-1H-pyrazolo[1,2-a]pyrazol-5-one, 2,3,4,5-tetrahydro-1-benzothiepin-5-amine, 5-[(2R,3R,4S)-3-amino-4-(methoxycarbonylamino)tetrahydrothiophen-2-yl]pentanoic acid, 3-(2-aminophenyl)sulfanyl-3-(3,4-dichlorophenyl)-1-phenyl-propan-1-one, and pharmaceutically acceptable salts thereof.

The invention is further illustrated by the following examples, which are not intended to limit the scope of the claims.

Example 1

In this Example, we investigated the in vivo signaling mechanisms that mediate the action of atRAL in causing ROS production and light-induced photoreceptor degeneration. The results indicate that PLC activation and the resulting second messenger $IP_3$ contribute to atRAL-induced NADPH oxidase activation. The toxic action of atRAL was diminished by blocking serotonin 2A ($5-HT_{2A}R$) or $M_3$-muscarinic ($M_3R$) receptors, implicating G protein-coupled receptors GPCR(s) participation in the overall process. These observations show that certain types of retinal degeneration are be prevented by therapies selectively targeting transient sequestration (buffering) of elevated atRAL, antagonizing a subset of GPCRs, or inhibiting PLC, $IP_3R$ or NADPH oxidase, alone or in combination.

Methods

Animals $Abca4^{-/-}Rdh8^{-/-}$ mice, generated and genotyped as previously described were used when they reached 4- to 5-weeks of age. Eight- to 12-week old Balb/c mice were obtained from Jackson Laboratory (Bar Harbor, Me.). All mice were housed in the Animal Resource Center at the School of Medicine, Case Western Reserve University, where they were routinely maintained in a 12 h light (less than 50 lux in the cage)/12 h dark cycle environment. For bright light exposure experiments mice were dark-adapted for 24 h prior to illumination at 10,000 lux (150 W spiral lamp, Commercial Electric) for either 30 min ($Abca4^{-/-}Rdh8^{-/-}$ mice) or 2 h (Balb/c mice). $Abca4^{-/-}Rdh8^{-/-}$ mouse pupils were dilated with 1% tropicamide prior to light exposure whereas Balb/c mice did not require pupil dilation before such exposure. Analyses of retinal structural and functional changes were performed 7 days after bright light exposure. All animal handling procedures and experiments were approved by the Institutional Animal Care and Use Committee at Case Western Reserve University.

Chemicals atRAL was purchased from Toronto Research Chemicals, Inc (Toronto, Canada). all-trans-Retinoic acid (atRA), Apocynin (APO), diphenyliodonium (DPI), 2-aminoethoxydiphenyl borate (2-APB), ketanserin and 8-hydroxy-N,N-dipropyl-2-aminotetralin (8-(OH)-DPAT) were obtained from Sigma (St. Louis, Mo.). R and S enantiomer of pregablin was synthesized by Ricerca Bioscience LLC (Concord, Ohio). A2E (2) and Ret-$NH_2$ (3) were synthesized as previously described (3). U-73122 was purchased from Calbiochem (Gibbstown, N.J.). Ritanserin and 1,1-dimethyl-4-diphenylacetoxypiperidinium iodide (4-DAMP) were purchased from TOCRIS (Ellisville, Mo.).

In Vitro Detection and Quantification of Intracellular Reactive Oxygen Species (ROS)

ARPE19 cells were cultured in Dulbecco's Modified Eagle's Medium (DMEM) (low glucose) supplemented with 10% fetal bovine serum. The ROS probes, 2',7'-dichlorofluorescein diacetate (DCF-DA, Sigma, St. Louis, Mo.) or dihydroethidium (DHE, Invitrogen Corporation, Carlsbad, Calif.) were added after indicated pretreatments and incubated at 37° C. for 10-min before thorough washing in PBS and the ROS signals were subsequently observed at the same exposure setting under an inverted fluorescence microscope (Leica DMI 6000 B). Fluorescence quantification was performed with Metamorph imaging software (Molecular Devices, Downington, Pa.). Thresholds corresponding to fluorescent signals were set from the images and average fluorescence intensities were recorded for statistical analysis.

In Vivo Detection of ROS

The ROS probe, DHE, at a dose of 20 mg/kg body weight was administered to $Abca4^{-/-}Rdh8^{-/-}$ mice via intraperitoneal injection 30 min prior to light exposure. Eye cups obtained after removing the cornea, lens and vitreous body from enucleated eye globes 3 h post light illumination were fixed in 4% paraformaldehyde. Cryosections were prepared from fixed eye cups and cut at 12 μm thickness for microscopic assessment of ROS signal fluorescence in the retina.

Mouse Treatments

Ret-NH$_2$ and R and S enantiomer of pregablin were administered by gavage to 24-h dark-adapted mice at a dose of 100 mg/kg body weight 2 h before the illumination. All other experimental compounds were given to 24 h dark-adapted mice by intraperitoneal injection through a 28 gauge needle at 24 h and 1 h prior to bright light exposure. Tested compounds and their doses were: APO, 50 mg/kg body weight; DPI, 1 mg/kg body weight; U-73122, 6.25 mg/kg body weight; 2-APB, 2.5 mg/kg body weight; ketanserin, 1.25 mg/kg body weight; ritanserin, 3.75 mg/kg body weight; 8-(OH)-DPAT, 10 mg/kg body weight; and 4-DAMP, 6.25 mg/kg body weight.

Optical Coherence Tomography (OCT)

Ultra-high resolution SD-OCT (Bioptigen, Research Triangle Park, N.C.) was performed for in vivo imaging of mouse retinas. Mice were anesthetized by intraperitoneal injection of an anesthetic cocktail of ketamine (6 mg/ml) and xylazine (0.44 mg/ml) diluted with 10 mM sodium phosphate, pH 7.2, 100 mM NaCl at the dose of 20 μl/g body weight. Pupils were dilated with 1% tropicamide prior to imaging. Four frames of OCT images were acquired in the B-mode and averaged for presentation.

Histology and Immunohistochemistry

Retinal histology and immunohistochemistry (IHC) was performed as previously described. Briefly, eye cups free of cornea, lens and vitreous body were fixed in 2% glutaraldehyde/4% paraformaldehyde and processed for Epon embedding. Sections 1 μm thick were cut and stained with toluidine blue for histological examination under a light microscope. IHC analysis was performed on 12 μm thick cryosections prepared from 4% paraformaldehyde-fixed eye cups. Collected cryosections were subjected to examination for rhodopsin, PNA and DAPI expression.

ERGs

All ERG procedures were performed by published methods. For single-flash recording, the duration of white light flash stimuli (from 20 μs to 1 ms) was adjusted to provide a range of illumination intensities (from −3.7 to 1.6 log cd·s/m$^2$). Three to 5 recordings were made at sufficient intervals between flash stimuli (from 3 s to 1 min) to allow recovery from any photo-bleaching effects.

Retinoid Analyses

Extraction, derivatization, and separation of retinoids were performed and 11-cis-retinoid content was analyzed by HPLC by procedures previously described.

Statistical Analyses

Results were collected from at least three independent experiments. Data were expressed as means±SEM and statistical analyses were performed using the students t-test.

Results atRAL Stimulates Intracellular ROS Production Through NADPH Oxidase

Figure 5:
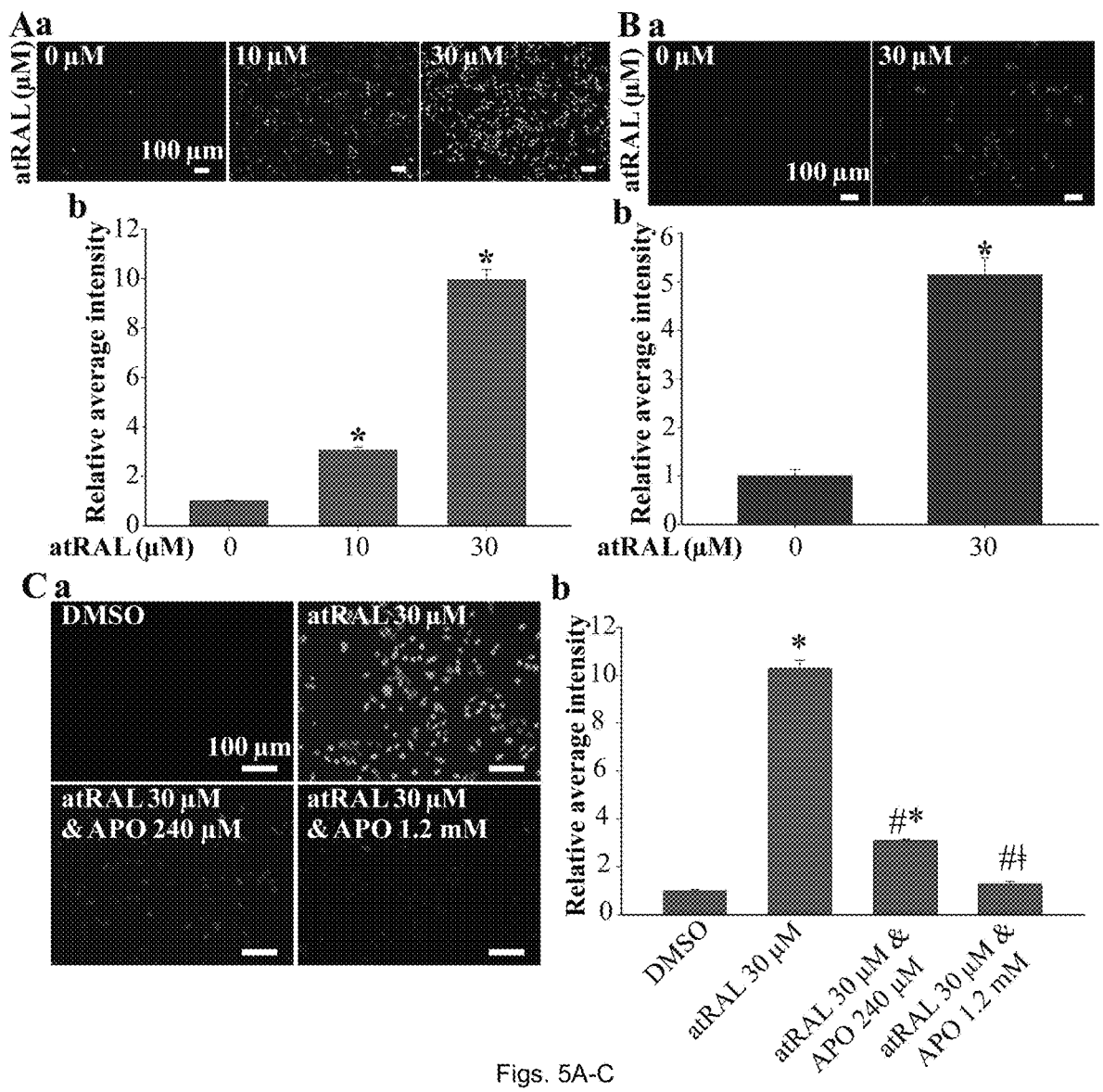
FIGS. 5(A-C) illustrate: (A) (a) images of the ROS signal obtained with the same exposure time under a fluorescence microscope, and (b) average fluorescence intensities recorded and compared with Metamorph imaging software for statistical analyses (Means±SEM; *compared to 0 μM, p<0.01); (B) (a) images of the ROS signal detected by DHE were obtained under a fluorescence microscope. (b) Recorded ROS signals were then compared using by the method described above. (C) atRAL and/or the NADPH oxidase inhibitor, Apocynin (APO) was applied to cultured ARPE19 cells at concentrations indicated. ROS generation was monitored 1 h after indicated treatments via DCF-DA detection as noted above. (a) Fluorescence images were recorded with the same exposure times, and (b) statistical analyses were performed as noted above (* compared to control, p<0.01; # compared to atRAL 30 μM, p<0.01; ‾ compared to control, p>0.05).

To determine the effect of atRAL on retinal ROS production, we incubated ARPE19 cells, an immortalized human RPE-like cell line susceptible to atRAL-induced cell death, with atRAL followed by examination with a ROS probe. As shown in FIG. 5A, atRAL application significantly elevated intracellular ROS production prior to massive cell death in a dose dependent manner. Because the probe used, 5-(and-6)-chloromethyl-2',7'-dichlorodihydrofluorescein diacetate (DCF-DA), is not entirely selective for H$_2$O$_2$ and hydroxyl radicals, intracellular ROS levels were also examined by another commonly used ROS probe, dihydroethidium (DHE), which is especially sensitive to superoxide. Consistently, the intracellular ROS signal examined by the DHE probe was markedly increased in ARPE19 cells treated with atRAL at 30 μM (FIG. 5B), a dose that reproducibly causes excessive ARPE19 cell death as reported previously. This concentration of atRAL would be produced by a ~1% bleach of rhodopsin under physiological conditions. Interestingly, atRAL-related metabolic products such as all-trans-retinol (atROL), all-trans-retinoic acid (atRA) and A2E did not induce overproduction of intracellular ROS (FIG. 12). The differences between atRAL and the other retinoids in triggering intracellular ROS production may explain the difference in their effect on inducing cell death, as neither atROL, atRA nor A2E induced cell death at the doses examined.

It is known that NADPH oxidase is the primary enzymatic source of atRAL-stimulated superoxide generated in neutrophils. To further explore the involvement of NADPH oxidase in atRAL-induced ROS production in retinal cells, APO, a widely used NADPH oxidase inhibitor that interrupts NADPH oxidase complex assembly, was applied to ARPE19 cells together with atRAL. As shown in FIG. 4C, APO treatment inhibited atRAL-induced intracellular ROS generation which was associated with improved ARPE19 cell survival (FIG. 12). Taken together, these results indicate that NADPH oxidase is required for atRAL-induced ROS production in ARPE19 cells, a finding that implies a mechanistic involvement of NADPH oxidase-mediated ROS generation in atRAL-induced retinal cell death.

Figure 6:
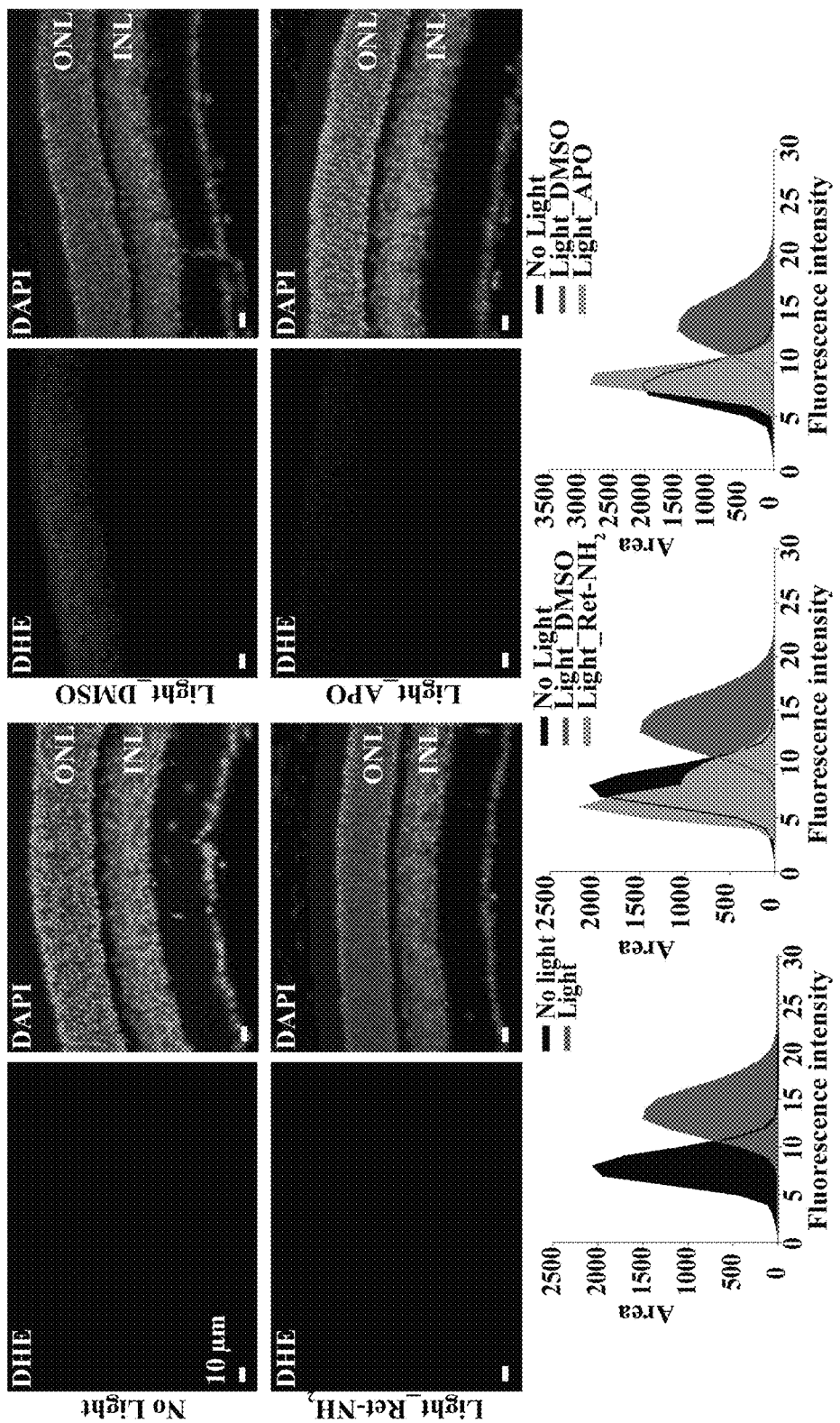
FIG. 6 illustrates atRAL is associated with NADPH oxidase-mediated ROS generation in photoreceptors. Dark-adapted $Rdh8^{-/-}Abca4^{-/-}$ mice at age of 4 to 5 weeks were treated with the ROS probe, DHE, prior to light exposure at 10,000 lux for 30 min. DMSO vehicle control (Light_DMSO) and NADPH oxidase inhibitor, APO (Light_APO)

NADPH Oxidase Mediates Light-Induced ROS Production in Rdh8$^{-/-}$Abca4$^{-/-}$ Mouse Retina To further test the observation that atRAL induces ROS overproduction through NADPH oxidase in vivo, the ROS probe DHE was administered to Abca4$^{-/-}$Rdh4$^{-/-}$ mice 30 min before light exposure at 10,000 lux for 30 min. This regimen was selected because this intensity of illumination causes marked photoreceptor degeneration in Abca4$^{-/-}$Rdh8$^{-/-}$ mice, whereas wild type controls manifest no obvious morphological changes (FIG. 13). Compared to the ROS signal detected in the outer nuclear layer (ONL) of Abca4$^{-/-}$Rdh8$^{-/-}$ mice unexposed to light, a strong ROS signal was recorded in the ONL of retinas from light-exposed and vehicle only treated Abca4$^{-/-}$Rdh8$^{-/-}$ mice (FIG. 6). When APO was administered 1 h prior to illumination, these APO-treated Abca4$^{-/-}$Rdh8$^{-/-}$ mice displayed substantially decreased ROS production in the ONL with an intensity similar to that observed in retinas from non-light exposed Abca4$^{-/-}$Rdh8$^{-/-}$ mice (FIG. 6). In addition, diphenyleneiodonium (DPI), another commonly used NADPH oxidase inhibitor structurally different from APO, exhibited a similar effect on ROS production in light-challenged Abca4$^{-/-}$Rdh8$^{-/-}$ mice (FIG. 15). The association of atRAL with ROS production in vivo was further confirmed by pretreating light-exposed Abca4$^{-/-}$Rdh8$^{-/-}$ mice with all-trans-retinylamine (Ret-NH$_2$), a retinal scavenger and retinoid cycle inhibitor. Ret-NH$_2$ significantly decreased ROS production as well (FIG. 6). This effect was also consistently observed in mice pretreated with R and S enantiomer of pregabalin, which also reduced free atRAL (FIG. 15). Together, these results demonstrate that atRAL promotes ROS production in photoreceptors upon light exposure. This effect is mediated by NADPH oxidase, suggesting that atRAL-induced NADPH oxidase-mediated ROS generation could be involved in the pathogenesis of acute light-induced photoreceptor degeneration.

Inhibition of NADPH Oxidase Protects Retinal Morphology Against Acute Light-Induced Photoreceptor Degeneration in Rdh8$^{-/-}$Abca4$^{-/-}$ Mice To examine directly if atRAL-induced NADPH oxidase-mediated ROS production is mechanistically implicated in acute light-induced photoreceptor degeneration, Abca4$^{-/-}$ Rdh8$^{-/-}$ mice were treated with APO, DPI or a vehicle control (DMSO) 1 h prior to light exposure at 10,000 lux for 30 min. The effect of NADPH oxidase inhibitor treatment was assessed 7 days after illumination. Optical coherence tomography (OCT) scans revealed significantly disrupted photoreceptor structure in DMSO-treated mice. OCT of both APO-treated (FIG. 7Aa) and DPI-treated (data not shown) mice exhibited well-preserved retinal morphology compared to that of the vehicle-treated controls. This observation was supported further by retinal histological examination. In agreement with the OCT images, retinas from DMSO-treated mice manifested prominent structural disarrangement with shortened lengths of photoreceptor outer segment/inner segment, markedly decreased cell numbers in the ONL and increased pyknosis of photoreceptor nuclei. This morphology contrasted sharply with the nearly intact retinal morphology manifested by APO-treated (FIG. 7Ab) or DPI-treated mice (FIG. 7Ba). Immunohistochemical examination for rhodopsin in rod photoreceptor outer segments and peanut agglutinin lectin (PNA)-labeling of cone cell matrix sheaths was also performed. These images revealed abundant and organized expression of rhodopsin and PNA in APO-treated (FIG. 7Ac) or DPI-treated (data not shown) mice, in sharp contrast to the residual pattern of rhodopsin and PNA expression detected in DMSO-treated mice. Quantification of ONL thickness after DAPI staining revealed that both APO (FIG. 7Ad) and DPI (FIG. 7Bb) pretreatment greatly preserved photoreceptors compared to DMSO pretreatment. These results support the notion that NADPH oxidase-mediated ROS generation is mechanistically implicated in the action of atRAL during light-induced photoreceptor degeneration.

Involvement of PLC/IP$_3$/Ca$^{2+}$ Signaling in Light-Induced Photoreceptor atRAL-Mediated Degeneration To test the hypothesis that PLC/IP$_3$/Ca$^{2+}$ signaling is involved in the cascade of events related to atRAL toxicity, we pretreated Abca4$^{-/-}$Rdh8$^{-/-}$ mice with the selective PLC inhibitor, U-73122, prior to light exposure. In contrary to Abca4$^{-/-}$Rdh8$^{-/-}$ mice pretreated with DMSO that reproducibly manifested severe histological photoreceptor degeneration, Abca4$^{-/-}$Rdh8$^{-/-}$ mice pretreated with U-73122 exhibited markedly less light-induced photoreceptor damage (FIG. 8Aa) and ONL thickness measurements provided further evidence of a protective effect (FIG. 8Ab). These results strongly support the involvement of PLC activation in light-induced atRAL-mediated photoreceptor degeneration.

To further validate the involvement of PLC/IP$_3$/Ca$^{2+}$ signaling in atRAL-mediated photoreceptor degeneration in vivo, 2-aminoethoxydiphenyl borate or 2-APB, primarily known as an antagonist of IP$_3$/IP$_3$R mediated Ca$^{2+}$ release was administered to Abca4$^{-/-}$Rdh8$^{-/-}$ mice prior to light exposure. Retinal morphological examination revealed that 2-APB pretreatment significantly preserved retinal morphology after illumination compared to DMSO pretreatment (FIG. 8Ba). Further, 2-APB pretreatment reduced ROS production in light-exposed Abca4$^{-/-}$Rdh8$^{-/-}$ mouse photoreceptors to a level comparable to that observed in photoreceptors of mice without light exposure (FIG. 8Bb). Thus, IP$_3$-mediated Ca$^{2+}$ elevation is mechanistically associated with atRAL-induced ROS production during light-induced photoreceptor degeneration. Taken together, our results demonstrate that the PLC/IP$_3$/Ca$^{2+}$ pathway acts upstream of light-induced atRAL-mediated ROS generation and consequent photoreceptor degeneration.

Involvement of Gq-Coupled Receptors in Light-Induced atRAL-Mediated Retinal Degeneration 5-HT$_{2A}$R has been suggested to be involved in NADPH oxidase activation. Additionally, chronic or acute activation of 5-HT$_{2A}$R causes considerable reduction in 5-HT$_{1A}$R activity. The 5-HT$_{1A}$R was recently shown to be involved in light-induced photoreceptor degeneration because selective 5-HT$_{1A}$R agonists protected the rat retina against photo-oxidative stress. Therefore we hypothesized that increased activation of the 5-HT$_{2A}$R could contribute to the pathogenesis of light-induced photoreceptor degeneration in Abca4$^{-/-}$Rdh8$^{-/-}$ mice, given that it activates PLC and such activation is involved in the in vivo action of atRAL (FIG. 8). To test this hypothesis, Abca4$^{-/-}$Rdh8$^{-/-}$ mice were treated with the selective 5-HT$_{2A}$R antagonist ketanserin prior to light exposure. A substantial protective effect of ketanserin against light-induced photoreceptor degeneration was observed compared to DMSO pretreatment (FIG. 9Aa, b). A similar observation was made when Abca4$^{-/-}$Rdh8$^{-/-}$ mice were treated with another selective 5-HT$_{2A}$R antagonist, ritanserin (FIG. 16). A role for 5-HTRs in light-induced atRAL-mediated retinal degeneration in Abca4$^{-/-}$Rdh8$^{-/-}$ mice is additionally supported by the protective effect of the 5-HT$_{1A}$R agonist, 8-hydroxy-N,N-dipropyl-2-aminotetralin or 8-OH-DPAT (FIG. 17).

Considering that PLC can be activated by multiple Gq-coupled receptors, we address the issue of whether the 5-HT$_{2A}$R is the only GPCR involved in atRAL-induced PLC activation. Interestingly, the M$_3$R antagonist, 1,1-dimethyl-4-diphenylacetoxypiperidinium iodide or 4-DAMP, also was found to preserve retinal morphology in Abca4$^{-/-}$Rdh8$^{-/-}$ mice challenged by acute light exposure (FIG. 9Ba, b), supporting the idea that multiple Gq-coupled receptors could be activated to mediate the effect of atRAL on PLC activation.

Involvement of these mechanisms in light-induced atRAL-mediated photoreceptor degeneration was also shown by improved retinal function of light-challenged Abca4$^{-/-}$Rdh8$^{-/-}$ mice after pretreatment with several pharmacological agents that protected against histological damage. As indicated in FIG. 10 and compared to light-challenged wild type control and Abca4$^{-/-}$ Rdh8$^{-/-}$ mice without light exposure, light-challenged Abca4$^{-/-}$Rdh8$^{-/-}$ mice pretreated with DMSO exhibited decreased amplitudes of both a-waves and b-waves indicating marked impairment of their retinal function. The protective effect of these treatments on retinal function was evidenced by increased a-wave and b-wave amplitudes compared to those observed in DMSO-treated Abca4$^{-/-}$Rdh8$^{-/-}$ mice.

Data presented above were derived from studies with Abca4$^{-/-}$ Rdh8$^{-/-}$ mice, a genetically modified animal model with a deficiency in atRAL transport and clearance owing to targeted deletion of the Rdh8 and Abca4 genes. To determine if the mechanisms proposed were merely secondary to genetic modification or arose from some unidentified off-target effects in Abca4$^{-/-}$Rdh8$^{-/-}$ mice, we tested our hypotheses further in the light-challenged Balb/c mouse, a classical model of light-induced photoreceptor degeneration. Consistently, as compared to unexposed control mice, Balb/c mice acutely exposed to light exhibited severe photoreceptor degeneration evidenced by disrupted retinal histology (FIG. 11A), decreased ocular 11-cis-RAL content (FIG. 18) and impaired retinal function (FIG. 11B). In contrast, pharmacological pretreatment targeting each proposed mechanism displayed significant protection of photoreceptors against acute light-induced degeneration as assessed by morphological (FIG. 11A), biochemical (FIG. 18) and functional tests (FIG. 11B).

Example 2

In this Example, pharmacological compounds targeting multiple GPCRs, which are identified in Table 1 below, were evaluated as potential therapeutic candidates to prevent photoreceptor cells from light-induced degeneration. Various antagonists at multiple Gs-coupled GPCRs prevented photoreceptor cell death, implying that increased functionality of Gs-coupled GPCRs and subsequent activation of adenylyl cyclase (AC) may cause photoreceptor cell death. On the other hand, Gi-coupled GPCRs functionally lead to suppression of AC activity. Agonists activating α2 adrenergic receptor, a Gi-coupled GPCR, prevented photoreceptor death. Therefore, AC as the central player mediating Gs-coupled and Gi-coupled GPCR signaling, could also serve as therapeutic target to preserve photoreceptor during degeneration, which could be achieved by inhibition of AC activity by AC inhibitor.

Methods

Animals $Abca4^{-/-}Rdh8^{-/-}$ mice were generated and genotyped as previously described and were used in the present study when they reached 4- to 5-weeks of age. All mice were routinely maintained in a 12 h light (less than 10 lux)/12 h dark cycle environment in the Animal Resource Center at the School of Medicine, Case Western Reserve University. For bright light exposure experiments, $Abca4^{-/-}Rdh8^{-/-}$ mouse pupils were dilated with 1% tropicamide prior to white light exposure at 10,000 lux (150 W spiral lamp, Commercial Electric) for 30 min. Assessment of retinal structural and functional changes were performed 7 days after light exposure. All mouse handling procedures and protocols were approved by the Institutional Animal Care and Use Committee at Case Western Reserve University.

Chemicals

Doxazosin (DOX) was purchased from Selleckchem (Huston, Tex.). Lofexidine was purchased from Santa Cruz (Santa Cruz, Calif.). Prazosin (PRA), Tamsulosin (TAM), RS 23579-190 (RS), RO 04-6790 (RO), SB 269970 (SB), SGS 518 oxalate (SGS), LY 215840 (LY), Guanabenz (GUB), Guanfacine (GUF) and SQ 22536 (SQ) were ordered from TOCRIS Biosciences (Bristol, United Kingdom).

Mouse Treatments

All the experimental compounds were administered to mice by intraperitoneal injection through a 28 gauge needle at 30 min prior to bright light exposure. Tested compounds and their doses were: DOX, 10 mg/kg body weight (bw); PRA, 2 mg/kg bw; TAM, 2 mg/kg bw; RS, 20 mg/kg bw; RO, 30 mg/kg bw; SB, 30 mg/kg bw; SGS, 30 mg/bw; LY, 10 mg/kg bw; GUB, 2 mg/kg bw; GUF, 2 mg/kg bw; LOF, 2 mg/kg bw; SQL 0.083 mg/kg bw; SQ2, 0.125 mg/kg bw; SQ3, 0.25 mg/kg bw; SQ4: 0.5 mg/kg bw.

Optical Coherence Tomography (OCT)

Non-invasive ultra-high resolution SD-OCT (Bioptigen, Research Triangle Park, N.C.) was performed for in vivo imaging of mouse retinas. Mice were anesthetized with by intraperitoneal injection of anesthetic cocktail of ketamine (6 mg/ml) and xylazine (0.44 mg/ml) diluted with 10 mM sodium phosphate, pH 7.2, 100 mM NaCl at the dose of 20 µl/g bw. Pupils were dilated with 1% tropicamide prior to SD-OCT imaging. Five frames of OCT images were acquired in the B-mode and averaged for image presentation.

Scanning Laser Ophthalmoscopy (SLO)

SLO (Heidelberg Engineering, Heidelberg, Germany) was carried out for whole fundus imaging of mouse retinas. Mice were anesthetized by intraperitoneal injection of anesthetic cocktail indicated above, which was followed by pupil dilation using 1% tropicamide prior to SLO imaging under autofluorescence mode.

Immunohistochemistry

Retinal immunohistochemistry (IHC) was carried out as previously described. Briefly, eyes were enucleated and eye cups were made to eliminate cornea, lens and vitreous body and fixed in 4% paraformaldehyde and processed for cryosectioning. 12 µm thick cryosections were collected cryosections and subjected to examination for rhodopsin, peanut agglutinin lectin (PNA) and DAPI expression.

ERGs

ERGs were performed as previously described. Briefly, dark-adapted mice were examined under dim red light transmitted through a Kodak No. 1 Safelight filter (transmittance 560 nm). Pupils were dilated with 1% tropicamide under anesthesia induced by method described above. Contact lens electrodes were placed on the eyes, and a reference electrode and ground electrode were positioned on the ear and tail, respectively. ERGs were recorded with the universal testing and electrophysiologic system, UTAS E-3000 (LKC Technologies, Inc. Gaithersburg, Md.).

Statistical Analyses

Results were collected from at least 4 mice per experimental group. Data were expressed as means±SEM and statistical analyses were performed using the Students t-test or ANOVA.

Results

Pharmacological Compounds Targeting α1 Adrenergic Receptor, a Gq-Coupled GPCR Preserves Retinas Against Light-Induced Retinopathy in $Abca4^{-/-}Rdh8^{-/-}$ Mice Pharmacological compounds antagonizing α1 adrenergic receptor (α1R), a class of Gq-coupled GPCR, were evaluated for the effect on light-induced retinopathy. α1R antagonists including Doxazosin (DOX), Prazosin (PRA) and Tamsulosin (TAM) were independently tested in $Abca4^{-/-}Rdh8^{-/-}$ mice, which displayed severe light-induced retinopathy as previously reported. DOX, PRA or TAM was administered to $Abca4^{-/-}Rdh8^{-/-}$ mice at the age of 4- to 5-weeks prior to the exposure to white light at the intensity of 10,000 Lux for 30 min. The effects of each treatment were first evaluated by non-invasive OCT imaging. As shown in FIG. 19A, compared to severely disrupted photoreceptor structure manifested by $Abca4^{-/-}Rdh8^{-/-}$ mice treated with DMSO vehicle control and exposed to intense light, substantial protection on photoreceptor morphology was observed when light-exposed $Abca4^{-/-}Rdh8^{-/-}$ mice were pre-treated by DOX, PRA or TAM, respectively. SLO imaging on autofluorescence mode was also carried out to assess light-induced photoreceptor damage in DMSO-treated $Abca4^{-/-}Rdh8^{-/-}$ mice and those pre-treated by DOX, PRA or TAM. As shown in FIG. 19B, numerous autofluorescence spots were readily observed in $Abca4^{-/-}Rdh8^{-/-}$ mice treated by DMSO 8-days after light exposure, which is typical of light-induced photoreceptor damage. In distinct contrast, treatment of DOX, PRA or TAM significantly protected retinas from developing light-induced damage revealed by SLO imaging, which is consistent with the data collected from OCT imaging. These results therefore provide experimental evidence that α1 adrenergic receptor could be viewed as a valid therapeutic target in the intervention of light-induced retinopathy.

Pharmacological Compounds Targeting Multiple Gs-Coupled GPCRs Protects Retinas from Light-Induced Retinopathy in Abca4$^{-/-}$Rdh8$^{-/-}$ Mice To further evaluate the therapeutic potential targeting other types of GPCRs, we also examined the effect of multiple antagonists against GPCRs that are coupled to Gs. Antagonists blocking the activation of 5-HT4 receptor, RS 23579-190 (RS), 5-HT6 receptor, RO 04-6790 (RO) and SGS 518 (SGS), 5-HT7 receptor, SB 269970 (SB) and LY 215840 (LY) were individually tested in Abca4$^{-/-}$Rdh8$^{-/-}$ light-induced retinopathy model. Each of the compounds was administered to 4- to 5-week old Abca4$^{-/-}$Rdh8$^{-/-}$ mice 30 min before white light exposure at 10,000 Lux for 30 min. OCT imaging was performed 7 days later to evaluate the retinal structural changes. In contrast to dramatically damaged photoreceptor structure displayed by DMSO-treated, light-exposed Abca4$^{-/-}$Rdh8$^{-/-}$ mice, profound preservation of photoreceptor morphology was observed in Abca4$^{-/-}$Rdh8$^{-/-}$ treated with compounds blocking the activation of Gs-coupled GPCRs such as 5-HT4 receptor, 5-HT6 receptor and 5-HT7 receptor, respectively (FIG. 20A). The protective effects of indicated compounds were further supported by significantly reduced formation of autofluorescence spots in Abca4$^{-/-}$Rdh8$^{-/-}$ mice treated with antagonists against these receptors (FIG. 20B). Our results indicated that Gs-coupled GPCRs could be further explored as plausible therapeutic target in degenerative photoreceptor disorders.

Pharmacological Compounds Activating α2 Adrenergic Receptor, a Gi-Coupled GPCR Provide Significant Protection Against Light-Induced Retinopathy in Abca4$^{-/-}$Rdh8$^{-/-}$ Mice α2 adrenergic receptor (α2R), a Gi-coupled GPCR was evaluated as well to address the possibility of serving as therapeutic candidate treating photoreceptor degeneration. Agonists activating α2R including Guanabenz (GUB), Guanafacine (GUF) and Lofexidine (LOF) was each administered 30 min prior to bright light exposure of Abca4$^{-/-}$Rdh8$^{-/-}$ mice. OCT images were taken 7 days after light exposure. As shown in FIG. 21A, compared to the photoreceptor disruption manifested by DMSO-treated mice, light-induced retinal morphological damage was significantly prevented by treatment of GUB, GUF or LOF. Furthermore, markedly less autofluorescence spots indicative of light-induced photoreceptor damage were observed in mice treated with GUB, GUF or LOF, which is in sharp contrast to large amount of autofluorescence spots presented by DMSO-treated mice (FIG. 21B).

Inhibition of Adenylyl Cyclase Prevents Retinas from Developing Light-Induced Degeneration Our data have demonstrated that multiple antagonists against Gs-coupled GPCRs or agonists at Gi-coupled GPCRs protect retinas against light-induced degeneration. Given that adenylyl cyclase (AC) is the central player mediating the intracellular function of both Gs- and Gi-coupled GPCRs, we further tested the possibility of targeting AC in intervening light-induced retinal degeneration. To address this, AC specific inhibitor SQ 22536 (SQ) was administered to Abca4$^{-/-}$Rdh8$^{-/-}$ mice 30 min before bright light exposure, followed by retinal structural examination by OCT imaging 7 days later. As shown in FIG. 22A, SQ treatment protected retinas from light-induced degeneration in a dose-dependent manner. Further SLO evaluation also showed a dose-dependent effect of SQ on preventing the formation of autofluorescent spot signifying of light-induced photoreceptor damage (FIG. 22B). These data indicate that AC is involved in the pathogenesis of light-induced retinal degeneration and support the notion that AC signaling is a valid target for treating light-induced retinal degeneration.

Retinal Morphological Preservation by Pharmacological Intervention Targeting Gq-, Gi-, Gs-Coupled GPCRs and AC Immunohistochemical examination was also performed to evaluate the retinal morphological alterations in detail. Rhodopsin, which labels rod outer segment, peanut agglutinin, which immunohistochemically marks cone cell matrix sheaths in retina, and DAPI, which stains nucleus, were applied to retinal sections collected from Abca4$^{-/-}$Rdh8$^{-/-}$ mice. As shown in FIG. 23, compared to severely damaged photoreceptor structure manifested by light-exposed, Abca4$^{-/-}$Rdh8$^{-/-}$ mice treated with DMSO vehicle, which exhibited residual expression of Rhodopsin and peanut agglutinin and marked decreased thickness of DAPI-stained photoreceptor outer nuclear layer, substantially preserved photoreceptor morphology was evidenced by abundant, well-organized Rhodopsin, peanut agglutinin expression and well-maintained DAPI-stained outer nuclear layer in Abca4$^{-/-}$Rdh8$^{-/-}$ mice treated by pharmacological compounds targeting either Gq- (DOX, PRA and TAM), Gi- (LY, GUB and GUF), Gs- (RS, SGS, RO and LY) coupled GPCRs or AC (SQ).

Protection of Retinal Function by Pharmacological Intervention Targeting Gq-, Gi-, Gs-Coupled GPCRs and AC To further estimate the therapeutic effects of pharmacological treatment that proved to be effective in preserving the retinal morphology, electroretinography was performed 2 weeks after indicated pharmacological pre-treatment and light exposure. As shown in FIG. 23, compared to the mice without light exposure (no light), bright light exposure at 10,000 Lux for 30 min nearly abolished scotopic ERG response in Abca4$^{-/-}$Rdh8$^{-/-}$ mice treated with DMSO vehicle. In sharp to contrast to the ERG response displayed by DMSO-treated mice, substantial preservation of the scotopic ERG response was achieved by treatment targeting multiple GPCRs, including DOX, a compound antagonizing Gq-coupled α1R; RS, a compound antagonizing Gs-coupled 5-HT4 receptor; RO, a compound antagonizing Gs-coupled 5-HT6 receptor; LY, a compound antagonizing 5-HT7 receptor; LOF, a compound activating Gi-coupled α2R and SQ, an inhibitor of AC. Our data indicate that pharmacological treatment targeting these GPCRs exerts protection against light-induced retinal degeneration at functional level as well.

The following Table lists the effectiveness of pharmacological compounds targeting multiple GPCRs evaluated as potential therapeutic candidates to prevent photoreceptor cells from light-induced degeneration as measured by OCT imaging of Abca4$^{-/-}$Rdh8$^{-/-}$ mice administered the agent.

TABLE 1

| Name | Action | Structure | Effect | Dose | Mechanism |
|---|---|---|---|---|---|
| Agomelatine | 5-HT$_{2C}$R antagonist | 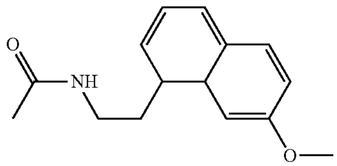 [SMILES: COC1=CC2C(=CC=CC2CCNC(C)=O)C=C1] | 50% | 25 mg/kg | |
| Nefazodone | 5-HT$_{2A}$R (Gq) antagonist | ·HCl | 100% | 30 mg/kg | PLC |
| Eltoprazine | 5-HT$_{2C}$R antagonist | 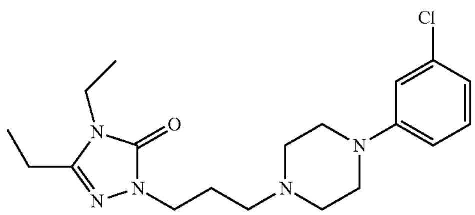 [SMILES: CCc1nn(CCCN2CCN(c3cccc(Cl)c3)CC2)c(=O)n1CC] | 20% | 10 mg/kg | |
| Cyproheptadine | 5-HT$_{2B}$R antagonist | ·HCl | toxic | 20 mg/kg | |
| Pizotifen | 5-HT$_{2A/C}$R (Gq) antagonist | 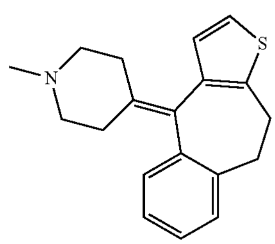 [SMILES: CN1CCC(=C2c3ccccc3CCc3sccc32)CC1] | 75% | 10 mg/kg | PLC |
| RS 23579-190 | 5-HT$_{4R}$ (Gs) antagonist | ·HCl | 100% | 20 mg/kg | Adenylyl cyclase |
| GR 125487 | 5-HT$_{4R}$ antagonist | ·H$_2$NSO$_3$H | 0% | 10 mg/kg | |

TABLE 1-continued

| Name | Action | Structure | Effect | Dose | Mechanism |
|---|---|---|---|---|---|
| RS 39604 | 5-HT$_{4R}$ antagonist | 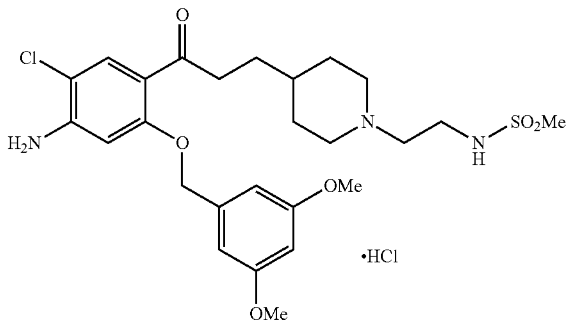 [SMILES: COc1cc(COc2cc(N)c(Cl)cc2C(=O)CCC2CCN(CCNS(C)(=O)=O)CC2)cc(OC)c1 ; Cl] | 0% | 5 mg/kg | |
| SB 203186 | 5-HT$_{4R}$ antagonist | 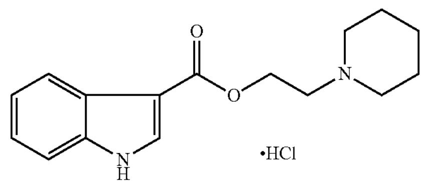 [SMILES: O=C(OCCN1CCCCC1)c1c[nH]c2ccccc12 ; Cl] | 0% | 5 mg/kg | |
| Ro 04-6790 | 5-HT$_{6R}$ (Gs) antagonist | 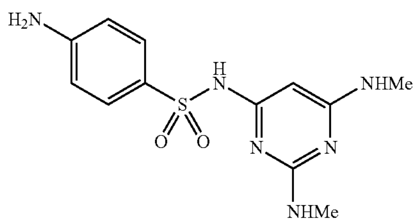 [SMILES: CNc1cc(NS(=O)(=O)c2ccc(N)cc2)nc(NC)n1] | 100% | 30 mg/kg | Adenylyl cyclase |
| SB 399885 | 5-HT$_{6R}$ antagonist | 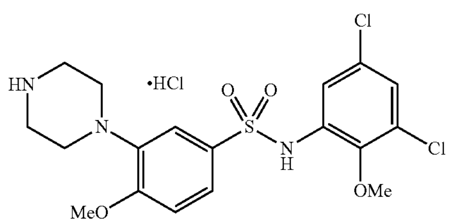 [SMILES: COc1ccc(S(=O)(=O)Nc2cc(Cl)cc(Cl)c2OC)cc1N1CCNCC1 ; Cl] | >25% | 30 mg/kg | |
| SGS 518 oxalate | 5-HT$_{6R}$ (Gs) antagonist | 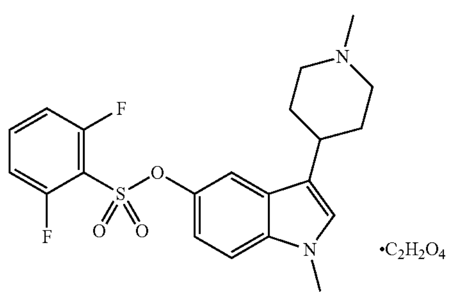 [SMILES: CN1CCC(c2cn(C)c3ccc(OS(=O)(=O)c4c(F)cccc4F)cc23)CC1] | >75% | 30 mg/kg | Adenylyl cyclase |
| SB 269970 | 5-HT$_{7R}$ (Gs) antagonist | 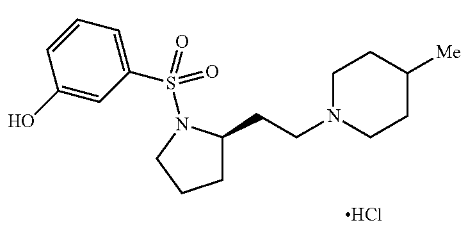 [SMILES: CC1CCN(CC[C@H]2CCCN2S(=O)(=O)c2cccc(O)c2)CC1 ; Cl] | >75% | 30 mg/kg | Adenylyl cyclase |

TABLE 1-continued

| Name | Action | Structure | Effect | Dose | Mechanism |
|---|---|---|---|---|---|
| LY 215840 | 5-HT$_{7/2R}$ (Gs/Gq) antagonist | 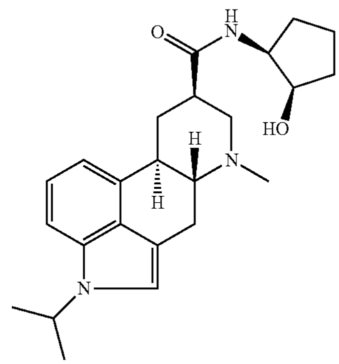 | 100% | 10 mg/kg | Adenylyl cyclase/PLC |
| Doxazosin | alpha-1 adrenergic receptor (Gq) antagonist | 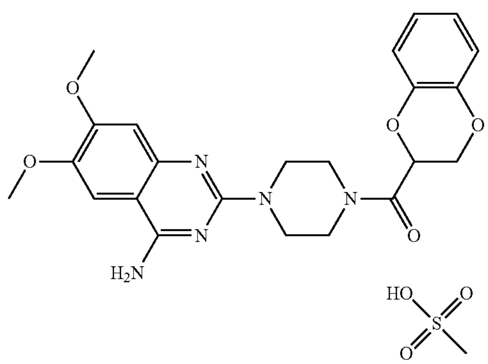 | 100% | 10 mg/kg | PLC |
| Prazosin | alpha-1 adrenergic receptor (Gq) antagonist | 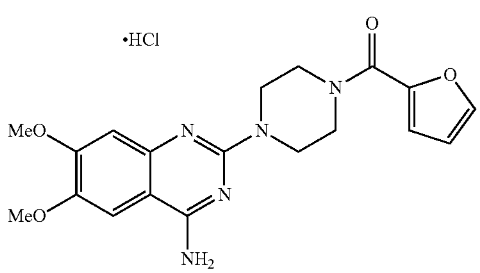 [SMILES: COc1cc2nc(N3CCN(C(=O)c4ccco4)CC3)nc(N)c2cc1OC ; Cl] | 75% | 2 mg/kg | PLC |
| Tamsulosin | alpha-1 adrenergic receptor (Gq) antagonist | 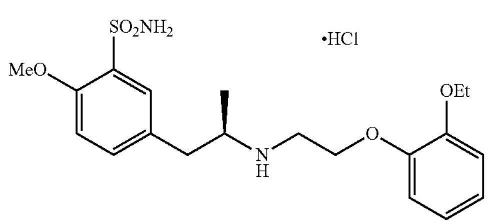 [SMILES: CCOc1ccccc1OCCN[C@H](C)Cc1ccc(OC)c(S(N)(=O)=O)c1 ; Cl] | 75% | 2 mg/kg | PLC |
| Phenoxybenzamine | alpha-1 adrenergic receptor antagonist | 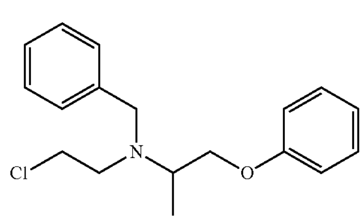 [SMILES: CC(COc1ccccc1)N(CCCl)Cc1ccccc1] | 0% | 25 mg/kg | |

TABLE 1-continued

| Name | Action | Structure | Effect | Dose | Mechanism |
|---|---|---|---|---|---|
| Phentolamine | alpha-1 adrenergic receptor antagonist | 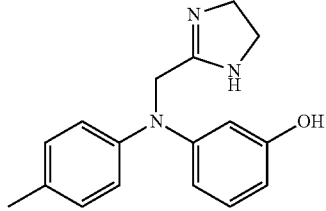 [SMILES: Cc1ccc(N(CC2=NCCN2)c2cccc(O)c2)cc1] | 0% | 5 mg/kg | |
| Guanabenz | alpha-2 adrenergic receptor (Gi) agonist | 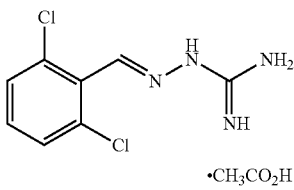 [SMILES: N=C(N)N/N=C/c1c(Cl)cccc1Cl] | 100% | 2 mg/kg | Adenylyl cyclase |
| Guanfacine | alpha-2 adrenergic receptor (Gi) agonist | 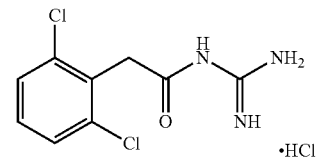 [SMILES: N=C(N)NC(=O)Cc1c(Cl)cccc1Cl ; Cl] | 100% | 2 mg/kg | Adenylyl cyclase |
| Lofexidine | alpha-2 adrenergic receptor (Gi) agonist | 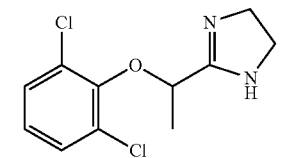 [SMILES: CC(Oc1c(Cl)cccc1Cl)C1=NCCN1] | 100% | 2 mg/kg | Adenylyl cyclase |
| Fexofenadine | H1 histamine receptor (Gq) antagonist | 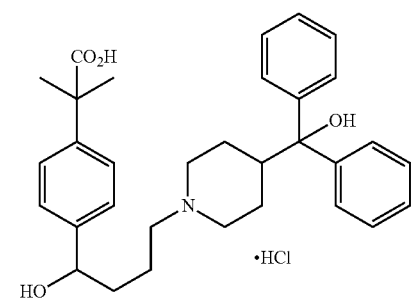 [SMILES: CC(C)(C(=O)O)c1ccc(C(O)CCCN2CCC(C(O)(c3ccccc3)c3ccccc3)CC2)cc1 ; Cl] | 50% | 2 mg/kg | PLC |
| Tolterodine | Muscarinic receptor (Gq) antagonist | 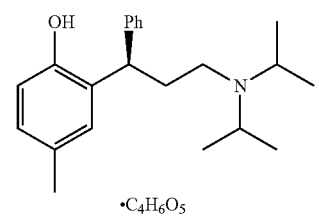 [SMILES: Cc1ccc(O)c([C@H](CCN(C(C)C)C(C)C)c2ccccc2)c1] | 50% | 20 mg/kg | PLC |
| ABT-724 | Dopamine D4 receptor agonist | 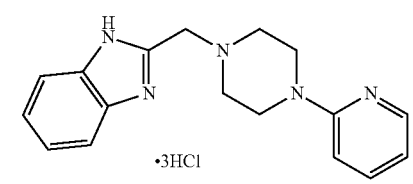 [SMILES: c1ccc(N2CCN(Cc3nc4ccccc4[nH]3)CC2)nc1] | 0% | 2 mg/kg | |

TABLE 1-continued

| Name | Action | Structure | Effect | Dose | Mechanism |
|---|---|---|---|---|---|
| PD-168,077 | Dopamine D4 receptor (Gi) agonist | 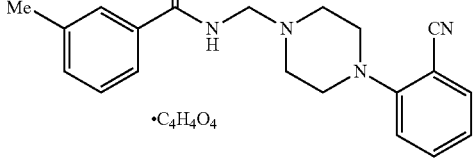 | 60% | 10 mg/kg | Adenylyl cyclase/PLC |
| Yohimbine | Antagonist at multiple receptors | 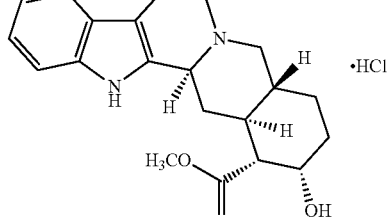 | toxic | 25 mg/kg | |
| Piroxicam | COX-1 inhibitor | 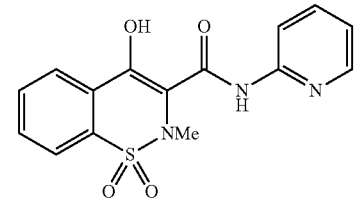 [SMILES: CN1C(C(=O)Nc2ccccn2)=C(O)c2ccccc2S1(=O)=O] | 0% | 2 mg/kg | |
| SQ 22536 | Adenylyl cyclase inhibitor | 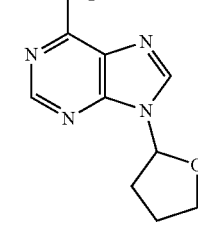 | 100% | 0.5 mg/kg | Adenylyl cyclase |

Example 3

We used a systems pharmacology approach with Abca4$^{-/-}$Rdh8$^{-/-}$ mice that specifically targeted signal transduction by several different GPCRs and their inter-connected mechanisms to identify novel therapeutic strategies for treating blinding retinal disorders such as Stargardt disease and AMD.

Methods

Animals

Abca4$^{-/-}$/Abca8$^{-/-}$ mice were generated and genotyped as previously described and mixed genders were used for the present study when they reached 4- to 5-weeks of age. All mice were routinely maintained in a 12 h light (≤10 lux)/12 h dark cyclic environment in the Animal Resource Center at the School of Medicine, CWRU. For bright light exposure experiments, Abca440). Enucleated macaque (*Macaca fascicularis*) eyes in RNAlater (Invitrogen) from 4-year-old animals were obtained from Ricerca Biosciences (Painesville, Ohio, USA). Clinical evaluation and permission of the human patient from whom retinal tissue was obtained were accomplished at the Cleveland Clinic Cole Eye Institute (Cleveland, Ohio) where this research conformed to the tenets of the Declaration of Helsinki. The retina was carefully dissected out from an untreated eye requiring enucleation for a large ocular melanoma and immediately placed in RNALater.

Transcriptome Analyses of the Eye and Retina

Eyes from C57BL/6J (Jackson laboratory) mice at 4-weeks of age were enucleated and immediately processed to isolate total RNA used to prepare cDNA libraries for sequencing with the Illumina platform of RNA-Sequencing instruments. Three biological replicates were made for both whole eye and retinal tissue to generate transcriptome data used to determine fragments per kilobase of gene product per million reads (FPKM) for normalization and differential expression analyses. Clinical evaluations of the human patient from whom retinal tissue was obtained were carried out at the Cleveland Clinic Cole Eye Institute. This research conformed to the tenets of the Declaration of Helsinki. The retina was carefully dissected out of an untreated eye from the patient requiring enucleation for a large ocular melanoma and immediately placed in RNALater (Invitrogen). The experimental sample was obtained from a tumor-free hemiretina. The eye had no signs of inflammation or abnormal neovascularization of the iris or retina.

Eye and retinal tissue libraries were prepared as previously described. Each mouse and human library was run on the Illumina Genome Analyzer IIx (Illumina) in the CWRU Genomics core facility using 36- to 79-single-end read lengths. The processed and raw fastq files from mouse were previously deposited in GEO (accession numbers GSE38359 and GSE29752).

Chemicals

Doxazosin (DOX) was purchased from Selleckchem. Lofexidine was obtained from Santa Cruz. Prazosin (PRA), tamsulosin (TAM), RS 23579-190 (RS), RO 04-6790 (RO), SB 269970 (SB), SGS 518 oxalate (SGS), LY 215840 (LY), guanabenz (GUB), guanfacine (GUF), idazoxan (IDA), and SQ 22536 (SQ) were purchased from TOCRIS Biosciences and all others from Sigma.

Mouse Treatments

All experimental compounds were administered to mice by intraperitoneal injection through a 28 gauge insulin syringe 30 min prior to bright light exposure. Tested compounds and their doses were: DOX, 1 mg/kg body weights (BW), 2 mg/kg BW, 3 mg/kg BW and 10 mg/kg BW, respectively; PRA, 2 mg/kg BW; TAM, 2 mg/kg BW; RS, 20 mg/kg BW; RO, 30 mg/kg BW; SB, 30 mg/kg BW; SGS, 30 mg/kg BW; LY, 10 mg/kg BW; GUB, 0.5 mg/kg BW, 1 mg/kg BW, 1.5 mg/kg and 2 mg/kg BW, respectively; GUF, 2 mg/kg BW; LOF, 2 mg/kg BW; SQ1, 0.083 mg/kg BW; SQ2, 0.125 mg/kg BW; SQ3, 0.25 mg/kg BW; and SQ4, 0.5 mg/kg BW. IDA, 2.5 mg/kg BW and 5 mg/kg BW. All tested compounds were dissolved in DMSO prior to injection except IDA which was dissolved in 0.9% saline.

Spectral Domain-Optical Coherence Tomography (SD-OCT)

Non-invasive ultra-high resolution SD-OCT (Bioptigen) was performed for in vivo imaging of mouse retinas. Mice were anesthetized with an intraperitoneal injection of an anesthetic cocktail consisting of ketamine (6 mg/ml) and xylazine (0.44 mg/ml) diluted with 10 mM sodium phosphate, pH 7.2, and 100 mM NaCl at a dose of 20 µl/g BW. Pupils were dilated with 1% tropicamide prior to SD-OCT imaging. Five frames of OCT images were acquired in the B-mode and averaged for image presentation and analysis. Retinal pathology was subsequently scored according to the criteria indicated below: Grade 0: outer nuclear layer (ONL) was completely disrupted with no visible appearance observed; grade 1: extensive disruption of an ONL spanning the retina 500 µm away from optic nerve head with the ONL thickness less than 0.01 µm; grade 2: extensive disruption of the ONL spanning the retina 500 µm away from optic nerve head with a measured ONL thickness between 0.01 and 0.03 µm; grade 3: reduction in the thickness of the ONL with a measured thickness between 0.03 and 0.05 µm; grade 4: Intact ONL with a measured thickness over 0.05 µm. For evaluation of the impact of Gi and Gq pathways, data points were plotted as the percentage of eyes that developed significant retinal degeneration with an ONL thickness less than 0.035 mm.

Scanning Laser Ophthalmoscopy (SLO) Imaging

SLO (Heidelberg Engineering) was carried out for in vivo whole fundus imaging of mouse retinas. Mice were anesthetized by intraperitoneal injection of the anesthetic cocktail indicated above, followed by pupil dilation with 1% tropicamide prior to SLO imaging under the autofluorescence mode. Numbers of autofluorescent spots were counted and subjected to statistical analyses as described below.

Immunohistochemistry

Retinal immunohistochemistry (IHC) was performed as previously described. Briefly, eyes were enucleated and, after removal of the cornea, lens and vitreous body, eye cups were fixed in 4% paraformaldehyde and processed for cryosectioning. Twelve µm thick cryosections were cut, collected and examined for rhodopsin expression, peanut agglutinin lectin (PNA) for cone sheath and nuclear DAPI staining.

Electroretinograms (ERGs)

ERGs were performed as previously described. Briefly, dark-adapted mice were examined under dim red light transmitted through a Kodak No. 1 Safelight filter (transmittance 560 nm). Pupils were dilated with 1% tropicamide after anesthesia induced by the method described above. Contact lens electrodes were placed on the eyes, and a reference electrode and ground electrode were positioned on the ear and tail, respectively. ERGs were recorded with the universal testing and electrophysiologic system, UTAS E-3000 (LKC Technologies, Inc.).

In Vivo Detection of ROS

In vivo ROS generation was evaluated as previously described. The ROS probe, DHE, at a dose of 20 mg/kg body weight in 25 µl of DMSO, was administered to $Abca4^{-/-}$ $Rdh8^{-/-}$ mice via intraperitoneal injection 1 h prior to light exposure. Eye cups obtained after removing the cornea, lens, and vitreous body from enucleated eye globes 3 h post light illumination were fixed in 4% paraformaldehyde. Cryosections were prepared from fixed eye cups and cut at 12-µm thickness for microscopic assessment of ROS fluorescence in the retina with ImageJ software (National Institutes of Health).

Two Photon Microscopy (TPM) Imaging

Ten days after bright light exposure, TMP images were obtained as previously described. Briefly, a Leica TCS SP5 upright confocal microscope (Wetzlar, Germany) equipped with 1.0 NA water immersion objective and tunable laser Vision S, Coherent (Coherent, Santa Clara, Calif.) delivering 75 fs laser pulses at 80 MHz pulse repetition frequency was used. Emission spectra were obtained with a TCS SP5 (Leica) spectrally sensitive detector in the descanned configuration. Only intact, freshly enucleated mouse eyes were used for imaging. Before enucleation, mice were anesthetized by intraperitoneal injection of the anesthetic cocktail indicated above and euthanized in compliance with American Veterinary Medical Association (AVMA) Guidelines on Euthanasia, and approval by the Case Western Reserve University Institutional Animal Care and Use Committee.

Quantification of Selected Drugs in Mouse Tissue

C57BL/6J WT mice at 6 weeks of age (Jackson Laboratory) were treated with DOX, GUB, or SQ at a single dose of 10, 2, and 0.5 mg per kilogram, respectively. The compound was dissolved in 50% DMSO in PBS (137 mM NaCl, 2.7 mM KCl, 0.67 mM Na86, 87). Next, to precipitate excess proteins, 0.3 ml of methanol was added to both the eye homogenate and 0.1 ml of serum. Samples were vortexed for 30 s followed by centrifugation for 15 min at 16,000 g. Clear supernatants were collected and used directly for LC-MS analysis. $2HPO_4/KH_2PO_4$, pH 7.4) and administered by intraperitoneal injection. Thirty minutes later the mice were anesthetized. Blood samples were collected using the technique of cardiac puncture and subsequently centrifuged (5 min, 16,000 g) to collect serum. Prior to harvesting eyes, mice were intracardially perfused with PBS to minimalize blood contamination. Eye balls were immediately homogenized in 0.1 ml of PBS. The homogenate and serum samples were spiked with 100 pmols of internal standard (IS) (parazosin-2-[4-(2-furoyl)piperazin-1-yl]-6,7-dimethoxyquinazolin-4-amine (Sigma Aldrich) or clenbuterol—(RS)-1-(4-Amino-3,5-dichlorophenyl)-2-(tert-butylamino)ethanol (Sigma Aldrich)) for DOX, GUB or SQ quantification, respectively ( Mass spectrometry (MS) based detection and quantification of DOX, GUB, and SQ was performed with a LXQ linear ion trap mass spectrometer (Thermo Scientific) equipped with an electrospray ionization (ESI) interface and coupled to Agilent 1100 HPLC (Agilent Technologies). Separation of drugs and the internal standards was achieved on a reverse phase C18 Phenomenex HPLC column (250× 4.60 mm; 5 µm) by a linear gradient of to 100% acetonitrile in water within 15 min at flow rate of 0.5 ml/min. All solvents contained 0.1% formic acid (v/v). The HPLC effluent was sprayed into the MS via an ESI probe operated in the positive ionization mode. Parameters of ionization and detection were tuned with synthetic standards for the drugs to achieve the highest possible sensitivity. Dox and parazosin (internal standard) were detected by selected reaction monitoring (SRM) using m/z 452.2→344.2 and 384.2→247.1 transitions whereas GUB, SQ and their corresponding IS, clenbuterol, was by fragmentation at m/z 231.1→214.0, 206.1→136.0, and 277.1→259.1, respectively. The elution times for DOX, GUB, and SQ were ~12.8, 12.3, and 10.8 min, respectively. Both internal standards eluted at 12.0 min (FIG. 34). Calibration curves were calculated based on the linear relationship between ratios of SRM ion intensity peak area corresponding to the selected drug and the IS vs. molar ratios of the compounds in the range of 20-500 pmol (FIG. 34H).

Statistical Analyses

Results were collected from at least 4 mice per experimental group. Data are expressed as means±SEM and statistical analyses were performed using a 1-way Students t-test or ANOVA. A p value of ≤0.05 was considered statistically significant.

Results

Expression of GPCRs and GPCR Signaling Genes in Human and Mouse Retina

Expression analysis of retinal GPCRs by immunocytochemistry was unreliable for reasons that include poor specificity and low affinity of antibodies (data not shown) as well as low GPCR expression. Therefore, we turned to quantitative transcriptome analysis of human and mouse retinas without specific cellular localization.

Overall, we found 1766 unique gene products categorized as having GPCR activity by gene ontology in *Mus musculus*. The same mouse transcripts were also recognized in the retinal transcriptome from *Homo sapiens*. Of these 1766, 165 genes displayed expression of at least 1 FPKM (fragment per kilobase exon per million reads mapped), equivalent to 1 transcript per cell, in C57BL/6J mouse eye or retina with 6 genes below the 1 FPKM threshold in mouse eye but above the 1 FPKM threshold in mouse retina (Table 2). Expression of these 165 genes from human retina is also displayed as decreasing FPKM values starting from rhodopsin (Rho), the highest expressed gene in mouse eye. The highest expressed human GPCR was rhodopsin, followed by retinal G protein receptor (RGR) and the cone pigments, Opn1sw and Opn1mw.

A more detailed analysis was carried out of adenylate cyclases (ACs), α1-adrenergic receptors (α1-ARs), α2-ARs and serotonin receptors (5-HTRs) to detect potential pathways that could be affected by a systems pharmacological approach. Reaction quenching molecules, such as arrestins and GPCR kinases were also investigated (Table 3). Expression values for these genes in mouse and human retinas highlighted those pathways that should be most susceptible to pharmacological treatment as well as those targets that would best translate from mouse models to human patients. For example, among isoforms of the α1-ARs and α2-ARs, the human retina expressed α2C-AR at the highest level (Table 3) and among 5-HTRs, 5-HT2AR had the highest expression. Data from real-time PCR analyses corroborated that expression of these genes are readily detected in the mouse retina and/or RPE (unpublished observations).

TABLE 2

| Genes | B6 mouse eye | B6 mouse retina | Human retina |
| --- | --- | --- | --- |
| Rho | 6162.01 | 11630.18 | 6896.09 |
| Rgr | 355.74 | 97.66 | 123.98 |
| Opn1sw | 125.13 | 198.54 | 31.69 |
| DRD4 | 93.84 | 241.78 | 139.49 |
| Opn1mw | 62.97 | 95.77 | 172.56 |
| Gprc5b | 29.82 | 12.95 | 22.85 |
| Gpr162 | 29.37 | 73.32 | 46.29 |
| Gpr37 | 28.47 | 41.28 | 66.65 |
| Ednrb | 22.27 | 1.94 | 5.77 |
| Rorb | 21.69 | 23.52 | 24.31 |
| Gpr153 | 20.42 | 37.18 | 15.31 |
| Gabbr1 | 19.78 | 40.24 | 35.38 |
| Rrh | 19.29 | 9.23 | 40.34 |
| Gpr152 | 18.55 | 40.46 | 3.05 |
| Adora1 | 16.20 | 18.26 | 13.55 |
| Lphn1 | 15.98 | 29.73 | 31.85 |
| Tm2d1 | 15.56 | 10.31 | 17.63 |
| Cxcr7 | 14.30 | 3.58 | 2.37 |
| Ppard | 13.68 | 19.37 | 21.61 |
| Agtrap | 13.64 | 17.21 | 8.18 |
| Cd97 | 12.93 | 1.77 | 1.55 |
| Gpr19 | 12.21 | 8.45 | 1.11 |
| Fzd1 | 11.99 | 3.29 | 7.35 |
| Fzd6 | 11.34 | 1.85 | 2.76 |
| Gpr87 | 11.34 | 0.04 | 0.00 |
| Lgr4 | 11.09 | 9.50 | 18.07 |
| Drd2 | 10.82 | 23.10 | 26.33 |
| Smo | 10.75 | 6.35 | 5.91 |
| S1pr1 | 10.66 | 11.21 | 11.78 |
| Bai1 | 10.08 | 27.10 | 10.82 |
| Glp2r | 9.94 | 34.85 | 0.31 |
| Ptger1 | 9.59 | 14.88 | 0.94 |
| Gpr124 | 9.56 | 8.94 | 19.82 |
| F2r | 9.31 | 5.32 | 0.15 |
| Adra2c | 8.96 | 7.17 | 2.38 |
| Gpr146 | 8.91 | 7.49 | 6.17 |
| Vipr2 | 8.79 | 14.33 | 10.69 |
| Fzd5 | 8.69 | 10.01 | 7.73 |
| Gpr110 | 8.59 | 0.08 | 0.02 |
| Adrb1 | 8.43 | 20.18 | 3.84 |
| S1pr3 | 8.42 | 6.95 | 3.56 |
| Gabbr2 | 7.80 | 17.03 | 10.57 |
| Lphn2 | 7.66 | 9.02 | 8.79 |
| Lpar1 | 7.47 | 0.91 | 0.45 |
| P2ry2 | 7.20 | 0.62 | 2.29 |
| Adrb2 | 7.13 | 1.03 | 0.98 |
| Hrh3 | 7.11 | 19.12 | 3.75 |
| Bai2 | 6.81 | 15.34 | 14.64 |
| Gpr143 | 6.80 | 1.25 | 0.80 |
| Celsr2 | 6.53 | 7.26 | 10.80 |
| Fzd7 | 6.34 | 1.88 | 2.51 |
| Drd1a | 6.15 | 9.49 | 8.45 |
| Adora2b | 6.09 | 2.53 | 3.83 |
| Celsr3 | 5.82 | 20.00 | 9.87 |
| Fzd4 | 5.39 | 4.28 | 0.43 |
| Gprc5c | 5.26 | 2.13 | 3.13 |
| Gpr56 | 5.12 | 4.31 | 2.92 |
| Npr3 | 5.10 | 0.72 | 0.44 |
| Tacr3 | 4.95 | 4.63 | 2.36 |
| Grm8 | 4.77 | 6.43 | 2.04 |
| Ramp1 | 4.68 | 1.39 | 5.25 |
| Adra2a | 4.60 | 9.91 | 0.25 |
| Grp85 | 4.56 | 5.72 | 2.70 |
| Lphn3 | 4.22 | 6.49 | 2.90 |
| Htr3a | 4.14 | 2.54 | 0.00 |
| Bai3 | 3.92 | 6.01 | 1.91 |
| Fzd2 | 3.89 | 0.79 | 3.24 |
| Fzd1 | 3.86 | 6.31 | 0.36 |
| Gpr98 | 3.79 | 7.30 | 3.64 |
| Tacr1 | 3.72 | 2.06 | 0.95 |
| Gpr158 | 3.72 | 5.07 | 3.58 |

TABLE 2-continued

| Genes | B6 mouse eye | B6 mouse retina | Human retina |
|---|---|---|---|
| Fzd8 | 3.56 | 3.26 | 15.06 |
| Opn4 | 3.35 | 2.94 | 1.11 |
| Tshr | 3.24 | 1.55 | 0.00 |
| S1pr2 | 3.20 | 1.13 | 0.63 |
| Mrgprf | 3.18 | 0.64 | 0.80 |
| Oprl1 | 3.15 | 4.42 | 0.81 |
| F2rl1 | 3.13 | 0.24 | 2.58 |
| S1pr5 | 3.12 | 0.48 | 0.01 |
| Gpr135 | 3.07 | 8.35 | 1.99 |
| Crhr1 | 3.02 | 6.49 | 12.76 |
| Eltd1 | 3.00 | 1.65 | 0.51 |
| Mrgpre | 2.96 | 2.80 | 1.74 |
| Gpr27 | 2.92 | 3.88 | 8.45 |
| Ednra | 2.87 | 0.52 | 0.16 |
| Grm4 | 2.86 | 4.93 | 3.10 |
| Emr1 | 2.60 | 0.22 | 0.03 |
| Opn3 | 2.55 | 1.38 | 2.62 |
| Cnr1 | 2.41 | 2.97 | 0.48 |
| Grm7 | 2.39 | 3.95 | 1.16 |
| Gpr37l1 | 2.39 | 0.96 | 7.73 |
| Grm1 | 2.27 | 3.52 | 4.97 |
| Crhr2 | 2.24 | 1.12 | 4.34 |
| P2ry14 | 2.23 | 0.59 | 0.00 |
| Gpr176 | 2.21 | 3.43 | 4.23 |
| Celsr1 | 2.18 | 0.24 | 0.57 |
| Gpr22 | 2.17 | 1.74 | 0.61 |
| Lgr5 | 2.10 | 4.08 | 0.33 |
| Gpr26 | 2.06 | 3.96 | 0.32 |
| Agrt2 | 2.02 | 0.07 | 0.01 |
| Gpr68 | 2.02 | 1.33 | 0.47 |
| Calcrl | 2.02 | 0.31 | 0.10 |
| Cckbr | 2.00 | 3.94 | 0.21 |
| Gpr75 | 1.92 | 2.74 | 10.70 |
| P2ry1 | 1.91 | 2.74 | 10.70 |
| Chrm2 | 1.89 | 1.98 | 0.55 |
| Fzd3 | 1.86 | 2.98 | 6.25 |
| Grm5 | 1.83 | 2.19 | 1.57 |
| Adcyap1r1 | 1.81 | 1.50 | 2.86 |
| Htr1b | 1.80 | 3.99 | 0.80 |
| Cx3cr1 | 1.79 | 0.90 | 2.05 |
| Gpr4 | 1.74 | 1.15 | 0.30 |
| P2ry6 | 1.73 | 0.25 | 0.79 |
| Adra1d | 1.72 | 3.83 | 0.08 |
| Tbxa2r | 1.72 | 0.44 | 0.20 |
| Gpr61 | 1.66 | 3.41 | 3.81 |
| Sstr2 | 1.66 | 3.01 | 3.56 |
| Chrm3 | 1.64 | 2.46 | 0.96 |
| Sstr4 | 1.64 | 2.46 | 0.96 |
| Adra1b | 1.60 | 1.62 | 1.12 |
| Cmklr1 | 1.60 | 0.27 | 0.24 |
| Chrm1 | 1.53 | 1.54 | 0.34 |
| Htr1d | 1.49 | 2.58 | 0.00 |
| Cxcr4 | 1.42 | 0.71 | 2.65 |
| Kiss1r | 1.37 | 2.59 | 0.87 |
| C5ar1 | 1.35 | 0.12 | 3.01 |
| Mc1r | 1.32 | 2.05 | 5.65 |
| Ptgfr | 1.32 | 0.06 | 0.12 |
| Fzd9 | 1.30 | 1.86 | 1.39 |
| Ptgir | 1.20 | 0.38 | 0.17 |
| Hcrtr1 | 1.19 | 2.00 | 0.18 |
| Ccrl2 | 1.16 | 0.27 | 0.07 |
| P2ry12 | 1.16 | 0.54 | 0.34 |
| Gpr12 | 1.15 | 1.94 | 6.01 |
| Gpr173 | 1.13 | 1.77 | 5.26 |
| Gpr88 | 1.11 | 1.78 | 0.91 |
| Chrm4 | 1.10 | 0.78 | 7.70 |
| Galr2 | 1.08 | 0.59 | 0.00 |
| Cysltr1 | 1.07 | 0.02 | 0.12 |
| Lepr | 1.06 | 0.036 | 0.56 |
| Gpr161 | 1.05 | 0.99 | 1.54 |
| Oxtr | 1.02 | 0.72 | 1.60 |
| Gpr64 | 1.01 | 0.17 | 0.26 |
| Gpr157 | 0.95 | 1.05 | 0.61 |
| Drd5 | 0.90 | 1.66 | 2.26 |
| Gpr182 | 0.87 | 1.28 | 0.11 |
| Rxfp3 | 0.76 | 1.09 | 0.00 |
| Nmbr | 0.72 | 1.16 | 0.61 |
| Grik3 | 0.70 | 1.24 | 4.18 |
| Ccr10 | 0.68 | 1.47 | 5.60 |
| Gpr156 | 0.67 | 1.16 | 0.43 |
| Tas1r3 | 0.64 | 1.15 | 0.95 |
| Gpr3 | 0.60 | 1.33 | 1.91 |
| Tas1r1 | 0.59 | 1.76 | 0.27 |
| Gpr84 | 0.43 | 1.59 | 1.89 |

[A]Analyses were done as described in Materials and Methods. Transcriptome data were used to determine reads per kilobase of gene product per million reads (RPKM) for normalization and differential expression analyses. Higher expression values in the retina relative to the eye indicate their enrichment in retina. Such high values highlight those GPCRs that may be critical in the eye and retina for drug discovery and therapeutic approaches. Both processed and raw fastq files for transcriptome analyses were deposited in GEO (accession numbers GSE29752 and GSE38359).

To better understand GPCR localization in the eye and even the macula, we undertook more in-depth transcriptome studies. We first carried out transcriptome studies of rhodopsin knockout mice, which exhibit no rod pigment expression and fail to form rod photoreceptors, to potentially localize such transcripts to this photoreceptor layer. We also did transcriptome studies with macular tissue isolated from monkeys to learn if these GPCRs localize there and potentially mediate the high resolution vision disrupted in macular diseases such as Stargardt disease. Our results (Table 3) showed that robust expression of Adcy1 was present in all eye tissues but it was attenuated in the rhodopsin knockout mouse, indicative of its photoreceptor localization. Adcy1 expression was also noticed to be enriched in the monkey macula.

TABLE 3

Expression of adrenergic receptors, serotonin receptors, and adenylate cyclases in the eye and retina of C57BL/6J mice, the eye of photoreceptor degenerated Rho$^{-/-}$ mice, the retina of a human donor eye, and macular tissue from monkey (Macaca fasicularis)[A]

| Gene | B6 Mouse Eye | B6 mouse retina | Rho$^{-/-}$ mouse eye | Human Retina | Monkey macula |
|---|---|---|---|---|---|
| Adenylate Cylases | | | | | |
| Adcy1 | 17.53 | 37.50 | 9.272 | 68.60 | 81.26 |
| Adcy2 | 14.41 | 21.70 | 22.96 | 5.78 | 11.42 |
| Adcy3 | 5.59 | 5.09 | 1.57 | 5.70 | 21.21 |
| Adcy4 | 1.34 | 0.54 | 2.52 | 1.18 | 0.48 |
| Adcy5 | 7.19 | 11.15 | 11.14 | 8.00 | 12.79 |
| Adcy6 | 17.68 | 49.98 | 11.41 | 9.99 | 7.25 |
| Adcy7 | 4.95 | 0.75 | 0.60 | 1.14 | 2.46 |
| Adcy8 | 2.13 | 3.80 | 2.76 | 3.73 | 8.94 |
| Adcy9 | 3.05 | 3.99 | 3.53 | 4.64 | ND |
| Adcy10 | 0.02 | 0.03 | 0.01 | 0.01 | 0.33 |
| Adrenergic | | | | | |
| Adra1a | 0.45 | 0.26 | 0.63 | 0.20 | 1.35 |
| Adra1b | 1.60 | 1.62 | 2.35 | 1.12 | 6.61 |
| Adra1d | 1.72 | 3.83 | 4.26 | 0.08 | 3.97 |
| Adra2a | 4.60 | 9.91 | 6.14 | 0.25 | 0.67 |
| Adra2b | 0.20 | 0.29 | 0.20 | 0.02 | 4.30 |
| Adra2c | 8.96 | 7.17 | 19.28 | 2.38 | 4.30 |
| Serotonin Receptors | | | | | |
| Htr1a | 0.17 | 0.28 | 0.13 | 0.15 | 0.16 |
| Htr1b | 1.80 | 3.99 | 1.05 | 0.80 | 8.22 |
| Htr1d | 1.49 | 2.58 | 1.91 | 0.00 | 0.07 |
| Htr1f | 0.03 | 0.04 | 0.03 | 0.44 | 0.06 |
| Htr2a | 0.67 | 0.72 | 0.68 | 1.30 | 0.67 |
| Htr2b | 0.50 | 0.43 | 0.30 | 0.39 | 0.86 |
| Htr2c | 0.56 | 0.73 | 0.52 | 0.02 | 0.27 |
| Htr4 | 0.02 | 0.01 | 0.01 | 0.43 | 0.05 |
| Htr5a | 0.43 | 0.59 | 0.48 | 0.00 | 2.17 |
| Htr6 | 0.19 | 0.19 | 0.36 | 0.29 | 0.00 |
| 0.29Htr7 | 0.31 | 0.31 | 0.1 | 0.01 | 0.59 |

TABLE 3-continued

Expression of adrenergic receptors, serotonin receptors, and adenylate cyclases in the eye and retina of C57BL/6J mice, the eye of photoreceptor degenerated Rho$^{-/-}$ mice, the retina of a human donor eye, and macular tissue from monkey (Macaca fasicularis)[A]

| Gene | B6 Mouse Eye | B6 mouse retina | Rho$^{-/-}$ mouse eye | Human Retina | Monkey macula |
|---|---|---|---|---|---|
| Arrestins | | | | | |
| SAG | 1220.54 | 1805.26 | 301.99 | 3562.22 | 2248.35 |
| Arrb1 | 18.38 | 18.10 | 9.42 | 8.21 | 18.22 |
| Arrb2 | 8.86 | 14.99 | 11.92 | 17.92 | 21.68 |
| Arr3 | 50.73 | 128.48 | 32.62 | 270.16 | 680.86 |
| GPCR Kinases | | | | | |
| Grk1 | 111.20 | 236.84 | 14.19 | 175.06 | 88.96 |
| Adrbk1 | 28.70 | 36.88 | 36.15 | 27.29 | 32.71 |
| Adrbk2 | 2.83 | 4.68 | 3.52 | 1.30 | 8.84 |
| Grk4 | 0.86 | 0.90 | 0.42 | 5.31 | ND |
| Grk5 | 3.08 | 2.97 | 2.57 | 2.99 | 5.06 |
| Grk6 | 20.26 | 20.31 | 6.95 | 9.69 | 9.02 |
| Grk7 | ND | ND | ND | 8.94 | 20.48 |
| Photoreceptor genes | | | | | |
| Abca4 | 59.00 | 140.14 | 15.85 | 267.71 | 129.68 |
| Opn1sw | 117.79 | 187.21 | 72.95 | 25.42 | 151.31 |
| Rho | 5853.00 | 11081.16 | 39.26 | 6386.12 | 8168.27 |

[A]Analyses were done as described in Materials and Methods. Greater expression in one compartment compared to another or from one species to another indicates their enrichment in that particular compartment. Values for photoreceptor genes. Abca4, Opn1sw, and rhodopsin (Rho) are shown for reference.
ND indicates not determined because no gene homolog exists in the designated species.

Contribution of Gi and Gq Pathways to Light-Induced Retinal Pathogenesis in the Abca4$^{-/-}$Rdh8$^{-/-}$ Mouse Model To further elucidate the impact of Gi and Gq GPCR pathways on the pathogenesis of bright light induced degeneration in Abca4$^{-/-}$Rdh8$^{-/-}$ mice, we tested both the additive effects of Gi pathway activation and Gq pathway inhibition and the opposing effects of treatment with both idazoxan (IDA), an α2-AR antagonist, and GUB, an α2-AR agonist. Both GUB (an activator of the Gi pathway) (FIG. 25A) and DOX (an antagonist of the Gq pathway) (FIG. 25B) protected the retinas of Abca4$^{-/-}$Rdh8$^{-/-}$ mice from developing bright light-induced degeneration in a dose-dependent fashion. To further evaluate these positive effects, we first determined the half maximal protective dose of GUB to be 0.3 mg/kg (FIG. 30A) and that of DOX to be 0.4 mg/kg (FIG. 25B). Then we found that treating mice simultaneously with half maximal effective doses of GUB and DOX completely protected retina from bright light-induced degeneration (FIG. 25C) indicating that simultaneous activation of Gi and inhibition of Gq pathways accomplish retinal protection in an additive manner. Additionally, we verified that treating the mice first with α2-AR antagonist, IDA, followed by treating mice with GUB, totally abolished the protective action of a fully effective dosage of the α2-AR agonist, GUB. In distinct contrast to mice treated with GUB alone, retinas of mice pre-treated with IDA and then with GUB were dramatically damaged. Moreover, this damage was more evident with an increased dose of IDA (FIG. 25D). This last result further confirms the positive impact of activating the Gi pathway on retinal protection from bright light-induced degeneration.

Pharmacological Interventions Targeting Gq-, Gi-, Gs-Coupled GPCRs and AC Preserve Retinal Function The effects of pre-treatment with selected compounds affecting Gq-, Gi-, Gs-coupled GPCRs and AC were also examined by scotopic and photopic ERG analyses performed 2 weeks after bright light exposure (FIG. 26). Bright light exposure at 10,000 lux for 30 min nearly abolished the scotopic ERG response in Abca4$^{-/-}$Rdh8$^{-/-}$ mice pre-treated with DMSO vehicle (FIGS. 26, A and B). In marked contrast, substantial preservation of this response was achieved by pre-treatments individually targeting multiple GPCRs. These included DOX, an antagonist of Gq-coupled α1-AR; RS, an antagonist of the Gs-coupled 5-HT4 receptor; RO, an antagonist of the Gs-coupled 5-HT6 receptor; LY, an antagonist of the 5-HT7 receptor; LOF, an agonist of the Gi-coupled α2-AR and SQ, an inhibitor of AC. These data indicate that pharmacological treatment targeting these GPCRs also protects against light-induced retinal degeneration. A complete list of therapeutics is listed in Table 1.

Pharmacological Interventions Targeting GPCRs and AC Prevent Light-Induced Degeneration in WT Mice To investigate whether compounds which showed the protective effect against retinal degeneration in Abca4$^{-/-}$Rdh8$^{-/-}$ mice could also prevent retinal degeneration in WT mice, DOX (α1-AR agonist), GUB (α2-AR agonist), and AC inhibitor SQ were further tested for their effect on light-induced retinal degeneration in BALB/c mice. These drugs were administered to 4-week-old BALB/c mice by intraperitoneal injection 30 min prior to white light exposure at 10,000 lux for 1 h. Retinal morphology was assessed 7 days after light exposure by OCT imaging and histological examination. As shown in FIG. 27, severe retinal degeneration was observed in mice treated with DMSO vehicle, whereas retinal morphology of drug-treated mice was maintained and no obvious signs of retinal degeneration being observed. Moreover, SLO examination revealed infiltration of microglia/macrophages into the subretinal space as increased number of autofluorescent spots in DMSO treated and light-exposed mice, which was prevented in mice treated with DOX, GUB or SQ. These results indicate that pharmacological interventions targeting GPCRs and AC also could prevent light-induced degeneration in WT mice.

Pharmacological Interventions Targeting GPCRs and AC Inhibit ROS Generation in Mice after Light Exposure Production of ROS is closely associated with photoreceptor cell death in Abca4$^{-/-}$Rdh8$^{-/-}$ mice. Thus, compounds which showed the protective effect against retinal degeneration in Abca4$^{-/-}$Rdh8$^{-/-}$ mice were also examined for their ability to modulate ROS generation in Abca4$^{-/-}$Rdh8$^{-/-}$ mice after light exposure. Dark-adapted Abca4$^{-/-}$Rdh8$^{-/-}$ mice at the age of 4-5 weeks were intraperitoneally injected with the fluorescent ROS probe, DHE, together with DOX (α1-AR agonist), GUB (α2-AR agonist) or SQ (AC inhibitor) 30 min prior to light exposure at 10,000 lux for 1 h. As shown in FIG. 28, strongest ROS signals were detected in photoreceptor nuclei in DMSO-treated mice among all the mice examined. Pharmacological interventions targeting GPCRs and AC were able to reduce ROS generation in Abca4$^{-/-}$Rdh8$^{-/-}$ mice after light exposure. These results indicate that ROS generation is one of the common downstream pathways potentially mediating the effects of aberrant GPCR/AC signaling in light-induced retinal degeneration in Abca4$^{-/-}$Rdh8$^{-/-}$ mice.

Penetration of DOX, GUB, and SQ into Mouse Eyes

Though drugs administrated into systemic circulation are distributed throughout the body, they also can achieve different concentrations in various organs and tissues depending on rates of vascular perfusion and the drugs' molecular properties, such as their lipid solubility, pKa, and ability to bind to carrier proteins. Moreover, drugs can also be cleared from target organs/tissues at different rates. To investigate whether DOX, GUB, and SQ can penetrate and persist in the eye, we quantified the amounts of these drugs present in the C57BL/6J (WT) whole mouse eye globes within 2 h after drug injection and compared these levels to those in serum. Liquid chromatography-mass spectrometry (LC-MS)-based analyses and quantification revealed the presence of tested compounds at levels in the low picomolar range in eye tissue (Table 4 and FIG. 29). Given that the total volume of a mouse eye is about 0.1 mL, the amounts of examined compounds were comparable with levels found in 0.1 mL of serum samples for GUB and 5 times lower for both DOX and SQ. However, the retinal cell layer with an area of 15.6 mm$^2$ constitutes only a small fraction of the eye that likely absorbs most of these drugs entering from the blood. Thus, considering that prior to harvesting eyes, mice were intracardially perfused with PBS, the amounts of DOX, GUB and SQ confirmed their availability to eye tissue.

TABLE 4

Amount of selected drugs found in the mouse serum and enucleated eyes 30 min after administration of a single dose

| Name | Serum (pmol/100 µl) ± SD | Eye (pmol/eye) ± SD |
|---|---|---|
| DOX | 46.5 ± 12.8 | 11.0 ± 1.7 |
| GUB | 7.0 ± 1.8 | 13.1 ± 4.7 |
| SQ | 19.3 ± 5.5 | 5.6 ± 2.2 |

$^A$Doxazosin (DOX), guanabenz (GUB), and SQ 22536 (SQ) were detected and quantified in tissues of C57BL/J WT mice by LC-MS. All three drugs were found to penetrate and persist in the eye, with GUB reaching higher concentration in the eye than in the serum.

Pharmacological Intervention Targeting Gq- and Gi-Coupled GPCRs Prevents Formation of Large Fluorescent Deposits in the RPE.

The above results demonstrate a protective effect on photoreceptor morphology and function by pre-treatment with pharmacological compounds targeting Gq-, Gi-, Gs-coupled GPCRs. To investigate their impact on the RPE, we treated 4 to 5-week-old albino Abca4$^{-/-}$Rdh8$^{-/-}$ mice with GUF, GUB, DOX, PRA or TAM, 30 min before bright light exposure. Changes in RPE morphology were assessed on freshly enucleated mouse eyes by TPM performed 10 days after treatment. Mice exposed to bright light but not pretreated with the above compounds accumulated large long-wavelength evoked fluorescent deposits in the RPE which otherwise appeared structurally unaffected. Representative TPM images comparing the RPE from mice treated with PRA, GUB and vehicle are shown in FIG. 30A. Spectra of these granules, shown in FIG. 30B, displayed broad maxima at 590 to 625 nm indicative of pyridinium bisretinoid, A2E and related retinoids. These data indicate that treatment with compounds targeting Gq- and Gi-coupled GPCRs can prevent the RPE from accumulating potentially toxic long-wavelength fluorescent deposits.

Our results indicate that GPCR pathways provide distinct activation and inhibitory actions that can control photoreceptor cell survival. Thus, activation of the Gq pathway, accomplished by the α1AR among others, can lead to photoreceptor cell death through the phospholipase C-mediated signaling pathway. Photoreceptor death can also result from aberrant functioning of Gs and Gi pathways that modulate the formation of cAMP. Gs, affected by the action of the 5-HT4, 6 and 7 receptors, activates this pathway whereas Gi, mediated by the α2AR, inhibits it. Therefore, the degenerative photoreceptor phenotypes in pathological states could be abrogated by pharmacological inhibition of either Gq or Gs pathways or activation of the Gi pathway.

It is also worth noting that rhodopsin could be a central player in light-induced retinal degeneration, and that reduced amounts of rhodopsin protect the retina from light-induced degeneration. Therefore we examined the potential impact of the AC inhibitor SQ on chromophore regeneration given that AC is the central player in our newly identified GPCR signaling implicated in light-induced retinopathy (FIG. 1). When the effect of SQ treatment on ERG responses and 11-cis-retinal levels after bleaching was evaluated, no significant changes were observed, indicating that the protection against retinal degeneration conferred by SQ treatment was unlikely due to inhibition of visual pigment regeneration. Therefore, the possibility of an acute effect of pharmacological compounds on phototransduction could be ruled out.

Together, experimental results described here and in the previous examples identify a series of intrinsically linked events, including the participation of GPCRs, PLC/IP3/Ca2+ signaling, and NADPH oxidase-mediated ROS production, which collectively are responsible for the pathogenesis of retinal dystrophy in Abca4$^{-/-}$Rdh8$^{-/-}$ mice, a model for rod/cone degeneration resembling features of human Stargardt disease. Our findings show that atRAL toxicity in bright light-induced retinal degeneration could be mediated through a signaling cascade implicating GPCRs, PLC/IP3/Ca2+ signaling, and NADPH oxidase. Here we report that, in addition to Gq signaling, inhibition of the cAMP pathway also has a protective effect against retinal degeneration. Our results demonstrate that GPCR pathways provide distinct activation and inhibitory actions that could control photoreceptor cell survival. Thus, activation of the Gq pathway, accomplished by the α1-AR among others, can lead to photoreceptor cell death through the phospholipase C-mediated signaling pathway. Photoreceptor death can also result from aberrant functioning of Gs and Gi pathways that modulate the formation of cAMP. Gs, affected by the action of the 5-HT4, 6 and 7 receptors, activates this pathway whereas Gi, mediated by the α2-AR, inhibits it.

As presented here, the degenerative photoreceptor phenotypes was reversed by pharmacological inhibition of either Gq or Gs pathways or activation of the Gi pathway (FIG. 1). These proof-of-concept studies demonstrate interactions between interconnected and diverse pathways involved in the pathogenesis of retinal degeneration induced by strong light.

From the above description of the invention, those skilled in the art will perceive improvements, changes and modifications Such improvements, changes and modifications are within the skill of the art and are intended to be covered by the appended claims. All publications, patents, and patent applications cited in the present application are herein incorporated by reference in their entirety.

Having described the invention, the following is claimed:

1. A method of treating light induced retinal degeneration in the retina of a subject in need thereof, comprising:
administering to the subject one or more agents that inhibit and/or block the activation of Gs- or Gq-protein coupled receptors or Gs- or Gq-signaling cascade in ocular cells of the subject, and/or activate Gi-protein coupled receptors, wherein the one or more agents include doxazosin and guanabenz that are administered at an amount subtherapeutic to amounts required to treat the light induced retinal degeneration when each of the doxazosin and the guanabenz is administered alone, wherein the activation of the Gs- or Gq-protein coupled receptors or Gs- or Gq-signaling cascade is induced or triggered by light induced all-trans-retinal generation.

2. The method of claim 1, further comprising administering to the subject a therapeutically effective amount of at least three or more of a Gs or Gq coupled serotonin receptor antagonist, additional alpha 1 adrenergic antagonist, additional alpha-2 adrenergic receptor agonist, an adenylyl cyclase inhibitor, an M3 receptor antagonist, or a phospholipase C (PLC) inhibitor.

3. The method of claim 1, further comprising administering to the subject a therapeutically effective amount of at least four or more of a Gs or Gq coupled serotonin receptor antagonist, additional alpha 1 adrenergic antagonist, additional alpha-2 adrenergic receptor agonist, an adenylyl cyclase inhibitor, an M3 receptor antagonist, or a PLC inhibitor.

4. The method of claim 1, further comprising administering to the subject a therapeutically effective amount of at least two or more of a serotonin receptor antagonist, additional alpha 1 adrenergic antagonist, adenylyl cyclase inhibitor, PLC inhibitor, or M3 receptor antagonist.

5. The method of claim 1, further comprising administering to the subject a therapeutically effective amount of at least two or more of a serotonin receptor antagonist, additional alpha-2 adrenergic receptor agonist, adenylyl cyclase inhibitor, PLC inhibitor, or M3 receptor antagonist.

6. The method of claim 1, further comprising administering to the subject a therapeutically effective amount of at least two or more of a adenylyl cyclase inhibitor, PLC inhibitor, or M3 receptor antagonist.

7. The method of claim 1, wherein the one or more agents further comprise one or more Gs or Gq coupled serotonin receptor antagonists selected from the group consisting of a $5\text{-HT}_{2a}$ receptor antagonist, a $5\text{-HT}_{2b}$ receptor antogonist, a $5\text{-HT}_{2c}$ receptor antagonist, a $5\text{-HT}_{2a/c}$ receptor antagonist, a $5\text{-HT}_{4}$ receptor antagonist, a $5\text{-HT}_{6}$ receptor antagonist, and a $5\text{-HT}_{7}$ receptor antagonist.

8. The method of claim 7, wherein the serotonin receptor antagonist is selected from the group consisting of agomelatine, pizotifen, RS 23579-190, Ro 04-6790 (4-Amino-N-[2,6-bis(methylamino)-4-pyrimidinyl]benzenesulfonamidev), SGS 518 oxalate (1-methyl-3-(1-methyl-4-piperidyl)indol-5-yl] 2,6-difluorobenzenesulfonate; oxalic acid), SB 269970 (3-({(2R)-2-[2-(4-Methyl-1-piperidinyl)ethyl]-1-pyrrolidinyl}sulfonyl)phenol hydrochloride (1:1)), LY 215840 ((8β)-N-[(1S,2R)-2-Hydroxycyclopentyl]-1-isopropyl-6-methylergoline-8-carboxamide), citalopram, escitalopram, fluoxetine, sertraline, paroxetine, fluvoxamine, venlafaxine, duloxetine, dapoxetine, nefazodone, imipramine, femoxetine, clomipramine, combinations thereof, and pharmaceutically acceptable salts thereof.

9. The method of claim 1, wherein the one or more agents further comprise an adenylyl cyclase inhibitor.

10. The method of claim 9, wherein the adenylyl cyclase inhibitor comprises 9-tetrahydrofuryl adenine, 2',5'-dideoxyadenosine, or 9-(cyclopentyl)-adenine.

11. The method of claim 1, wherein the one or more agents further comprise an M3 receptor antagonist.

12. The method of claim 1, wherein the one or more agents further comprise a phospholipase C (PLC) inhibitor.

13. The method of claim 1, further comprising administering to the subject a primary compound comprising the formula:

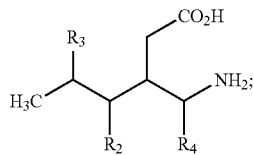

wherein $R_2$ is hydrogen or $(C_1\text{-}C_6)$ straight chain or branched unsubstituted or substituted alkyl or phenyl;

$R_3$ is straight or branched unsubstituted or substituted alkyl of from 1 to 8 carbon atoms, straight or branched alkenyl of from 2 to 8 carbon atoms, cycloalkyl of from 3 to 7 carbon atoms, alkoxy of from 1 to 6 carbon atoms, -alkylcycloalkyl, -alkylalkoxy, -alkyl, OH, -alkylphenyl, -alkylphenoxy, -phenyl or substituted phenyl;

$R_4$ is hydrogen or $(C_1\text{-}C_6)$ straight chain or branched unsubstituted or substituted alkyl, or carboxyl;

of pharmaceutically acceptable salts thereof.

14. The method of claim 1, further comprising administering to the subject a primary amine compound selected from the group consisting of:

3-Aminomethyl-5-methylhexanoic acid; 3-Aminomethyl-5-methylheptanoic acid; 3-Aminomethyl-5-methyl-octanoic acid; 3-Aminomethyl-5-methyl-nonanoic acid; 3-Aminomethyl-5-methyl-decanoic acid; 3-Aminomethyl-5-methyl-undecanoic acid; 3-Aminomethyl-5-methyl-dodecanoic acid; 3-Aminomethyl-5-methyl-tridecanoic acid; 3-Aminomethyl-5-cyclopropyl-hexanoic acid; 3-Aminomethyl-5-cyclobutyl-hexanoic acid; 3-Aminomethyl-5-cyclopentyl-hexanoic acid; 3-Aminomethyl-5-cyclohexyl-hexanoic acid; 3-Aminomethyl-5-trifluoromethyl-hexanoic acid; 3-Aminomethyl-5-phenyl-hexanoic acid; 3-Aminomethyl-5-(2-chlorophenyl)-hexanoic acid; 3-Aminomethyl-5-(3-chlorophenyl)-hexanoic acid; 3-Aminomethyl-5-(4-chlorophenyl)-hexanoic acid; 3-Aminomethyl-5-(2-ethoxyphenyl)-hexanoic acid; 3-Aminomethyl-5-(3-methoxyphenyl)-hexanoic acid; 3-Aminomethyl-5-(4-methoxyphenyl)-hexanoic acid; 3-Aminomethyl-5-(phenylmethyl)-hexanoic acid; (S)-3-(Aminomethyl)-5-methylhexanoic acid; (R)-3-(Aminomethyl)-5-methylhexanoic acid; (3R,4S)-3-Aminomethyl-4,5-dimethyl-hexanoic acid; 3-Aminomethyl-4,5-dimethyl-hexanoic acid; (3R,4S)-3-Aminomethyl-4,5-dimethyl-hexanoic acid MP; (3S,4S)-3-Aminomethyl-4,5-dimethyl-hexanoic acid; (3R,4R)-3-Aminomethyl-4,5-dimethyl-hexanoic acid MP; 3-Aminomethyl-4-isopropyl-hexanoic acid; 3-Aminomethyl-4-isopropyl-heptanoic acid; 3-Aminomethyl-4-isopropyl-octanoic acid; 3-Aminomethyl-4-isopropyl-nonanoic acid; 3-Aminomethyl-4-isopropyl-decanoic acid; 3-Aminomethyl-4-phenyl-5-methyl-hexanoic acid; (3S,5S)-3-Aminomethyl-5-methoxy-hexanoic acid; (3S,5S)-3-Aminomethyl-5-ethoxy-hexanoic acid; (3S,5S)-3-Aminomethyl-5-propoxy-hexanoic acid; (3S,5S)-3-Aminomethyl-5-isopropoxy-hexanoic acid; (3S,5S)-3-Aminomethyl-5-tert-butoxy-hexanoic acid; (3S,5S)-3-Aminomethyl-5-fluoromethoxy-hexanoic acid; (3S,5S)-3-Aminomethyl-5-(2-fluoro-ethoxy)-hexanoic acid; (3S,5S)-3-Aminomethyl-5-(3,3,3-trifluoropropoxy)-hexanoic acid; (3S,5S)-3-Aminomethyl-5-phenoxy-hexanoic acid; (3S,5S)-3-Aminomethyl-5-(4-chloro-phenoxy)-hexanoic acid; (3S,5S)-3-

Aminomethyl-5-(3-chloro-phenoxy)-hexanoic acid; (3S,5S)-3-Aminomethyl-5-(2-chloro-phenoxy)-hexanoic acid; (3S,5S)-3-Aminomethyl-5-(4-fluoro-phenoxy)-hexanoic acid; (3S,5S)-3-Aminomethyl-5-(3-fluoro-phenoxy)-hexanoic acid; (3S,5S)-3-Aminomethyl-5-(2-fluoro-phenoxy)-hexanoic acid; (3S,5S)-3-Aminomethyl-5-(4-methoxy-phenoxy)-hexanoic acid; (3S,5S)-3-Aminomethyl-5-(3-methoxy-phenoxy)-hexanoic acid; (3S,5S)-3-Aminomethyl-5-(2-methoxy-phenoxy)-hexanoic acid; (3S,5S)-3-Aminomethyl-5-(4-nitro-phenoxy)-hexanoic acid; (3S,5S)-3-Aminomethyl-5-(3-nitro-phenoxy)-hexanoic acid; (3S,5S)-3-Aminomethyl-5-(2-nitro-phenoxy)-hexanoic acid; (3S,5S)-3-Aminomethyl-6-hydroxy-5-methyl-hexanoic acid; (3S,5S)-3-Aminomethyl-6-methoxy-5-methyl-hexanoic acid; (3S,5S)-3-Aminomethyl-6-ethoxy-5-methyl-hexanoic acid; (3S,5S)-3-Aminomethyl-5-methyl-6-propoxy-hexanoic acid; (3S,5S)-3-Aminomethyl-6-isopropoxy-5-methyl-hexanoic acid; (3S,5S)-3-Aminomethyl-6-tert-butoxy-5-methyl-hexanoic acid; (3S,5S)-3-Aminomethyl-6-fluoromethoxy-5-methyl-hexanoic acid; (3S,5S)-3-Aminomethyl-6-(2-fluoro-ethoxy)-5-methyl-hexanoic acid; (3S,5S)-3-Aminomethyl-5-methyl-6-(3,3,3-trifluoro-propoxy)-hexanoic acid; (3S,5S)-3-Aminomethyl-5-methyl-6-phenoxy-hexanoic acid; (3S,5S)-3-Aminomethyl-6-(4-chloro-phenoxy)-5-methyl-hexanoic acid; (3S,5S)-3-Aminomethyl-6-(3-chloro-phenoxy)-5-methyl-hexanoic acid; (3S,5S)-3-Aminomethyl-6-(2-chloro-phenoxy)-5-methyl-hexanoic acid; (3S,5S)-3-Aminomethyl-6-(4-fluoro-phenoxy)-5-methyl-hexanoic acid; (3S,5S)-3-Aminomethyl-6-(3-fluoro-phenoxy)-5-methyl-hexanoic acid; (3S,5S)-3-Aminomethyl-6-(2-fluoro-phenoxy)-5-methyl-hexanoic acid; (3S,5S)-3-Aminomethyl-6-(4-methoxy-phenoxy)-5-methyl-hexanoic acid; (3S,5S)-3-Aminomethyl-6-(3-methoxy-phenoxy)-5-methyl-hexanoic acid; (3S,5S)-3-Aminomethyl-6-(2-methoxy-phenoxy)-5-methyl-hexanoic acid; (3S,5S)-3-Aminomethyl-5-methyl 6-(4-trifluoromethyl-phenoxy)-hexanoic acid; (3S,5S)-3-Aminomethyl-5-methyl 6-(3-trifluoromethyl-phenoxy)-hexanoic acid; (3S,5S)-3-Aminomethyl-5-methyl 6-(2-trifluoromethyl-phenoxy)-hexanoic acid; (3S,5S)-3-Aminomethyl-5-methyl 6-(4-nitro-phenoxy)-hexanoic acid; (3S,5S)-3-Aminomethyl-5-methyl 6-(3-nitro-phenoxy)-hexanoic acid; (3S,5S)-3-Aminomethyl-5-methyl 6-(2-nitro-phenoxy)-hexanoic acid; (3S,5S)-3-Aminomethyl-6-benzyloxy-5-methyl-hexanoic acid; (3S,5S)-3-Aminomethyl-7-hydroxy-5-methyl-heptanoic acid; (3S,5S)-3-Aminomethyl-7-methoxy-5-methyl-heptanoic acid; (3S,5S)-3-Aminomethyl-7-ethoxy-5-methyl-heptanoic acid; (3S,5S)-3-Aminomethyl-5-methyl-7-propoxy-heptanoic acid; (3S,5S)-3-Aminomethyl-7-isopropoxy-5-methyl-heptanoic acid; (3S,5S)-3-Aminomethyl-7-tert-butoxy-5-methyl-heptanoic acid; (3S,5S)-3-Aminomethyl-7-fluoromethoxy-5-methyl-heptanoic acid; (3S,5S)-3-Aminomethyl-7-(2-fluoro-ethoxy)-5-methyl-heptanoic acid; (3S,5S)-3-Aminomethyl-5-methyl-7-(3,3,3-trifluoro-propoxy)-heptanoi-c acid; (3S,5S)-3-Aminomethyl-7-benzyloxy-5-methyl-heptanoic acid; (3S,5S)-3-Aminomethyl-5-methyl-7-phenoxy-heptanoic acid; (3S,5S)-3-Aminomethyl-7-(4-chloro-phenoxy)-5-methyl-heptanoic acid; (3S,5S)-3-Aminomethyl-7-(3-chloro-phenoxy)-5-methyl-heptanoic acid; (3S,5S)-3-Aminomethyl-7-(2-chloro-phenoxy)-5-methyl-heptanoic acid; (3S,5S)-3-Aminomethyl-7-(4-fluoro-phenoxy)-5-methyl-heptanoic acid; (3S,5S)-3-Aminomethyl-7-(3-fluoro-phenoxy)-5-methyl-heptanoic acid; (3S,5S)-3-Aminomethyl-7-(2-fluoro-phenoxy)-5-methyl-heptanoic acid; (3S,5S)-3-Aminomethyl-7-(4-methoxy-phenoxy)-5-methyl-heptanoic acid; (3S,5S)-3-Aminomethyl-7-(3-methoxy-phenoxy)-5-methyl-heptanoic acid; (3S,5S)-3-Aminomethyl-7-(2-methoxy-phenoxy)-5-methyl-heptanoic acid; (3S,5S)-3-Aminomethyl-5-methyl-7-(4-trifluoromethyl-phenoxy)-heptan-oic acid; (3S,5S)-3-Aminomethyl-5-methyl-7-(3-trifluoromethyl-phenoxy)-heptan-oic acid; (3S,5S)-3-Aminomethyl-5-methyl-7-(2-trifluoromethyl-phenoxy)-heptan-oic acid; (3S,5S)-3-Aminomethyl-5-methyl-7-(4-nitro-phenoxy)-heptanoic acid; (3S,5S)-3-Aminomethyl-5-methyl-7-(3-nitro-phenoxy)-heptanoic acid; (3S,5S)-3-Aminomethyl-5-methyl-7-(2-nitro-phenoxy)-heptanoic acid; (3S,5S)-3-Aminomethyl-5-methyl-6-phenyl-hexanoic acid; (3S,5S)-3-Aminomethyl-6-(4-chloro-phenyl)-5-methyl-hexanoic acid; (3S,5S)-3-Aminomethyl-6-(3-chloro-phenyl)-5-methyl-hexanoic acid; (3S,5S)-3-Aminomethyl-6-(2-chloro-phenyl)-5-methyl-hexanoic acid; (3S,5S)-3-Aminomethyl-6-(4-methoxy-phenyl)-5-methyl-hexanoic acid; (3S,5S)-3-Aminomethyl-6-(3-methoxy-phenyl)-5-methyl-hexanoic acid; (3S,5S)-3-Aminomethyl-6-(2-methoxy-phenyl)-5-methyl-hexanoic acid; (3S,5S)-3-Aminomethyl-6-(4-fluoro-phenyl)-5-methyl-hexanoic acid; (3S,5S)-3-Aminomethyl-6-(3-fluoro-phenyl)-5-methyl-hexanoic acid; (3S,5S)-3-Aminomethyl-6-(2-fluoro-phenyl)-5-methyl-hexanoic acid; (3S,5R)-3-Aminomethyl-5-methyl-7-phenyl-heptanoic acid; (3S,5R)-3-Aminomethyl-7-(4-chloro-phenyl)-5-methyl-heptanoic acid; (3S,5R)-3-Aminomethyl-7-(3-chloro-phenyl)-5-methyl-heptanoic acid; (3S,5R)-3-Aminomethyl-7-(2-chloro-phenyl)-5-methyl-heptanoic acid; (3S,5R)-3-Aminomethyl-7-(4-methoxy-phenyl)-5-methyl-heptanoic acid; (3S,5R)-3-Aminomethyl-7-(3-methoxy-phenyl)-5-methyl-heptanoic acid; (3S,5R)-3-Aminomethyl-7-(2-methoxy-phenyl)-5-methyl-heptanoic acid; (3S,5R)-3-Aminomethyl-7-(4-fluoro-phenyl)-5-methyl-heptanoic acid; (3S,5R)-3-Aminomethyl-7-(3-fluoro-phenyl)-5-methyl-heptanoic acid; (3S,5R)-3-Aminomethyl-7-(2-fluoro-phenyl)-5-methyl-heptanoic acid; (3S,5R)-3-Aminomethyl-5-methyl-oct-7-enoic acid; (3S,5R)-3-Aminomethyl-5-methyl-non-8-enoic acid; (E)-(3S,5S)-3-Aminomethyl-5-methyl-oct-6-enoic acid; (Z)-(3S,5S)-3-Aminomethyl-5-methyl-oct-6-enoic acid; (Z)-(3S,5S)-3-Aminomethyl-5-methyl-non-6-enoic acid; (E)-(3S,5S)-3-Aminomethyl-5-methyl-non-6-enoic acid; (E)-(3S,5R)-3-Aminomethyl-5-methyl-non-7-enoic acid; (Z)-(3S,5R)-3-Aminomethyl-5-methyl-non-7-enoic acid; (Z)-(3S,5R)-3-Aminomethyl-5-methyl-dec-7-enoic acid; (E)-(3S,5R)-3-Aminomethyl-5-methyl-undec-7-enoic acid; (3S,5S)-3-Aminomethyl-5,6,6-trimethyl-heptanoic acid; (3S,5S)-3-Aminomethyl-5,6-dimethyl-heptanoic acid; (3S,5S)-3-Aminomethyl-5-cyclopropyl-hexanoic acid; (3S,5S)-3-Aminomethyl-5-cyclobutyl-hexanoic acid; (3S,5S)-3-Aminomethyl-5-cyclopentyl-hexanoic acid; (3S,5S)-3-Aminomethyl-5-cyclohexyl-hexanoic acid; (3S,5R)-3-Aminomethyl-5-methyl-heptanoic acid; (3S,5R)-3-Aminomethyl-5-methyl-octanoic acid; (3S,5R)-3-Aminomethyl-5-methyl-nonanoic acid; (3S,5R)-3-Aminomethyl-5-methyl-decanoic acid; (3S,5R)-3-Aminomethyl-5- methyl-undecanoic acid; (3S,5R)-3-Aminomethyl-5-methyl-dodecanoic acid; (3S,5R)-3-Aminomethyl-5,9-dimethyl-decanoic acid; (3S,5R)-3-Aminomethyl-5,7-dimethyl-octanoic acid; (3S,5R)-3-Aminomethyl-5,8-dimethyl-nonanoic acid; (3S,5R)-3-Aminomethyl-6-cyclopropyl-5-methyl-hexanoic acid; (3S,5R)-3-Aminomethyl-6-cyclobutyl-5-methyl-hexanoic acid; (3S,5R)-3-Aminomethyl-6-cyclopentyl-5-methyl-hexanoic acid; (3S,5R)-3-Aminomethyl-6-cyclohexyl-5-methyl-hexanoic acid; (3S,5R)-3-Aminomethyl-7-cyclopropyl-5-methyl-heptanoic acid; (3S,5R)-3-Aminomethyl-7-cyclobutyl-5-methyl-heptanoic acid; (3S,5R)-3-Aminomethyl-7-cyclopentyl-5-methyl-heptanoic acid; (3S,5R)-3-Aminomethyl-7-cyclohexyl-5-methyl-heptanoic acid; (3S,5R)-3-Aminomethyl-8-cyclopropyl-5-methyl-octanoic acid; (3S,5R)-3-Aminomethyl-8-cyclobutyl-5-methyl-octanoic acid; (3S,5R)-3-Aminomethyl-8-cyclopentyl-5-methyl-octanoic acid; (3S,5R)-3-Aminomethyl-8-cyclohexyl-5-methyl-octanoic acid; (3S,5S)-3-Aminomethyl-6-fluoro-5-methyl-hexanoic acid; (3S,5S)-3-Aminomethyl-7-fluoro-5-methyl-heptanoic acid; (3S,5R)-3-Aminomethyl-8-fluoro-5-methyl-octanoic acid; (3S,5R)-3-Aminomethyl-9-fluoro-5-methyl-nonanoic acid; (3S,5S)-3-Aminomethyl-7,7,7-trifluoro-5-methyl-heptanoic acid; (3S,5R)-3-Aminomethyl-8,8,8-trifluoro-5-methyl-octanoic acid; (3S,5R)-3-Aminomethyl-5-methyl-8-phenyl-octanoic acid; (3S,5S)-3-Aminomethyl-5-methyl-6-phenyl-hexanoic acid; (3S,5R)-3-Aminomethyl-5-methyl-7-phenyl-heptanoic acid; and pharmaceutically acceptable salts thereof.

15. The method of claim 1, wherein the doxazocin and guanabenz are administered systemically to the subject.

16. A method of treating light induced retinal degeneration in the retina of a subject in need thereof, comprising:
systemically administering to the subject one or more agents that inhibit and/or block the activation of Gs- or Gq-protein coupled receptors or Gs- or Gq-signaling cascade in ocular cells of the subject, and/or activate Gi-protein coupled receptors, wherein the one or more agents include doxazosin and guanabenz that are administered at an amount that yields more than additive effect in protecting the retina from bright light-induced degeneration, wherein the activation of the Gs- or Gq-protein coupled receptors or Gs- or Gq-signaling cascade is induced or triggered by light induced all-trans-retinal generation.

17. The method of claim 1, wherein the light induced retinal degeneration in the retina is associated with geographic atrophy (GA) or Stargardt disease.

18. The method of claim 16, wherein the light induced retinal degeneration in the retina is associated with geographic atrophy (GA) or Stargardt disease.

* * * * *